US006300490B1

(12) United States Patent
Huber et al.

(10) Patent No.: US 6,300,490 B1
(45) **Date of Patent: *Oct. 9, 2001**

(54) MOLECULAR CONSTRUCTS COMPRISING A CARCINOEMBRYONIC ANTIGEN (CEA) TRANSCRIPTIONAL REGULATORY REGION

(75) Inventors: Brian Huber; Cynthia A. Richards, both of Durham; Elizabeth A. Austin, Raleigh, all of NC (US)

(73) Assignee: Glaxo Wellcome Inc., Research Triangle Park, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/481,968

(22) Filed: Jun. 7, 1995

Related U.S. Application Data

(63) Continuation of application No. 08/154,712, filed on Nov. 19, 1993, which is a continuation-in-part of application No. 07/841,961, filed on Feb. 26, 1992, now abandoned, which is a continuation-in-part of application No. 07/662,222, filed on Feb. 22, 1991, now abandoned, which is a continuation-in-part of application No. 07/574,994, filed on Sep. 27, 1990, now abandoned.

(30) Foreign Application Priority Data

Aug. 30, 1989 (GB) .................................................. 8919607

(51) Int. Cl.[7] ............................ C07H 21/04; C12N 15/85

(52) U.S. Cl. .................... 536/23.7; 435/320.1; 536/23.1; 536/24.1

(58) Field of Search ............................... 435/69.1, 172.3, 435/320.1; 536/23.1, 24.1, 23.5, 23.7; 424/93.1, 93.6, 93.2

(56) References Cited

U.S. PATENT DOCUMENTS

| | | | |
|---|---|---|---|
| 5,338,678 | 8/1994 | Senter et al. | 435/227 |
| 5,358,866 | 10/1994 | Mullen et al. | 435/357 |
| 5,624,830 | 4/1997 | Mullen et al. | 435/456 |
| 5,691,177 * | 11/1997 | Guber et al. | 435/456 |
| 5,888,502 | 3/1999 | Guber et al. | 424/93.21 |

FOREIGN PATENT DOCUMENTS

| | | |
|---|---|---|
| 0 181 150 A1 | 5/1986 | (EP) . |
| 0243204 | 10/1987 | (EP) . |
| 0 272 065 A2 | 6/1988 | (EP) . |
| 0 273 127 A2 | 7/1988 | (EP) . |
| 0 293 193 A2 | 11/1988 | (EP) . |
| 0 293 193 A3 | 11/1988 | (EP) . |
| 0 294 114 A2 | 12/1988 | (EP) . |
| 0 334 301 A1 | 9/1989 | (EP) . |
| 0 415 731 A2 | 3/1991 | (EP) . |
| WO 89/07136 | 8/1989 | (WO) . |
| WO 90/07936 | 7/1990 | (WO) . |
| WO 91/02805 | 3/1991 | (WO) . |
| 92/04901 | 4/1992 | (WO) . |
| 92/10564 | 6/1992 | (WO) . |
| 93/01281 | 1/1993 | (WO) . |
| 93/21959 | 11/1993 | (WO) . |

OTHER PUBLICATIONS

Sikora, "Gene Therapy for Cancer," *Trends in Biotechnology*, vol. II, No. 5, May 1993, pp. 197–201.
S. Ahmad et al., *Molec. Gen. Genet.*, 118:323–325 (1972).
Anderson et al., *Arcl. Microbiol.*, 152:115–118 (1989).
T. Kulikowski et al., *Nucleic Acids Research*, Sympos. No. 9 (1981), pp. 103–106.
T. Kurihara et al., *Mol. Gen. Genet.*, 190:189–195 (1983).
C. Mullen et al., *Cancer Research*, 54:1–4 (1994).
J.M. Daly et al., "Therapy of Colorectal Hepatic Metastases", *Import. Adv. Oncol.*, 251–268 (1986).
N.W. Swinton et al., *Dis. Colon Rectum*, 7:273–277 (1964).
W.F. Anderson, *Science*, 226:401–409 (1984).
C. Desgranges et al., *Cancer Research*, 46:1094 (1986).
M.H. Sawyer et al., *Virology*, 149:1–9 (1986).
C.A. Richards et al., *Cancer Research*, 50:1521–1527 (1990).
J.R. De Wet et al., *Molecular and Cellular Biology*, 7:725–737 (1987).
E. Reist et al., *J. Org. Chem.*, 27:3274–3279 (1962).
C. Smith et al., *Cancer Treatment Rep.*, 60:1567–1584 (1976).
M. Legraverend et al., *Tetrahedron*, 40:709–713 (No. 4) (1984).
J. Brink et al., *Canadian J. Biochem.*, 43:1–15 (No. 1) (1965).
J. Montgomery et al., *J. Med. Chem.*, 12:498–504 (1969).
T. Krenitsky et al., *J. Biol. Chem.*, 251:4055–4061 (No. 13) (1976).
T. Haskell, *Ann. N.Y. Acad. Sci.*, 284:81–90 (1977).
E. De Clercq et al., *J. Med. Chem.*, 26:661–666 (No. 5) (1983).
J. Goodchild et al., *J. Med. Chem.*, 26:1252–1257 (No. 9) (1983).
H. Machida et al., *Antimicrobial Agents Chemother.*, 17:1030–1031 (No. 6) (1980).
Y. Cheng et al., *Biochem. Pharmacol.*, 32:726–729 (No. 4) (1983).

(List continued on next page.)

*Primary Examiner*—David Guzo
(74) *Attorney, Agent, or Firm*—Virginia C. Bennett

(57) ABSTRACT

Novel molecular chimaeras produced by recombinant DNA techniques are described. They comprise a target-tissue specific transcriptional regulatory sequence (TRS) linked and controlling the expression of a heterologous enzyme, for example Varicella Zoster Virus Thymidine Kinase (VZV TK) or non-mammaliam Cytosine Deaminase(CD). A molecular chimaera is packaged into a synthetic retroviral particle that is capable of infecting mammalian tissue. This, in turn, may be administered to a host, and the TRS will be selectively transcriptionally activated in the target tissue (for example cancerous cells). Administration of compounds that are selectively metabolised by the enzyme produce cytotoxic or cytostatic metabolites in situ thereby selectively killing or arresting the growth of the target cells.

3 Claims, 40 Drawing Sheets

OTHER PUBLICATIONS

J. Locker et al., *J. DNA Sequencing and Mapping*, 1:3–11 (1990).

C. Richards et al., *J. DNA Sequencing and Mapping*, 4:185–196 (No. 3) (1993).

Farley et al., "Colorectal Cancer", *Postgraduate Medicine*, 84(No. 6): 175–183 (1988).

Ilien et al., "New Photoaffinity Labels for Rat Brain Muscarinic Acetylcholine Receptors", *Biochem. Pharmacology*, 38(17):2879–2887 (1989).

Robbins et al., "Nucleic Acid Related Compounds . . . ", *J. Org. Chem.*, 48(No. 11):1854–1862 (1983).

Silverberg, ed., "Cancer Statistics, 1983", *Cancer Journal for Clinicians*, 33(No. 1):9–25 (1983).

Silverberg, ed., "Cancer Statistics, 1986", *Cancer Journal for Clinicians*, 36(No. 1):9–25 (1986).

Gilboa, et al., Transfer and Expression of Cloned Genes Using Retroviral Vectors, Bio Techniques, vol. 4, No. 6, pp. 504–512 (1986).

Neurath, et al., Biological Role of Pre–S Sequences of the Hepatitis B Virus Envelope Protein, Hepadna Viruses, pp. 189–203 (1987).

Pontisso, et al., Recombinant HBsAg Particles Containing Pre–S Proteins Bind to Human Liver Plasma Membranes, Hepadna Viruses, pp. 205–221 (1987).

Sawyer, et al., Molecular Analysis of the Pyrimidine Deoxyribonucleoside Kinase Gene of Wild–type and Acvclovir–resistant Strains of Varicella–Zoster Virus, J. Gen. Virol., 69, 2585–2593 (1988).

Seeman, et al., Analytical Solution to the Curtin–Hammett/ Winstein–Holness Kinetic System, J. Org. Chem., vol. 43, No. 10, 1854–1864 (1978).

Smith, et al., Inhibitors of Hypoxanthine Metabolism in Ehrlich Ascites Tumor Cells in Vitro, Cancer Treatment Reports, vol. 60, No. 10, pp. 1567–1584 (1976).

Vandevelde, A., 5–Fluorocytosine in the Treatment of Mycotic Infections, Annals of Internal Medicine 77:43–51 (1972).

Eglitis, et al., Science, Dec. 20, 1985, vol. 230, Gene Expression in Mice After High Efficiency Retroviral–Mediated Gene Transfer, pp. 1395–1398.

Eglitis, et al., BioTechniques, vol. 6, No. 7, (1988), Retroviral Vectors for Introduction of Genes into Mammalian Cells, pp. 608–614.

Nerestone, et al., Cancer Treatment Reviews, (1988), 15, 1:31, Clinical trials in primary hepatocellular carcinoma: current status and future directions.

Peter D. Senter, The FASEB Journal, vol. 4, Feb., 1990, Activation of prodrugs by antibody–enzyme conjugates: a new approach to cancer therapy, pp. 188–193.

Davison, et al., J. gen. Virol., (1986), 67, The Complete DNA Sequence of Varicella–Zoster Virus, pp. 1759–1816.

Jagodzinski, et al., Proc. Natl. Acad. Sci. USA, vol. 78, No. 6, Sequence homology between RNAs encoding rat L–fetoprotein and rat serum albumin, pp. 3521–3525.

Maniatis, et al., Articles, Science, vol. 236, Jun., 1987, Regulation of Inducible and Tissue–Specific Gene Expression, pp. 1237–1245.

Miller, et al., Molecular and Cellular Biology, Aug., 1986, vol. 6, No. 8, Redesign of Retrovirus Packaging Cell Lines to Avoid Recombination Leading to Helper Virus Production, pp. 2895–2902.

Huber, et al., Oncogene, (1988), 3, Expression and phenotypic alterations caused by an inducible transforming ras oncogene introduced into rat liver epithelial cells, pp. 245–256.

Hammer, et al., Research Articles, Scienc,e vol. 23, Jan., 1987, Diversity of Alpha–Fetoprotein Gene Expression in Mice Is Generated by a Combination of Separate Enhancer Elements, pp. 53–58.

Krumlauf, et al., Molecular and Cellular Biology, Jul., 1985, vol. 5, No. 7, Developmental Regulation of L–Fetoprotein Genes in Transgenic Mice, pp. 1639–1648.

Zimmermann et al., Isolation and characterization of cDNA clones encoding the human carcinoembryonic antigen reveal a highly conserved repeating structure, *Proc. Natl. Acad. Sci. USA*, 84:2960–2964 (1987).

Rudert et al., Characterization of murine carcinoembryonic antigen gene family members, *Mammalian Genome*, 3:262–273 (1992).

Rudert et al., Ubiquitous Nuclea rFactors Bind Specifically to a 5'–Region Conserved in Carcinoembryonic Antigen–Related Genes, *Biochem Biophys Res Commun.* 18B(3):893–901 (1992).

Borrelli et al. "Targeting of an inducible toxic phenotype in animal cells", PNAS, vol. 85, pp. 7572–7576, Oct. 1988.*

Moolton, "An alternative to the magic bullet paradigm for specific cancer therapy", Medical Hypotheses, vol. 24, pp. 43–51, 1987.*

Nishiyama et al., "Antineoplastic effects in rats of 5–fluorocytosine in combination with cytosine deaminase capsules", Cancer Res., vol. 45, pp. 17553–1761, Apr. 1985.*

Thompson et al., PNAS, vol. 84, pp. 2965–2969, May 1987.*

Maxwell et al, "Targeted Cell Suicide by Toxin Gene Expression", Gene Transfer and Gene Therapy, pp. 189–204 (1989).

Borrelli et al, "Inducible Ablation of a Specific Cell Type by the Herpes Thymidine Kinase Gene Expression", Gene Transfer and Gene Therapy, pp. 163–177 (1989).

Berkner, Kathleen L., "Development of Adenovirus Vectors for the Expression of Heterologous Genes", Biotechniques 6:616–629 (1988).

Stratford–Perricaudet et al, "Evaluation of the Transfer and Expression in Mice of an Enzyme–Encoding Gene Using a Human Adenovirus Vector", Human Gene Therapy 1:241–256 (1990).

Ballay et al, "In vitro and in vivo synthesis of the hepatitis B virus surface antigen and of the receptor for polymerized human serum albumin from recombinant human adenoviruses", The EMBO Journal 4(13B):3861–3865 (1985).

Godbout, et al., Multiple Regulatory Elements in the Intergenic Region Between the alpha–Fetoprotein and Albumin Genes, Mollecular and Cellular Biology, vol. 6, No. 2, pp. 477–487 (1986).

Heyman, et al., Thymidine Kinase Obliteration: Creation of Transgenic Mice with Controlled Immune Deficiency, Proc. Natl. Acad. Sci. USA, vol. 86, pp. 2698–2702 (1989).

Huber, et al., Retroviral–medicated gene therapy for the treatment of hepato–cellular carcinoma: an Innovative Approach for Cancer Therapy, Proc. Natl. Acad. Sci. USA, vol. 88, pp. 8039–8043 (1991).

Ingram, et al., Alpha–Fetoprotein and albumin genes are in tandem in the mouse genome, Proc. Natl. Acad. Sci. USA, vol. 78, No. 8, pp. 4694–4698 (1981).

Mullen, et al., Transfer of the bacterial gene for cytosine deaminase to mammalian cells confers lethal sensitivity to 5–fluorocytosine: A negative selection system, Proc. Natl. Acad. Sci. USA, vol. 89, pp. 33–37 (1992).

Pinkert, et al., An albumin enhancer located 10 kb upstream functions along with its promoter to direct efficient, liver–specific expression in transgenic mice, Gene & Development 1:268–276 (1987).

Schrewe, et al., Cloning of the Complete Gene for Carcinoembryonic Antigen: Analysis of Its Promoter Indicates a Region Conveying Cell Type–Specific Expression, Molecular and Cellular Biology, vol. 10, No. 6, pp. 2738–2748 (1990).

Watanabe, et al., Cell–Specific Enhancer Activity in a Far Upstream Region of the Human alpha–Fetoprotein Gene, J. Biol. Chem., vol. 262, No. 10, pp. 4812–4818 (1987).

Willcocks, et al., Characterization of the Genomic Organization of Human Carcinoembryonic Antigen (CEA): Comparison with Other Family Members and Sequence Analysis of 5' Controlling Region, Genomics 8, 492–500 (1990).

Brink, et al., 9–beta–D–Arabinofuranosyladenine as an Inhibitor of Metabolism in Normal and Neoplastic Cells, Can. J. Biochem., vol. 43, No. 1, pp. 1–15 (1965).

Kew, M., Hepatocellular carcinoma, Postgrad. Med. J., 59 (Suppl. 4), 78–87 (1983).

McCormick, D., Human Gene Therapy: The First Round, Biotechnology, vol. 3, No. 8, pp. 689–693 (1985).

* cited by examiner

Albumin Enhancer and Promoter Sequences

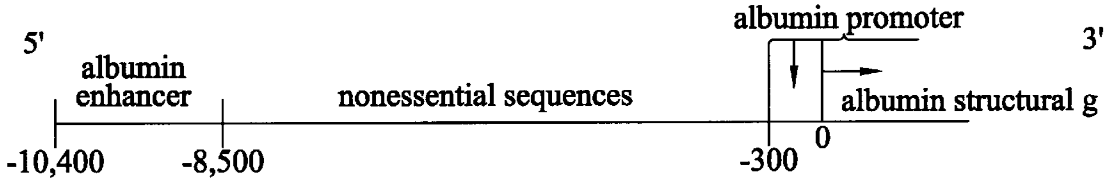

liver-specific expression of albumin

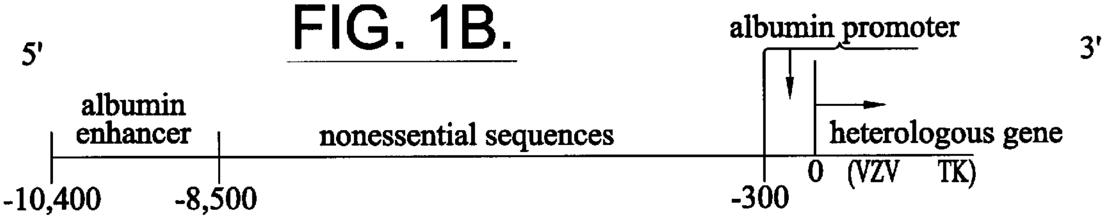

liver-specific expression of heterologous gene (VZV TK) ligated 3' and in proper orientation to the complete albumin enhancer and promoter sequences

FIG. 1C.

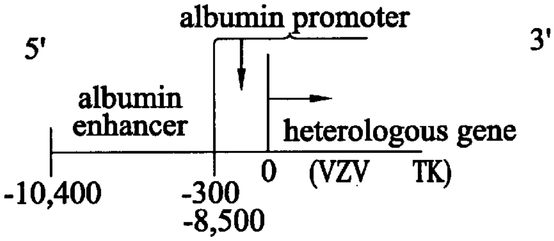

liver-specific expression of heterologous gene (VZV TK) ligated 3' and in proper orientation to trucated albumin regulatory sequences transcription initiation start site.

Diagram of the Varicella Zoster Thymidine Kinase Gene.

FIG. 2B/1

Sequence of the Varicella zoster thymidine kinase domain. Shown is the sequence of the VZV TK gene and the 5′ and 3′ flanking regions (bases 64276 to 66255 as reported in Gen. Virol. 67:1759-1816, 1986). The VZV TATA box and polyadenylation are underlined. The Acc I and Nde I restriction endonuclease sites used to subclone the 1381 bp Acc I/Nde I fragment containing the VZV TK coding sequence and polyadenylation signal are shown. This 1381 bp fragment is ligated 3′ and in the proper orientation to liver specific or hepatoma specific transcriptional regulatory sequences to achieve liver specific or hepatoma specific expression respectively.

FIG. 2B/2

```
cctgtaacag gttcagaccc cgttgagata caaacacaag gagggggtc accattattt   60

catcagatcc cgtgggtgtg gtttccttta ttaaagccat ggtatccctc agctggcgca  120
                             TATA Box
taccctcgca aaactggtga tacttagtag gggtatgtat attagcgcta aaacggcaag  180

attttaattc cactataaaa caaacggtct ttccggcacc actggattcc gtttgtataa  240

tacaaacaca atcggggcgt cggcgtccca aatttacttc aaacgacatt gatatgcgta  300

cagccctttg aacatccacg tgggataacg gcgacaggag ttttgccagc ctcgggttga  360

acgcgtccgc gaaacctcga cgtacgttat caatatcctt tttgagtaca tcgtaaaaac  420

gagtgtggca acgttgtccc aaacgaaaac acttggcccg aattcgacta gcggacatat  480

ttgaagttcc gtcccagaag ataacctaag acgcgtttgt ctacaataaa catgtcaacg  540
                                            AccI          MetSerThr

gataaaaccg atgtaaaaat gggcgttttg cgtatttatt tggacggggc gtatggaatt  600
AspLysThrA spValLysMe tGlyValLeu ArgIleTyrL euAspGlyAl aTyrGlyIle

ggaaaaacga ccgccgccga agaattttta caccactttg caataacacc aaaccggatc  660
GlyLysThrT hrAlaAlaGl uGluPheLeu HisHisPheA laIleThrPr oAsnArgIle

ttactcattg gggagcccct gtcgtattgg cgtaaccttg caggggagga cgccatttgc  720
LeuLeuIleG lyGluProLe uSerTyrTrp ArgAsnLeuA laGlyGluAs pAlaIleCys

ggaatttacg gaacacaaac tcgccgtctt aatggagacg tttcgcctga agacgcacaa  780
GlyIleTyrG lyThrGlnTh rArgArgLeu AsnGlyAspV alSerProGl uAspAlaGln

cgcctcacgg ctcattttca gagcctgttc tgttctccgc atgcaattat gcatgcgaaa  840
ArgLeuThrA laHisPheGl nSerLeuPhe CysSerProH isAlaIleMe tHisAlaLys

atctcggcat tgatggacac aagtacatcg gatctcgtac aagtaaataa ggagccgtat  900
IleSerAlaL euMetAspTh rSerThrSer AspLeuValG lnValAsnLy sGluProTyr

aaaattatgt tatccgaccg acacccaatc gcctcaacta tatgttttcc cttgtccaga  960
LysIleMetL euSerAspAr gHisProIle AlaSerThrI leCysPhePr oLeuSerArg

tacttagtgg gagatatgtc cccagcggcg cttcctgggt tattgtttac gcttcccgct 1020
TyrLeuValG lyAspMetSe rProAlaAla LeuProGlyL euLeuPheTh rLeuProAla

gaaccccccg ggaccaactt ggtagtttgt accgtttcac tccccagtca tttatccaga 1080
GluProProG lyThrAsnLe uValValCys ThrValSerL euProSerHi sLeuSerArg

gtaagcaaac gggccagacc gggagaaacg gttaatctgc cgtttgttat ggttctgaga 1140
ValSerLysA rgAlaArgPr oGlyGluThr ValAsnLeuP roPheValMe tValLeuArg
```

FIG. 2B/3

```
aatgtatata taatgcttat taatacaatt atatttctta aaactaacaa ctggcacgcg 1200
AsnValTyrI leMetLeuIl eAsnThrIle IlePheLeuL ysThrAsnAs nTrpHisAla

ggctggaaca cactgtcatt ttgtaatgat gtatttaaac agaaattaca aaaatccgag 1260
GlyTrpAsnT hrLeuSerPh eCysAsnAsp ValPheLysG lnLysLeuGl nLysSerGlu

tgtataaaac tacgcgaagt acctgggatt gaagacacgt tattcgccgt gcttaaactt 1320
CysIleLysL euArgGluVa lProGlyIle GluAspThrL euPheAlaVa lLeuLysLeu

ccggagcttt gcggagagtt tggaaatatt ctgccgttat gggcatgggg aatggagacc 1380
ProGluLeuC ysGlyGluPh eGlyAsnIle LeuProLeuT rpAlaTrpGl yMetGluThr

ctttcaaact gcttacgaag catgtctccg ttcgtattat cgttagaaca gacaccccag 1440
LeuSerAsnC ysLeuArgSe rMetSerPro PheValLeuS erLeuGluGl nThrProGln

catgcggcac aagaactaaa aactctgcta ccccagatga ccccggcaaa catgtcctcc 1500
HisAlaAlaG lnGluLeuLy sThrLeuLeu ProGlnMetT hrProAlaAs nMetSerSer

ggtgcatgga atatattgaa agagcttgtt aatgccgttc aggacaacac ttcctaaata 1560
GlyAlaTrpA snIleLeuLy sGluLeuVal AsnAlaValG lnAspAsnTh rSerEnd

tacctagtat ttacgtatgt accagtaaaa agatgataca cattgtcata ctcgcgtgta 1620
                Polyadenylation Signal
cgtgtttttc tttttatat atgcgtcatt tattaccaca tcctttaatc ccgcctttat 1680

ctccctaaaa cggagtggta atattaaaag ccgccaagcc tgttggtggg tgaggagggg 1740

taaaggcacg ctgtgtgcat aacgttgcgg tgatattgta gcgcaagtaa cagcgactat 1800

gtttgcgcta gttttagcgg tggtaattct tcctctgtgg accacggcta ataaatctta 1860

cgtaacacca acccctgcga ctcgctctat cggacatatg tctgctcttc tacgagaata 1920
                                     NdeI
ttccgaccgt aatatgtctc tgaaattaga agccttttat cctactggtt tcgatgaaga 1980
```

Results in liver-specific expression of VZV TK.

*|* polyadenylation signal transcription initiation start site.

Results in hepatoma-specific expression of VZV TK in addition to other neoplastic tissues which express AFP such as certain tumors of the gastrointestinal tract and testis.

*|* polyadenylation signal transcription initiation start site.

Proviral form of artificial retroviral shuttle vector containing the artificial molecular chimaera of AFP transcriptional regulatory sequences and the coding sequence of the VZV TK gene.

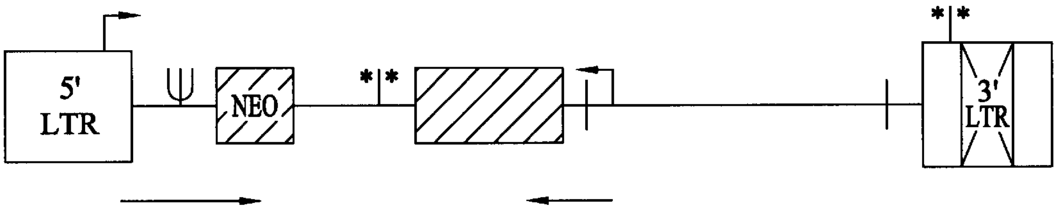

KEY

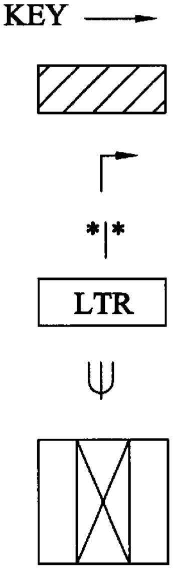

direction of transcription protein coding sequence transcription initiation start site polyadenylation signal for the VZV TK gene and in 3' LTR long terminal repeat regulatory sequence psi site, cis acting regulatory sequence the transcriptional regulatory sequences are deleted from the 3' LTR to create a SIN vector (self-inactivating vector), SIN vectors will produce a provirus incorporated into the target cell with both LTR transcriptional regulatory sequences deleted. This will produce a provirus with the AFP transcriptional regulatory sequences (or others as indicated) as the only functional promoter and enhancers in the provirus.

FIG. 4A.

Proviral form of the artificial retroviral shuttle containing the artificial molecular chimaera of AFP transcriptional regulatory sequences and the coding sequence of the VZV TK gene. Illustrated is this artificial shuttle vector contained in a plasmid for amplification in bacteria. The illustrated plasmid is a derivative of PBR 322. The shuttle vector is a derivative of the Moloney murine leukemia virus. Such shuttle vectors based on the Moloney murine leukemia virus have been described as exemplified by the N2 vector (Science 230 : 1395 - 1398 [1985]).

| ENZYMES | # Sites |
|---|---|
| 1 HIND3 | 5 |
| JUNCTIONS: | |
| 2 PST1/XHO1 | 1 |
| 3 AAT2/XHO1 | 1 |

Tic=1600

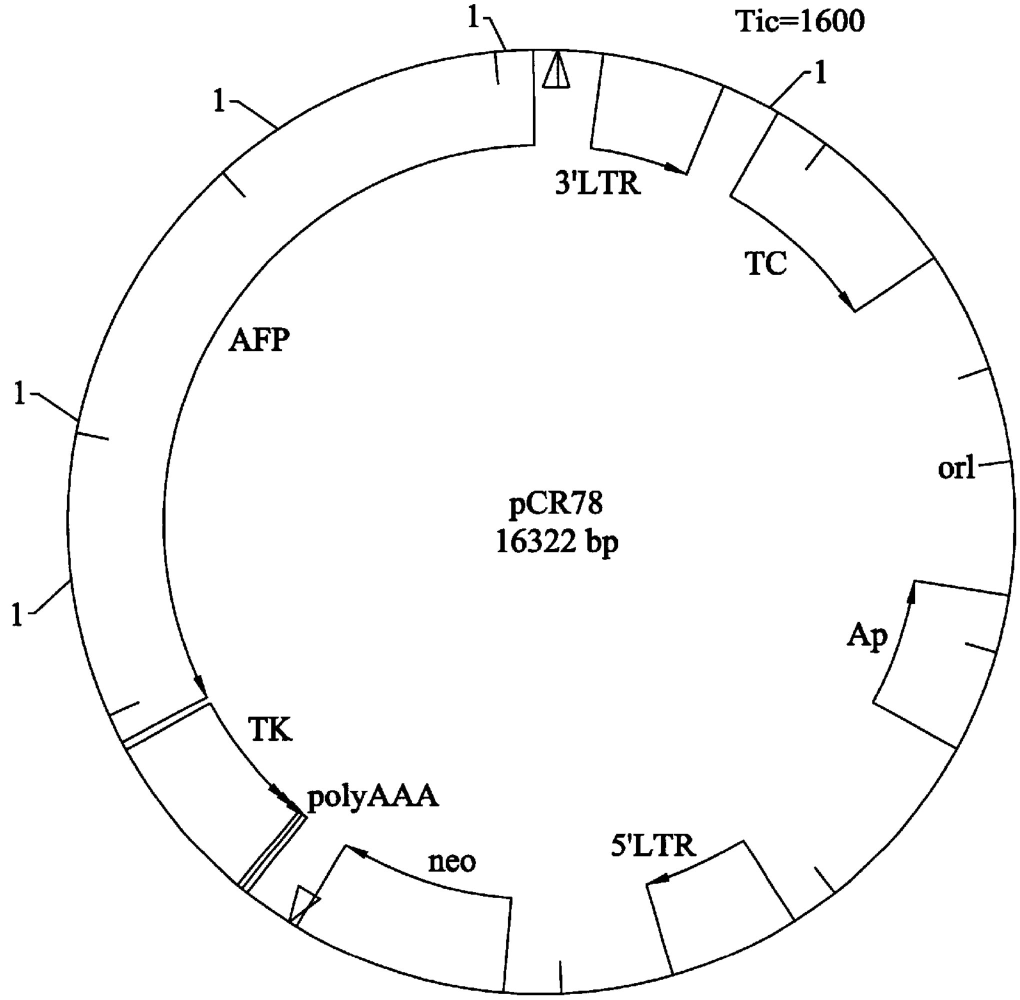

FIG. 4B.

SUMMARY FLOW CHART FOR THE CONSTRUCTION OF pCR74 THAT IS DETAILED IN EXAMPLES 1 AND 3

SUMMARY FLOW CHART FOR THE CONSTRUCTION OF pCR78 THAT IS DETAILED IN EXAMPLES 2 AND 4

**Sequences flanking the junction of the murine ALB E/P to the VZV TK sequence in pCR74. Sequences 1-140 are from the murine ALB E/P. Sequences 141-276 are from VZV. The ALB proximal promoter element is double underlined. The start of RNA transcription is marked by an asterisk (*). The BamH I site is underlined. The vertical line marks the junction between ALB and VZV sequences. The displayed VZV coding sequence is translated.**

```
        10         20         30         40         50         60
ATGGTATGAT TTTGTAATGG GGTAGGAACC AATGAAATGC GAGGTAAGTA TGGTTAATGA

        70         80         90        100        110    *   120
TCTACAGTTA TTGGTTAAAG AAGTATATTA GAGCGAGTCT TTCTGCACAC AGATCACCTT

       130        140        150        160        170        180
TCCTATCAAC CCCGGGATCC|TACAATAAAC ATGTCAACGG ATAAAACCGA TGTAAAAATG
              BamHI              MetSerThr AspLysThrAs pValLysMet

       190        200        210        220        230        240
GGCGTTTTGC GTATTTATTT GGACGGGGCG TATGGAATTG GAAAAACGAC CGCCGCCGAA
GlyValLeuA rgIleTyrLe uAspGlyAla TyrGlyIleG lyLysThrTh rAlaAlaGlu

       250        260        270
GAATTTTTAC ACCACTTTGC AATAACACCA AACCGG
GluPheLeuH isHisPheAl aIleThrPro AsnArg
```

FIG. 8

Sequences flanking the junction of the human AFP E/P to the VZV TK sequences in pCR78. Sequences 1-73 are from the human AFP E/P. Sequences 93-228 are from VZV. The sequences between the two vertical lines are linker sequences. The AFP proximal promoter element is double underlined. The start of RNA transcription is marked by an asterisk (*). The BamH I site is underlined. The vertical line marks the junction between ALB and VZV sequences. The displayed VZV coding sequence is translated.

```
         10         20         30         40     *   50         60
GCATTGCCTG AAAAGAGTAT AAAAGAATTT CAGCATGATT TTCCATATTG TGCTTCCACC

         70         80         90        100        110        120
ACTGCCAATA ACA|CCGGATC GCAAGCTGAT CC|TACAATAA ACATGTCAAC GGATAAAACC
                                                  MetSerThrAspLysThr

        130        140        150        160        170        180
GATGTAAAAA TGGGCGTTTT GCGTATTTAT TTGGACGGGG CGTATGGAAT TGGAAAAACG
AspValLysM etGlyValLe uArgIleTyr LeuAspGlyA laTyrGlyIl eGlyLysThr

        190        200        210        220
ACCGCCGCCG AAGAATTTTT ACACCACTTT GCAATAACAC CAAACCGG
ThrAlaAlaG luGluPheLe uHisHisPhe AlaIleThrP roAsnArg
```

cos CEA1 map and sequence from Schrewe, et.al. Mol Cell Biol 10:2738,1990

FIG. 12A/1

```
             HindIII
-10695       aagct taaaacccaa tggattgaca acatcaagag ttggaacaag tggacatgga
        gatgttactt gtggaaattt agatgtgttc agctatcggg caggagaatc tgtgtcaaat
-10580  tccagcatgg ttcagaagaa tcaaaaagtg tcacagtcca aatgtcgaac agtgcagggg
        ataaaactgt ggtgcattca aactgaggga tattttggaa catgagaaag gaagggattg
-10460  ctgctgcaca gaacatggat gatctcacac atagagttga aagaaaggag tcaatcgcag
        aatagaaaat gatcactaat tccacctcta taaagtttcc aagaggaaaa cccaattctg
-10340  ctgctagaga tcagaatgga ggtgacctgt gccttgcaat ggctgtgagg gtcacgggag
        tgtcacttag tgcaggcaat gtgccgtatc ttaatctggg cagggctttc atgagcacat
-10220  aggaatgcag acattactgc tgtgttcatt ttacttcacc ggaaaagaag aataaaatca
        gccgggcgcg gtggctcacg cctgtaatcc cagcacttta gaaggctgag gtgggcagat
-10100  tacttgaggt caggagttca agaccaccct ggccaatatg gtgaaacccc ggctctacta
        aaaatacaaa aattagctgg gcatggtggt gcgcgcctgt aatcccagct actcgggagg
 -9980  ctgaggctgg acaattgctt ggacccagga agcagaggtt gcagtgagcc aagattgtgc
        cactgcactc cagcttgggc aacagagcca gactctgtaa aaaaaaaaaa aaaaaaaaaa
 -9860  aaaagaaaga aagaaaaaga aaagaaagta taaaatctct ttgggttaac aaaaaaagat
        ccacaaaaca aacaccagct cttatcaaac ttacacaact ctgccagaga acaggaaaca
 -9740  caaatactca ttaactcact tttgtggcaa taaaaccttc atgtcaaaag gagaccagga
        cacaatgagg aagtaaaact gcaggcccta cttgggtgca gagagggaaa atccacaaat
 -9620  aaaacattac cagaaggagc taagatttac tgcattgagt tcattcccca ggtatgcaag
        gtgattttaa cacctgaaaa tcaatcattg cctttactac atagacagat tagctagaaa
 -9500  aaaattacaa ctagcagaac agaagcaatt tggccttcct aaaattccac atcatatcat
        catgatggag acagtgcaga cgccaatgac aataaaaaga gggacctccg tcacccggta
 -9380  aacatgtcca cacagctcca gcaagcaccc gtcttcccag tgaatcactg taacctcccc
        tttaatcagc cccaggcaag gctgcctgcg atggccacac aggctccaac ccgtgggcct
 -9260  caacctcccg cagaggctct cctttggcca ccccatgggg agagcatgag gacagggcag
        agccctctga tgcccacaca tggcaggagc tgacgccaga gccatggggg ctggagagca
 -9140  gagctgctgg ggtcagagct tcctgaggac acccaggcct aagggaaggc agctccctgg
        atgggggcaa ccaggctccg ggctccaacc tcagagcccg catgggagga gccagcactc
 -9020  taggcctttc ctagggtgac tctgagggga ccctgacacg acaggatcgc tgaatgcacc
        cgagatgaag gggccaccac gggaccctgc tctcgtggca gatcaggaga gagtgggaca
```

FIG. 12A/2

```
-8900  ccatgccagg cccccatggc atggctgcga ctgacccagg ccactcccct gcatgcatca
       gcctcggtaa gtcacatgac caagcccagg accaatgtgg aaggaaggaa acagcatccc
-8780  ctttagtgat ggaacccaag gtcagtgcaa agagaggcca tgagcagtta ggaagggtgg
       tccaacctac agcacaaacc atcatctatc ataagtagaa gccctgctcc atgacccctg
                                                     Sst1
-8660  catttaaata aacgtttgtt aaatgagtca aattccctca ccatgagagc tcacctgtgt
       gtaggcccat cacacacaca aacacacaca cacacacaca cacacacaca cacacacaca
-8540  gggaaagtgc aggatcctgg acagcaccag gcaggcttca caggcagagc aaacagcgtg
       aatgacccat gcagtgccct gggccccatc agctcagaga ccctgtgagg gctgagatgg
-8420  ggctaggcag gggagagact tagagagggt ggggcctcca gggagggggc tgcagggagc
       tgggtactgc cctccaggga gggggctgca gggagctggg tactgccctc cagggagggg
-8300  gctgcaggga gctgggtact gccctccagg gagggggctg cagggagctg ggtactgccc
       tccagggagg gggctgcagg gagctgggta ctgccctcca gggaggcagg agcactgttc
-8180  ccaacagaga gcacatcttc ctgcagcagc tgcacagaca caggagcccc catgactgcc
       ctgggccagg gtgtggattc caaatttcgt gccccattgg gtgggacgga ggttgaccgt
-8060  gacatccaag gggcatctgt gattccaaac ttaaactact gtgcctacaa aataggaaat
       aaccctactt tttctactat ctcaaattcc ctaagcacaa gctagcaccc tttaaatcag
-7940  gaagttcagt cactcctggg gtcctcccat gcccccagtc tgacttgcag gtgcacaggg
       tggctgacat ctgtccttgc tcctcctctt ggctcaactg ccgcccctcc tgggggtgac
-7820  tgatggtcag gacaagggat cctagagctg gccccatgat tgacaggaag gcaggacttg
       gcctccattc tgaagactag gggtgtcaag agagctgggc atcccacaga gctgcacaag
-7700  atgacgcgga cagagggtga cacagggctc agggcttcag acgggtcggg aggctcagct
       gagagttcag ggacagacct gaggagcctc agtgggaaaa gaagcactga agtgggaagt
-7580  tctggaatgt tctggacaag cctgagtgct ctaaggaaat gctcccaccc cgatgtagcc
       tgcagcactg gacggtctgt gtacctcccc gctgcccatc ctctcacagc ccccgcctct
-7460  agggacacaa ctcctgccct aacatgcatc tttcctgtct cattccacac aaaagggcct
       ctggggtccc tgttctgcat tgcaaggagt ggaggtcacg ttcccacaga ccacccagca
-7340  acagggtcct atggaggtgc ggtcaggagg atcacacgtc cccccatgcc caggggactg
       actctggggg tgatggattg gcctggaggc cactggtccc ctctgtccct gaggggaatc
```

FIG. 12A/3

-7220 tgcaccctgg aggctgccac atccctcctg attctttcag ctgagggccc ttcttgaaat
cccagggagg actcaacccc cactgggaaa ggcccagtgt ggacggttcc acagcagccc
-7100 agctaaggcc cttggacaca gatcctgagt gagagaacct ttagggacac aggtgcacgg
ccatgtcccc agtgcccaca cagagcaggg gcatctggac cctgagtgtg tagctcccgc
-6980 gactgaaccc agcccttccc caatgacgtg accccctgggg tggctccagg tctccagtcc
atgccaccaa aatctccaga ttgagggtcc tcccttgagt ccctgatgcc tgtccaggag
-6860 ctgccccctg agcaaatcta gagtgcagag ggctgggatt gtggcagtaa aagcagccac
SstI
atttgtctca ggaaggaaag ggaggacatg agctccagga agggcgatgg cgtcctctag
-6740 tgggcgcctc ctgttaatga gcaaaaaggg gccaggagag ttgagagatc agggctggcc
ttggactaag gctcagatgg agaggactga ggtgcaaaga gggggctgaa gtaggggagt
-6620 ggtcgggaga gatgggagga gcaggtaagg ggaagcccca gggaggccgg gggagggtac
agcagagctc tccactcctc agcattgaca tttggggtgg tcgtgctagt ggggttctgt
-6500 aagttgtagg gtgttcagca ccatctgggg actctaccca ctaaatgcca gcaggactcc
ctccccaagc tctaacaacc aacaatgtct ccagactttc caaatgtccc ctggagagca
-6380 aaattgcttc tggcagaatc actgatctac gtcagtctct aaaagtgact catcagcgaa
atccttcacc tcttgggaga agaatcacaa gtgtgagagg ggtagaaact gcagacttca
-6260 aaatctttcc aaaagagttt tacttaatca gcagtttgat gtcccaggag aagatacatt
tagagtgttt agagttgatg ccacatggct gcctgtacct cacagcagga gcagagtggg
-6140 ttttccaagg gcctgtaacc acaactggaa tgacactcac tgggttacat tacaaagtgg
EcoRI
aatgtgggga attctgtaga ctttgggaag ggaaatgtat gacgtgagcc cacagcctaa
-6020 ggcagtggac agtccacttt gaggctctca ccatctagga gacatctcag ccatgaacat
agccacatct gtcattagaa aacatgtttt attaagagga aaaatctagg ctagaagtgc
-5900 tttatgctct tttttctctt tatgttcaaa ttcatatact tttagatcat tccttaaaga
agaatctatc cccctaagta aatgttatca ctgactggat agtgttggtg tctcactccc
-5780 aacccctgtg tggtgacagt gccctgcttc cccagccctg ggccctctct gattcctgag
agctttgggt gctccttcat taggaggaag agaggaaggg tgtttttaat attctcacca
-5660 ttcacccatc cacctcttag acactgggaa gaatcagttg cccactcttg gatttgatcc
tcgaattaat gacctctatt tctgtccctt gtccatttca acaatgtgac aggcctaaga

FIG. 12A/4

```
-5540 ggtgccttct ccatgtgatt tttgaggaga aggttctcaa gataagtttt ctcacacctc
      tttgaattac ctccacctgt gtccccatca ccattaccag cagcatttgg acccttttc
-5420 tgttagtcag atgctttcca cctcttgagg gtgtatactg tatgctctct acacaggaat
      atgcagagga aatagaaaaa gggaaatcgc attactattc agagagaaga agacctttat
-5300 gtgaatgaat gagagtctaa aatcctaaga gagcccatat aaaattatta ccagtgctaa
      aactacaaaa gttacactaa cagtaaacta gaataataaa acatgcatca cagttgctgg
-5180 taaagctaaa tcagatattt ttttcttaga aaaagcattc catgtgtgtt gcagtgatga
      caggagtgcc cttcagtcaa tatgctgcct gtaatttttg ttccctggca gaatgtattg
-5060 tcttttctcc ctttaaatct taaatgcaaa actaaaggca gctcctgggc cccctcccca
      aagtcagctg cctgcaacca gccccacgaa gagcagaggc ctgagcttcc ctggtcaaaa
-4940 taggggggcta gggagcttaa ccttgctcga taaagctgtg ttcccagaat gtcgctcctg
      ttcccagggg caccagcctg gagggtggtg agcctcactg gtggcctgat gcttaccttg
-4820 tgccctcaca ccagtggtca ctggaacctt gaacacttgg ctgtcgcccg gatctgcaga
      tgtcaagaac ttctggaagt caaattactg cccacttctc cagggcagat acctgtgaac
-4700 atccaaaacc atgccacaga accctgcctg gggtctacaa cacatatgga ctgtgagcac
      caagtccagc cctgaatctg tgaccacctg ccaagatgcc cctaactggg atccaccaat
-4580 cactgcacat ggcaggcagc gaggcttgga ggtgcttcgc cacaaggcag ccccaatttg
      ctgggagttt cttggcacct ggtagtggtg aggagccttg ggaccctcag gattactccc
-4460 cttaagcata gtggggaccc ttctgcatcc ccagcaggtg ccccgctctt cagagcctct
      ctctctgagg tttacccaga cccctgcacc aatgagacca tgctgaagcc tcagagagag
-4340 agatggagct ttgaccagga gccgctcttc cttgagggcc agggcaggga aagcaggagg
      cagcaccagg agtgggaaca ccagtgtcta agcccctgat gagaacaggg tggtctctcc
-4220 catatgccca taccaggcct gtgaacagaa tcctccttct gcagtgacaa tgtctgagag
      gacgacatgt ttcccagcct aacgtgcagc catgcccatc tacccactgc ctactgcagg
-4100 acagcaccaa cccaggagct gggaagctgg gagaagacat ggaataccca tggcttctca
      ccttcctcca gtccagtggg caccatttat gcctaggaca cccacctgcc ggccccaggc
-3980 tcttaagagt taggtcacct aggtgcctct gggaggccga ggcaggagaa ttgcttgaac
      ccgggaggca gaggttgcag tgagccgaga tcacaccact gcactccagc ctgggtgaca
-3860 gaatgagact ctgtctcaaa aaaaaagaga aagatagcat cagtggctac caagggctag
      gggcagggga aggtggagag ttaatgatta atagtatgaa gtttctatgt gagatgatga
```

FIG. 12A/5

```
-3740  aaatgttctg gaaaaaaaaa tatagtggtg aggatgtaga atattgtgaa tataattaac
       ggcatttaat tgtacactta acatgattaa tgtggcatat tttatcttat gtatttgact
-3620  acatccaaga aacactggga gagggaaagc ccaccatgta aaatacaccc accctaatca
       gatagtcctc attgtaccca ggtacaggcc cctcatgacc tgcacaggaa taactaagga
-3500  tttaaggaca tgaggcttcc cagccaactg caggtgcaca acataaatgt atctgcaaac
       agactgagag taaagctggg ggcacaaacc tcagcactgc caggacacac acccttctcg
-3380  tggattctga ctttatctga cccggcccac tgtccagatc ttgttgtggg attgggacaa
       gggaggtcat aaagcctgtc cccagggcac tctgtgtgag cacacgagac ctccccaccc
-3260  ccccaccgtt aggtctccac acatagatct gaccattagg cattgtgagg aggactctag
       cgcgggctca gggatcacac cagagaatca ggtacagaga ggaagacggg gctcgaggag
-3140  ctgatggatg acacagagca gggttcctgc agtccacagg tccagctcac cctggtgtag
       gtgccccatc cccctgatcc aggcatccct gacacagctc cctcccggag cctcctccca
-3020  ggtgacacat cagggtccct cactcaagct gtccagagag ggcagcacct tggacagcgc
       ccaccccact tcactcttcc tccctcacag ggctcagggc tcagggctca agtctcagaa
-2900  caaatggcag aggccagtga gcccagagat ggtgacaggg caatgatcca ggggcagctg
       cctgaaacgg gagcaggtga agccacagat gggagaagat ggttcaggaa gaaaaatcca
-2780  ggaatgggca ggagaggaga ggaggacaca ggctctgtgg ggctgcagcc caggatggga
       ctaagtgtga agacatctca gcaggtgagg ccaggtccca tgaacagaga agcagctccc
-2660  acctcccctg atgcacggac acacagagtg tgtggtgctg tgcccccaga gtcgggctct
       cctgttctgg tccccaggga gtgagaagtg aggttgactt gtccctgctc ctctctgcta
-2540  ccccaacatt caccttctcc tcatgcccct ctctctcaaa tatgatttgg atctatgtcc
       ccgcccaaat ctcatgtcaa attgtaaacc ccaatgttgg aggtggggcc ttgtgagaag
-2420  tgattggata atgcgggtgg attttctgct ttgatgctgt ttctgtgata gagatctcac
       atgatctggt tgtttaaaag tgtgtagcac ctctcccctc tctctctctc tctcttactc
-2300  atgctctgcc atgtaagacg ttcctgtttc cccttcaccg tccagaatga ttgtaagttt
       tctgaggcct ccccaggagc agaagccact atgcttcctg tacaactgca gaatgatgag
-2180  cgaattaaac ctcttttctt tataaattac ccagtctcag gtatttcttt atagcaatgc
       gaggacagac taatacaatc ttctactccc agatccccgc acacgcttag ccccagacat
```

FIG. 12A/6

```
-2060  cactgcccct gggagcatgc acagcgcagc ctcctgccga caaaagcaaa gtcacaaaag
       gtgacaaaaa tctgcatttg gggacatctg attgtgaaag agggaggaca gtacacttgt
-1940  agccacagag actggggctc accgagctga aacctggtag cactttggca taacatgtgc
       atgacccgtg ttcaatgtct agagatcagt gttgagtaaa acagcctggt ctggggccgc
-1820  tgctgtcccc acttccctcc tgtccaccag agggcggcag agttcctccc accctggagc
       ctccccaggg gctgctgacc tccctcagcc gggcccacag cccagcaggg tccaccctca
-1700  cccgggtcac ctcggcccac gtcctcctcg ccctccgagc tcctcacacg gactctgtca
       gctcctccct gcagcctatc ggccgcccac ctgaggcttg tcggccgccc acttgaggcc
-1580  tgtcggctgc cctctgcagg cagctcctgt cccctacacc ccctccttcc ccgggctcag
                                    ---------------------------->
       ctgaaagggc gtctcccagg gcagctccct gtgatctcca ggacagctca gtctctcaca
-1460  ggctccgacg ccccctatgc tgtcacctca cagccctgtc attaccatta actcctcagt
       cccatgaagt tcactgagcg cctgtctccc ggttacagga aaactctgtg acaggacca
-1340  cgtctgtcct gctctctgtg gaatcccagg gcccagccca gtgcctgaca cggaacagat
       gctccataaa tactggttaa atgtgtggga gatctctaaa aagaagcata tcacctccgt
-1220  gtggccccca gcagtcagag tctgttccat gtggacacag gggcactggc accagcatgg
       gaggaggcca gcaagtgccc gcggctgccc caggaatgag gcctcaaccc ccagagcttc
-1100  agaagggagg acagaggcct gcagggaata gatcctccgg cctgaccctg cagcctaatc
       cagagttcag ggtcagctca caccacgtcg accctggtca gcatccctag ggcagttcca
                                               <---------------------
-980   gacaaggccg gaggtctcct cttgccctcc aggggtgac attgcacaca gacatcactc
       ------
       aggaaacgga ttcccctgga caggaacctg gctttgctaa ggaagtggag gtggagcctg
-860   gtttccatcc cttgctccaa cagacccttc tgatctctcc cacatacctg ctctgttcct
       ttctgggtcc tatgaggacc ctgttctgcc aggggtccct gtgcaactcc agactccctc
-740   ctggtaccac catggggaag gtggggtgat cacaggacag tcagcctcgc agagacagag
       accacccagg actgtcaggg agaacatgga caggccctga gccgcagctc agccaacaga
-620   cacggagagg gagggtcccc ctggagcctt ccccaaggac agcagagccc agagtcaccc
       acctccctcc accacagtcc tctctttcca ggacacacaa gacacctccc cctccacatg
```

FIG. 12A/7

```
-500   caggatctgg ggactcctga gacctctggg cctgggtctc catccctggg tcagtggcgg
       ggttggtggt actggagaca gagggctggt ccctccccag ccaccaccca gtgagccttt
-380   ttctagcccc cagagccacc tctgtcacct tcctgttggg catcatccca ccttcccaga
                              SmaI
       gccctggaga gcatggggag acccgggacc ctgctgggtt tctctgtcac aaaggaaaat
-260   aatcccccctg gtgtgacaga cccaaggaca gaacacagca gaggtcagca ctggggaaga
       caggttgtcc tcccagggga tgggggtcca tccaccttgc cgaaaagatt tgtctgagga
-140   actgaaaata gaagggaaaa aagaggaggg acaaaagagg cagaaatgag aggggagggg
                                                                ScaI
       acagaggaca cctgaataaa gaccacaccc atgacccacg tgatgctgag aagtactcct
-020   gccctaggaa gagactcagg gcagagggag gaaggacagc agaccagaca gtcacagcag
                                          •
       ccttgacaaa acgttcctgg aactcaagct cttctccaca gaggaggaca gagcagacag
+100   cagagaccat ggagtctccc tcggcccctc cccacagatg gtgcatcccc tggcagaggc
               Me tGluSerPro SerAlaProP roHisArgTr pCysIlePro TrpGlnArgL
       tcctgctcac aggtgaaggg aggacaacct gggagagggt gggaggaggg agctggggtc
       euLeuLeuTh r
+220   tcctgggtag gacagggctg tgagacggac agagggctcc tgttggagcc tgaataggga
       agaggacatc agagagggac aggagtcaca ccagaaaaat caaattgaac tggaattgga
+340   aaggggcagg aaaacctcaa gagttctatt ttcctagtta attgtcactg gccactacgt
       ttttaaaaat cataataact gcatcagatg acactttaaa taaaaacata accaggcat
+460   gaaacactgt cctcatccgc ctaccgcgga cattggaaaa taagccccag gctgtggagg
       gccctgggaa ccctcatgaa ctcatccaca ggaatctgca gcctgtccca ggcactgggg
               Sau3A
+580   tgcaaccaag atc  592
```

FIG. 12B/1

```
-14463        aagcttttagtgctttagacagtgagctggtctgtctaacccaagtgacctg
-14410  ggctccatactcagccccagaagtgaagggtgaagctgggtggagccaaaccaggcaagc
-14350  ctaccctcagggctcccagtggcctgagaaccattggacccaggacccattacttctagg
-14290  gtaaggaaggtacaaacaccagatccaaccatggtctgggggacagctgtcaaatgcct
-14230  aaaaatatacctgggagaggagcaggcaaactatcactgccccaggttctctgaacagaa
-14170  acagaggggcaacccaaagtccaaatccaggtgagcaggtgcaccaaatgcccagagata
-14110  tgacgaggcaagaagtgaaggaaccacccctgcatcaaatgttttgcatgggaaggagaa
-14050  ggggttgctcatgttcccaatccaggagaatgcatttgggatctgccttcttctcactc
-13990  cttggttagcaagactaagcaaccaggactctggatttggggaaagacgtttatttgtgg
-13930  aggccagtgatgacaatcccacgagggcctaggtgaagagggcaggaaggctcgagacac
-13870  tggggactgagtgaaaaccacacccatgatctgcaccacccatggatgctccttcattgc
-13810  tcacctttctgttgatatcagatggccccatttctgtaccttcacagaaggacacaggc
-13750  tagggtctgtgcatggccttcatccccggggccatgtgaggacagcaggtgggaaagatc
-13690  atgggtcctcctgggtcctgcagggccagaacattcatcacccatactgacctcctagat
-13630  gggaatggcttccctggggctgggccaacggggcctgggcaggggagaaaggacgtcagg
-13570  ggacagggaggaagggtcatcgagacccagcctggaaggttcttgtctctgaccatccag
-13510  gatttacttccctgcatctacctttggtcattttccctcagcaatgaccagctctgcttc
-13450  ctgatctcagcctcccaccctggacacagcaccccagtccctggcccggctgcatccacc
-13390  caataccctgataacccaggacccattacttctagggtaaggagggtccaggagacagaa
-13330  gctgaggaaaggtctgaagaagtcacatctgtcctggccagaggggaaaaaccatcagat
-13270  gctgaaccaggagaatgttgacccaggaaagggaccgaggacccaagaaaggagtcagac
-13210  caccagggtttgcctgagaggaaggatcaaggccccgagggaaagcagggctggctgcat
-13150  gtgcaggacactggtggggcatatgtgtcttagattctccctgaattcagtgtccctgcc
-13090  atggccagactctctactcaggcctggacatgctgaaataggacaatggccttgtcctct
-13030  ctccccaccatttggcaagagacataaaggacattccaggacatgccttcctgggaggtc
-12970  caggttctctgtctcacacctcagggactgtagttactgcatcagccatggtaggtgctg
-12910  atctcacccagcctgtccaggcccttccactctccactttgtgaccatgtccaggaccac
-12850  ccctcagatcctgagcctgcaaatacccccttgctgggtgggtggattcagtaaacagtg
-12790  agctcctatccagcccccagagccacctctgtcaccttcctgctgggcatcatcccacct
-12730  tcacaagcactaaagagcatggggagacctggctagctgggtttctgcatcacaaagaaa
-12670  ataatcccccaggttcggattcccagggctctgtatgtggagctgacagacctgaggcca
-12610  ggagatagcagaggtcagccctagggagggtgggtcatccacccaggggacaggggtgca
```

FIG. 12B/2

```
-12550  ccagccttgctactgaaagggcctccccaggacagcgccatcagccctgcctgagagctt
-12490  tgctaaacagcagtcagaggaggccatggcagtggctgagctcctgctccaggccccaac
-12430  agaccagaccaacagcacaatgcagtccttccccaacgtcacaggtcaccaaagggaaac
-12370  tgaggtgctacctaaccttagagccatcaggggagataacagcccaatttcccaaacagg
-12310  ccagtttcaatcccatgacaatgacctctctgctctcattcttcccaaaataggacgctg
-12250  attctcccccaccatggatttctcccttgtcccgggagccttttctgccccctatgatct
-12190  gggcactcctgacacacacctcctctctggtgacatatcagggtccctcactgtcaagca
-12130  gtccagaaaggacagaaccttggacagcgcccatctcagcttcacccttcctccttcaca
-12070  gggttcagggcaaagaataaatggcagaggccagtgagcccagagatggtgacaggcagt
-12010  gacccaggggcagatgcctggagcaggagctggcggggccacagggagaaggtgatgcag
-11950  gaagggaaacccagaaatgggcaggaaaggaggacacaggctctgtggggctgcagccca
-11890  gggttggactatgagtgtgaagccatctcagcaagtaaggccaggtcccatgaacaagag
-11830  tgggagcacgtggcttcctgctctgtatatggggtggggattccatgccccatagaacc
-11770  agatggccggggttcagatggagaaggagcaggacaggggatccccaggataggaggacc
-11710  ccagtgtccccacccaggcaggtgactgatgaatgggcatgcagggtcctcctgggctgg
-11650  gctctccctttgtccctcaggattccttgaaggaacatccggaagccgaccacatctacc
-11590  tggtgggttctggggagtccatgtaaagccaggagcttgtgttgctaggaggggtcatgg
-11530  catgtgctgggggcaccaaagagagaaacctgagggcaggcaggacctggtctgaggagg
-11470  catgggagcccagatggggagatggatgtcaggaaaggctgccccatcagggagggtgat
-11410  agcaatggggggtctgtgggagtgggcacgtgggattccctgggctctgccaagttccct
-11350  cccatagtcacaacctggggacactgcccatgaagggcgcctttgcccagccagatgct
-11290  gctggttctgcccatccactaccctctctgctccagccactctgggtctttctccagatg
-11230  ccctggacagccctggcctgggcctgtcccctgagaggtgttgggagaagctgagtctct
-11170  ggggacactctcatcagagtctgaaaggcacatcaggaaacatccctggtctccaggact
-11110  aggcaatgaggaaagggccccagctcctccctttgccactgagagggtcgaccctgggtg
-11050  gccacagtgacttctgcgtctgtcccatgcaccctgaaaccacaacaaaaccccagcccc
-10990  agaccctgcaggtacaatacatgtggggacagtctgtacccaggggaagccagttctctc
-10930  ttcctaggagaccgggcctcagggctgtgcccggggcaggcgggggcagcacgtgcctgt
-10870  ccttgagaactcgggaccttaagggtctctgctctgtgaggcacagcaaggatccttctg
-10810  tccagagatgaaagcagctcctgcccctcctctgacctcttcctccttcccaaatctcaa
-10750  ccaacaaataggtgtttcaaatctcatcatcaaatcttcatccatccacatgagaaagct
-10690  t
```

FIG. 14B

| Plasmid | CEA Coordinates |
|---|---|
| pCR113 | (-299 to +69) |
| pCR105 | (-1664 to +69) |
| pCR145 | (-14462 to –10691) + (-299 to +69) |
| pCR148 | (-89 to –40) + (-90 to +69) |
| pCR158 | [3X (-89 to –40)] + (-90 to+69) |
| pCR136 | (-3919 to –6071) + (-299 to +69) |
| pCR137 | (-6071 to –3919) + (-299 to +69) |
| pCR162 | (-13579 to –10691) + (-89 to –40) + (-90 to +69) |
| pCR163 | (-10691 to –13579) + (-89 to –40) + (-90 to +69) |

| Chromosomal Mutation | Growth Patterns | | | |
|---|---|---|---|---|
| | Cytosine | 5-FC | 5-FU | Uracil |
| *codA* (Cytosine deaminase, 11) | + | + | - | + |
| *pyrF* (OMP decarboxylase, 6) | + | - | - | + |
| *codA, pyrF* | - | + | - | + |
| wild-type | + | - | - | + |

| Plasmid[a] | Cytosine Phenotype[b] | Cytosine Specific Activity[c] | | 5-Fluorocytosine Phenotype | 5-Fluorocytosine Specific Activity | |
|---|---|---|---|---|---|---|
| | | MG | 1890 | | MG | 29 |
| pEA002 | + | LB | 555 | - | LB | 15 |
| | | MG | 3919 | | MG | 46 |
| pEA001 | + | LB | 1618 | - | LB | 36 |
| | | MG | 2043 | | MG | 36 |
| pEA003 | + | LB | 584 | - | LB | 15 |
| | | MG | 0 | | MG | 0 |
| pEA004 | - | LB | 0 | + | LB | 0 |
| | | MG | 0 | | MG | 0 |
| pEA005 | - | LB | 0 | + | LB | 0 |
| | | MG | 17407 | | MG | 264 |
| pEA006 | + | LB | 4914 | - | LB | 9 |
| | | MG | 0 | | MG | 0 |
| pEA007 | - | LB | 0 | + | LB | 0 |
| | | MG | 16 | | MG | B.T. |
| pEA009 | + | LB | 19 | - | LB | B.T. |
| | | MG | 0 | | MG | 0 |
| pEA010 | - | LB | 0 | + | LB | 0 |
| | | MG | 8 | | MG | B.T. |
| pEA013 | + | LB | 20 | - | LB | B.T. |
| | | MG | 0 | | MG | 0 |
| pEA014 | - | LB | 0 | + | LB | 0 |

FIG. 21/1

```
PstI         BstEII
ctgcaggcca ctggttaccg ggaattgttc cggtcaacgc ggtattaggt ggcgcgctga gctatctgat ccttaacccg attttgaatc   90

                                                                                BstEII
gtaaaacgac agcagcaatg acgcatgtgg aggctaacag tgtcgaataa cgctttacaa acaattatta acgcccggtt accaggcgaa  180
                                           V alSerAsnAs nAlaLeuGln ThrIleIleA snAlaArgLe uProGlyGlu

                         PstI
gaggggctgt ggcagattca tctgcaggac ggaaaaatca gcgccattga tgcgcaatcc ggcgtgatgc ccataactga aaacagcctg  270
GluGlyLeuT rpGlnIleHi sLeuGlnAsp GlyLysIleS erAlaIleAs pAlaGlnSer GlyValMetP roIleThrGl uAsnSerLeu

gatgccgaac aaggtttagt tataccgccg tttgtggagc cacatattca cctggacacc acgcaaaccg ccggacaacc gaactggaat  360
AspAlaGluG lnGlyLeuVa lIleProPro PheValGluP roHisIleHi sLeuAspThr ThrGlnThrA laGlyGlnPr oAsnTrpAsn

cagtccggca cgctgtttga aggcattgaa cgctgggccg agcgcaaagc gttattaacc catgacgatg tgaaacaacg cgcatggcaa  450
GlnSerGlyT hrLeuPheGl uGlyIleGlu ArgTrpAlaG luArgLysAl aLeuLeuThr HisAspAspV alLysGlnAr gAlaTrpGln

acgctgaaat ggcagattgc caacggcatt cagcatgtgc gtacccatgt cgatgtttcg gatgcaacgc taactgcgct gaaagcaatg  540
ThrLeuLysT rpGlnIleAl aAsnGlyIle GlnHisValA rgThrHisVa lAspValSer AspAlaThrL euThrAlaLe uLysAlaMet

ctggaagtga agcaggaagt cgcgccgtgg attgatctgc aaatcgtcgc cttccctcag gaagggattt tgtcgtatcc caacggtgaa  630
LeuGluValL ysGlnGluVa lAlaProTrp IleAspLeuG lnIleValAl aPheProGln GluGlyIleL euSerTyrPr oAsnGlyGlu

gcgttgctgg aagaggcgtt acgcttaggg gcagatgtag tgggggcgat tccgcatttt gaatttaccc gtgaatacgg cgtggagtcg  720
AlaLeuLeuG luGluAlaLe uArgLeuGly AlaAspValV alGlyAlaIl eProHisPhe GluPheThrA rgGluTyrGl yValGluSer

                                                                ClaI
ctgcataaaa ccttcgccct ggcgcaaaaa tacgaccgtc tcatcgacgt tcactgtgat gagatcgatg acgagcagtc gcgctttgtc  810
LeuHisLysT hrPheAlaLe uAlaGlnLys TyrAspArgL euIleAspVa lHisCysAsp GluIleAspA spGluGlnSe rArgPheVal
```

FIG. 21/2

```
gaaaccgttg ctgccctggc gcaccatgaa ggcatgggcg cgcgagtcac cgccagccac accacggcaa tgcactccta taacggggcg  900
GluThrValA laAlaLeuAl aHisHisGlu GlyMetGlyA laArgValTh rAlaSerHis ThrThrAlaM etHisSerTy rAsnGlyAla

tatacctcac gcctgttccg cttgctgaaa atgtccggta ttaactttgt cgccaacccg ctggtcaata ttcatctgca aggacgtttc  990
TyrThrSerA rgLeuPheAr gLeuLeuLys MetSerGlyI leAsnPheVa lAlaAsnPro LeuValAsnI leHisLeuGl nGlyArgPhe

  SnaBI
gatacgtatc caaaacgtcg cggcatcacg cgcgttaaag agatgctgga gtccggcatt aacgtctgct ttggtcacga tgatgtcttc 1080
AspThrTyrP roLysArgAr gGlyIleThr ArgValLysG luMetLeuGl uSerGlyIle AsnValCysP heGlyHisAs pAspValPhe

gatccgtggt atccgctggg aacggcgaat atgctgcaag tgctgcatat ggggctgcat gtttgccagt tgatgggcta cgggcagatt 1170
AspProTrpT yrProLeuGl yThrAlaAsn MetLeuGlnV alLeuHisMe tGlyLeuHis ValCysGlnL euMetGlyTy rGlyGlnIle

aacgatggcc tgaatttaat cacccaccac agcgcaagga cgttgaattt gcaggattac ggcattgccg ccggaaacag cgccaacctg 1260
AsnAspGlyL euAsnLeuIl eThrHisHis SerAlaArgT hrLeuAsnLe uGlnAspTyr GlyIleAlaA laGlyAsnSe rAlaAsnLeu

attatcctgc cggctgaaaa tgggtttgat gcgctgcgcc gtcaggttcc ggtacgttat tcggtacgtg gcggcaaggt gattgccagc 1350
IleIleLeuP roAlaGluAs nGlyPheAsp AlaLeuArgA rgGlnValPr oValArgTyr SerValArgG lyGlyLysVa lIleAlaSer

                                             ClaI
acacaaccgg cacaaaccac cgtatatctg gagcagccag aagccatcga ttacaaacgt tgaacgactg ggttacagcg agcttagttt 1440
ThrGlnProA laGlnThrTh rValTyrLeu GluGlnProG luAlaIleAs pTyrLysArt ...

                                  SnaBI
atgccggatg cggcgtgaac gccttatccg gcctacgtag agcactgaac tcgtaggcct gataagcgta gcgcatcagg caattccagc 1530

cgctgatctg tgtcagcggc taccgtgatt cattcccgcc aacaaccgcg cattcctcca acgccatgtg caaaaatgcc ttcgcagcgg 1620

        PvuII
ctgtctgcca gctg  1634
```

MOLECULAR CONSTRUCTS COMPRISING A CARCINOEMBRYONIC ANTIGEN (CEA) TRANSCRIPTIONAL REGULATORY REGION

CROSS REFERENCE TO RELATED APPLICATIONS

This is a continuation of copending application Ser. No. 08/154,712 filed on Nov. 19, 1993.

This application is a continuation-in-part of U.S. application Ser. No. 07/841,961 filed Feb. 26, 1992 which is a continuation-in-part of U.S. application Ser. No. 07/662,222 filed Feb. 22, 1991 which is a continution-in-part of U.S application Ser. No. 07/574,994 filed Sep. 27, 1990 all abandoned.

FIELD OF THE INVENTION

The present invention relates to molecular chimaeras in infective virions: methods of their construction; pharmaceutical formulations containing them; their use in therapy, particularly virus-directed enzyme prodrug therapy, particularly in the treatment of cancers, and more particularly in the treatment of hepatocellular and colorectal carcinomas; and the use of agents which can be catalysed by a heterologous enzyme to cytotoxic or cytostatic metabolites, such as purine arabinosides and substituted pyrimidines and cytosines in virus-directed enzyme prodrug therapy in a host(e.g., mammal or human).

BACKGROUND OF THE INVENTION

Cancer of all forms is one of the major causes of morbidity throughout the world. Research in cancer chemotherapy has produced a variety of antitumour agents with differing degrees of efficacy. Standard clinically used agents include adriamycin, actinomycin D, methotrexate, 5-fluorouracil, cisplatin, vincristine and vinblastine. However, these presently available antitumour agents are known to have various disadvantages such as toxicity to healthy cells and resistance of certain tumour types. Other forms of therapy, such as surgery, are known. However it is appreciated by those skilled in the art that novel approaches and entities for cancer therapy are still needed.

Hepatocellular carcinoma (HCC) is one of the major malignant diseases in the world today; the greatest incidence being in Japan, China, other parts of Asia, and sub-Saharan Africa. Recent evidence suggests that the incidence of hepatocellular carcinoma in Europe and North America is increasing. The disease is estimated to be responsible for or involved in up to approximately 1,250,000 deaths a year, making it one of the world's major malignant diseases.

The prognosis of HCC is always poor, with the worldwide frequency rate almost equalling the mortality rate. After diagnosis, the median survival time is less than four months. Long-term survival, defined as survival longer than one year after diagnosis, is seen only occasionally. Most HCC patients succumb to either the complications of liver failure with or without massive bleeding, or to the general effects of a large tumour burden, with cachexia, malnutrition, infection, and sepsis. Though distant metastases occur (up to 90% of patients have metastatic tumour at time of death), regional disease most often limits survival. Consequently, therapies directed toward control of hepatic tumours are appropriate, although it will be appreciated that treatment of the metastatic disease is also of great importance(Kew M. C. Postgrad. Med. J. 5 (Suppl. 4) 78–87 (1983) and Berk P. (Ed) Semin. Liver Dis. 4, No.2, Thieme-Stratton Inc. N.Y. (1 984)).

Current therapies available to the clinician are basically ineffective as a curative treatment for this disease (Nerenstone S. R., Ihde D. C., Friedman M. A. Cancer Treat. Rev. 15, 1–31 (1988)). To date, surgery continues to be the only potentially curative treatment. However, at the time of diagnosis, the overwhelming majority of patients are not able to undergo radical surgery. In certain studies (Nerenstone et al supra) less than 3% of patients were considered capable of undergoing surgery and of the small percentage that do undergo surgery, approximately 50% suffer from postoperative morbidity (Nerenstone et al supra).

Colorectal carcinoma(CRC) is the second most frequent cancer and the second leading cause of cancer-associated deaths in the United States and Western Europe(Silverberg, E. CA 33, 9–25(1983); Silverberg, E. CA 36, 9–25(1986); Farley, P. C., and McFaden, K. H. Postgrad. Med. 84, 175–183)(1988). The overall five-year survival rate for patients has not meaningfully improved in the last three decades. Prognosis for the CRC cancer patient is associated with the depth of tumor penetration into the bowel wall, the presense of regional lymph node involvement and, most importantly, the presense of distant metastases. The liver is the most common site for distant metastasis and, in approximately 30% of patients, the sole initial site of tumor recurrence after successful resection of the primary colon cancer (Daly, J. M., and Kemeny, N. Import. Adv. Oncol. 251–286 (1986) ). Hepatic metastases are the most common cause of death in the CRC cancer patient(Swinton, N. W., et al., Dis. Colon Rectum 7, 273–277(1964) ).

The treatment of choice for the majority of patients with hepatic CRC metastasis is systemic or regional chemotherapy using 5-fluorouracil(5-FU) alone or in combination with other agents such as leviamasole(for a review see Daly, J. M., and Kemeny, N. (1986) Import. Adv. Oncol.251–286). However, despite extensive effort, there is still no satisfactory treatment for hepatic CRC metastasis.

Systemic single- and combination-agent chemotherapy and radiation are relatively ineffective emphasizing the need for new approaches and therapies for the treatment of these diseases.

BRIEF DESCRIPTION OF THE FIGURES

FIG. 1: Schematic representation of albumin transcriptional regulatory sequences(TRS) in relation to the albumin gene (1A), and a heterologous gene (1B). The truncated albumin TRS in relation to a heterologous gene(1C).

FIG. 2B: VZV TK gene—$1^0$ sequence(SEQ ID NO:1) and amino acid sequence (SEQ ID NO:11)

FIG. 4A: Proviral form of retrovirus containing alpha-fetoprotein/VZV TK molecular chimaera.

FIG. 4B: pCR78.

FIG. 7: Sequence flanking ALB E/P to VZV TK in pCR74(SEQ ID NO:2). E=Enhancer, P=Promoter. Partial amino acid sequence of VZV TK shown (SEQ ID NO:12).

FIG. 8: Sequence flanking AFP E/P to VZV TK in pCR78(SEQ ID NO:3). E=Enhancer, P=Promoter. Partial amino acid sequence of VZV TK shown (SEQ ID NO:13).

FIG. 12A: DNA sequence of the 11,288 bp HindIII to Sau3A fragment of lambda CEA7(SEQ ID NO:4). Sequence is numbered with the approximate transcription initation point for CEA mRNA as 0(this start site is approximate because there is some slight variability in the start site among indiviual CEA transcripts). The translation of the first exon is shown (SEQ ID NO:14). Intron 1 extends from +172 to beyond +592. Several restriction sites are shown above the sequence. In subclone 109-3 the sequence at positions +70 has been altered by site-directed mutagenesis in order to introduce HindIII and EcoRI restriction sites.

FIG. 12B: DNA sequence of the 3774 bp Hind III to Hind III fragment of lambda CEA7(SEQ ID NO:5). Sequence is numbered as in FIG. 12A.

Consensus sequence A1(SEQ ID NO:16), A2calt (SEQ ID NO:17), A4alt (SEQ ID NO:18), B2 (SEQ ID NO:19), B4 (SEQ ID NO:20), B12 (SEQ ID NO:21), B15 (SEQ ID NO:22), B17 (SEQ ID NO:23), B18 (SEQ ID NO:24), C5 (SEQ ID NO:25), D9 (SEQ ID NO:26), E5 SEQ ID NO:27), F2 (SEQ ID NO:28), F6 (SEQ ID NO:29), F7 (SEQ ID NO:30), F9 (SEQ ID NO:31), F10 (SEQ ID NO:32), G2 (SEQ ID NO:33), G7 (SEQ ID NO:34), H1 (SEQ ID NO:35), and a sequence that is 90% H1 (SEQ ID NO:36).

Figure 13:
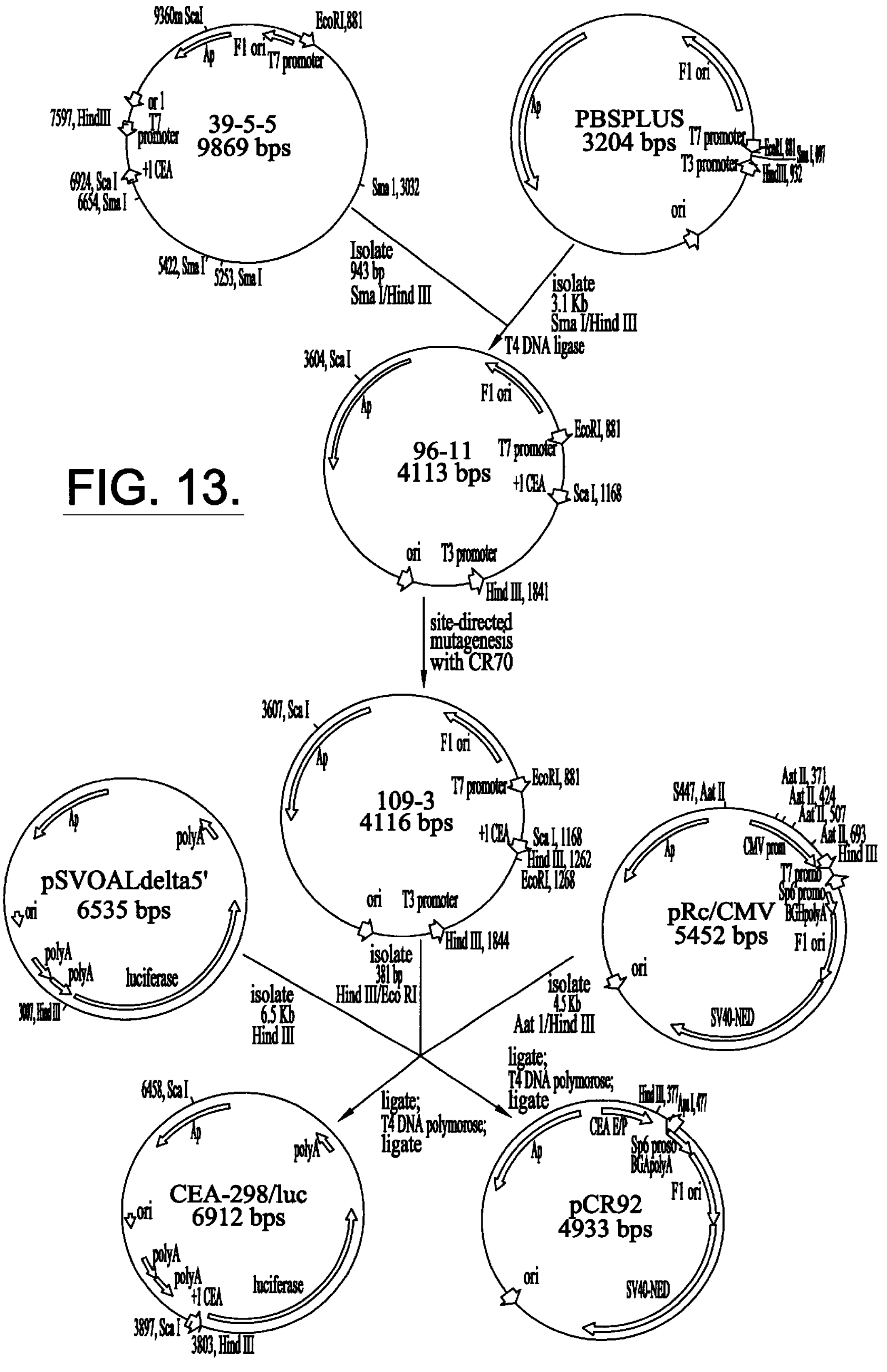

FIG. 13: Cloning scheme for CEA constructs extending from −299 bp to +69 bp.

Figure 14A:
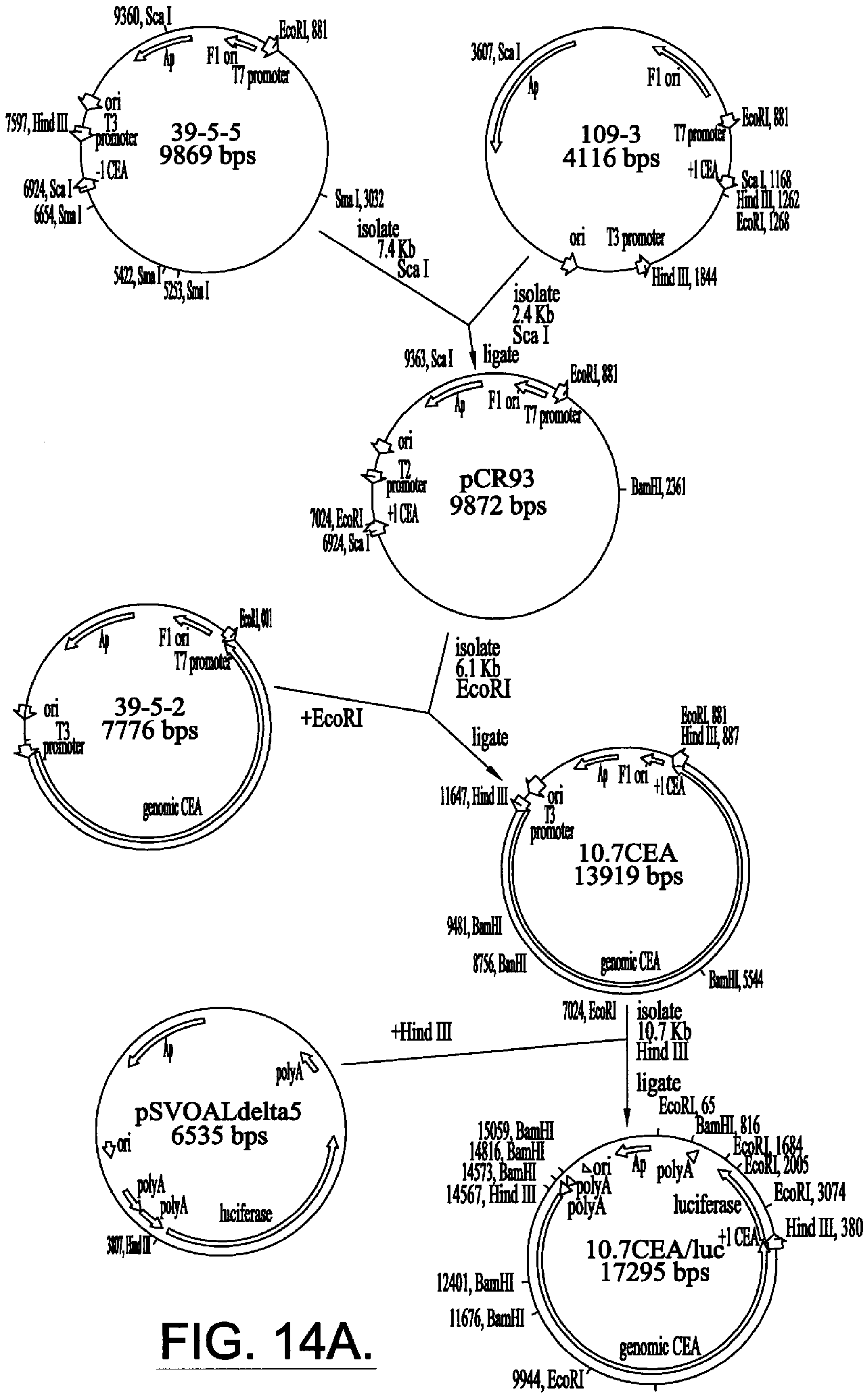

FIG. 14A: Cloning scheme for CEA constructs extending from −10.7 kb to +69 bp.

FIG. 14B: Coordinates for CEA sequence present in several CEA/luciferase clones. CEA sequences were cloned into the multiple cloning region of pGL2-Basic (Promega Corp.) by standard techniques. CEA coordinates determined using base numbering of FIGS. 12A and 12B.

Figure 14C:
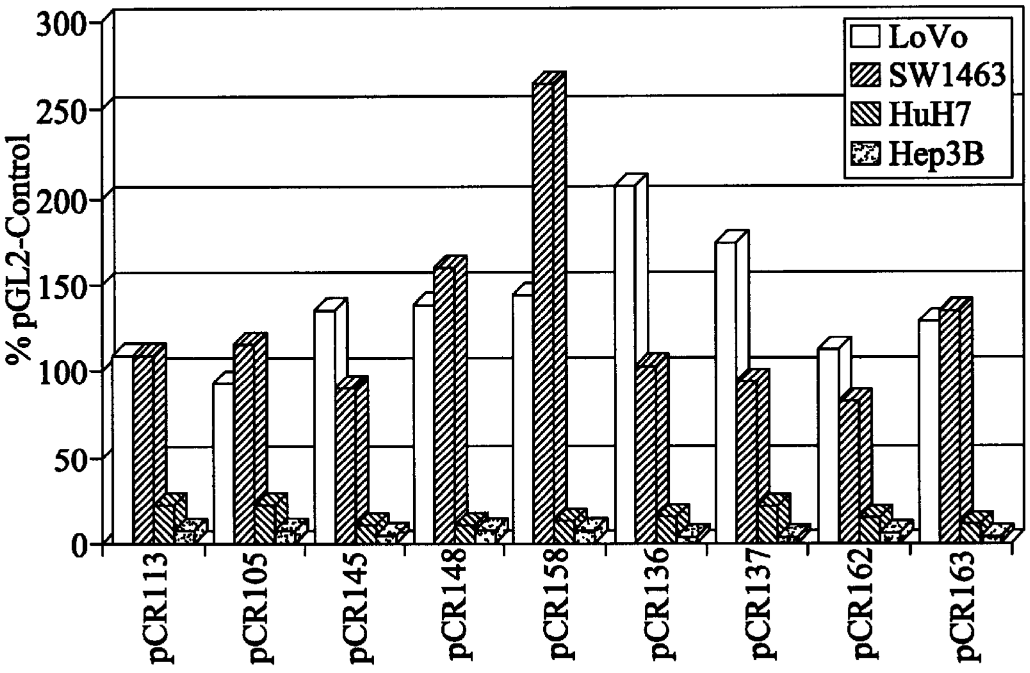
Figure 14D:
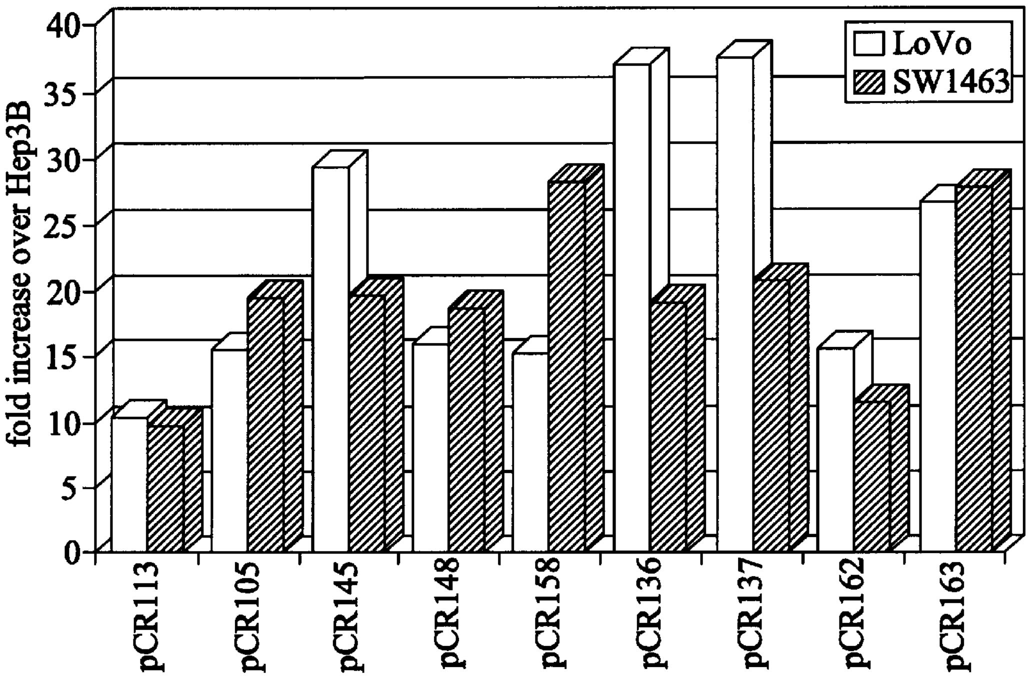

FIGS. 14C: Transient luciferase assays. Transient and 14D transfections and luciferase assays were performed in quadruplicate by standard techniques using DOTAP (Boehringer Mannheim, Indianpolis, Ind.), luciferase assay system (Promega, Madison, Wis.), and Dynatech luminometer (Chantilly, Va.). CEA-positive cell lines included LoVo (ATCC #CCL 229) and SW1463 (ATCC #CCL 234). CEA-negative cell lines included HuH7 and Hep3B (ATCC #HB 8064). C. Luciferase activity expressed as the percent of pGL2-Control plasmid activity. D. Luciferase activities of LoVo and SW1463 expressed as fold increase over activity in Hep3B.

Figures 15A, 15B:
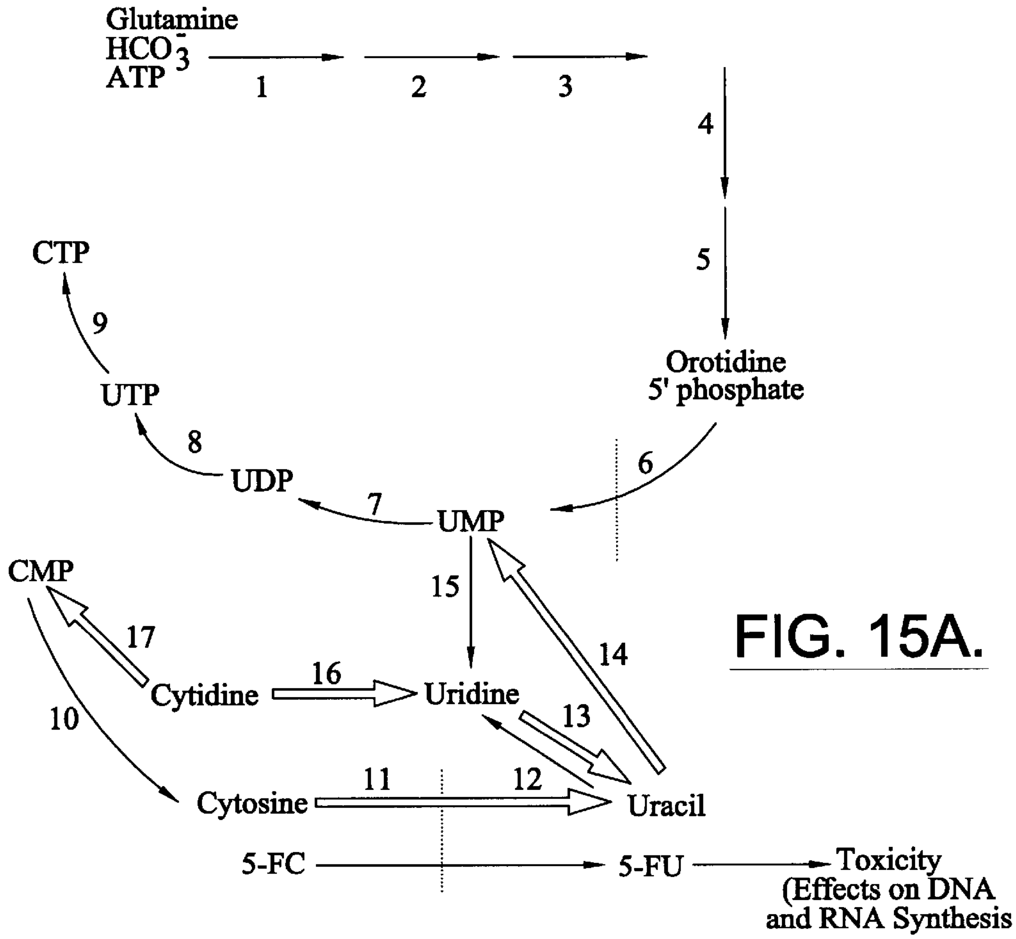

FIG. 15A: An illustration of the de novo pyrimidine and the salvage pyrimidine pathways of *E. coli*. The enzymes involved at each step are indicated by numbers: 1, carbamoylphosphate synthase; 2, aspartate carbamoyltransferase; 3, dihydroorotase; 4, dihydroorotate oxidase; 5, orotate phosphoribosyltransferase; 6, orotidine 5'-phosphate decarboxylase; 7, UMP kinase; 8, nucleoside diphospho-kinase; 9, CTP synthetase; 10, ribonucleotide glycosylase; 11, cytosine deaminase; 12, 13, uridine phosphorylase; 14, uracil phosphoribosyltransferase; 15, uridine kinase; 16, cytidine deaminase.

FIG. 15B: The growth characteristics of relevant bacterial strains illustrating the basis for the selection scheme described in the text. *E. coli* strains carrying a mutation in codA, the gene encoding CD, are unable to metabolize cytosine. A strain carring a mutation, such as pyrF, in the pyrimidine de novo pathway is dependent on an external source of pyrimidines. The presence of both mutations results in a strain that is unable to utilize cytosine as the sole pyrimidine source unless the gene encoding CD is provided in trans.

Figure 16A:
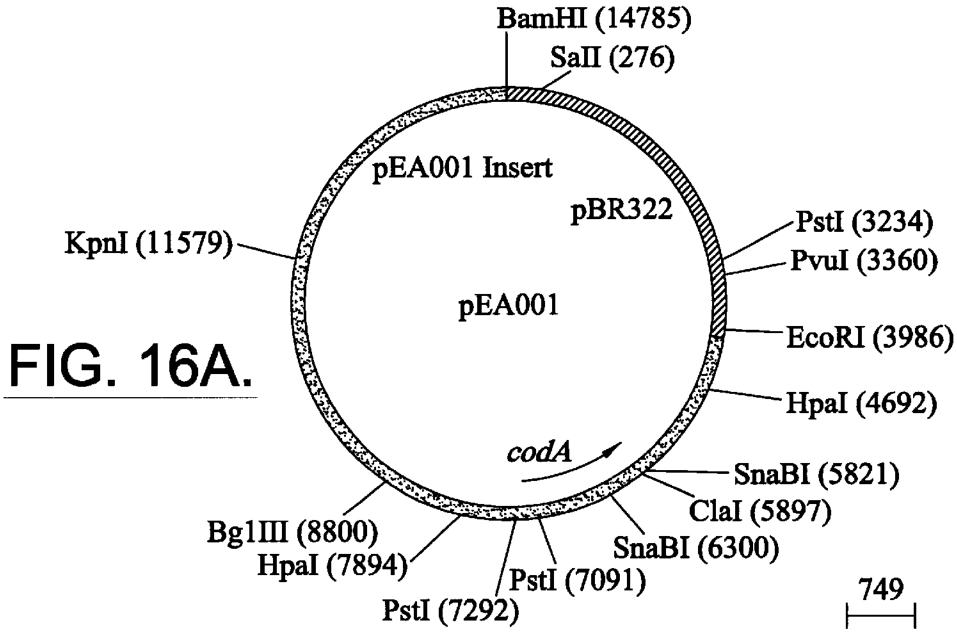
Figure 16B:
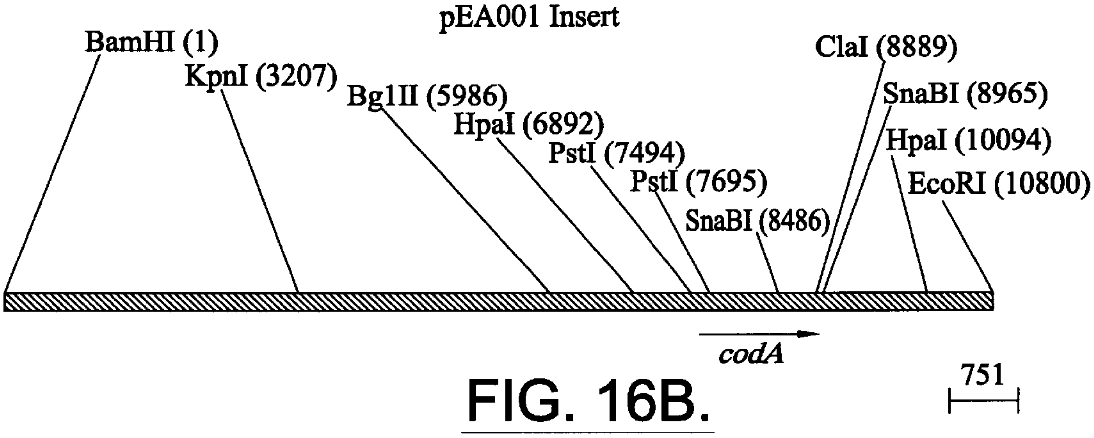

FIG. 16: Restriction map of the plasmid pEA00 1. The solid line represents sequences of the vector, pBR322, and the stippled line represents the cloned insert containing the codA gene. A linear representation of the EcoRI-BamHI insert is shown below the plasmid map. The codA gene is indicated by a solid line with an arrow showing the direction of transcription. The scale of each figure is located below the figure.

Figure 17A:
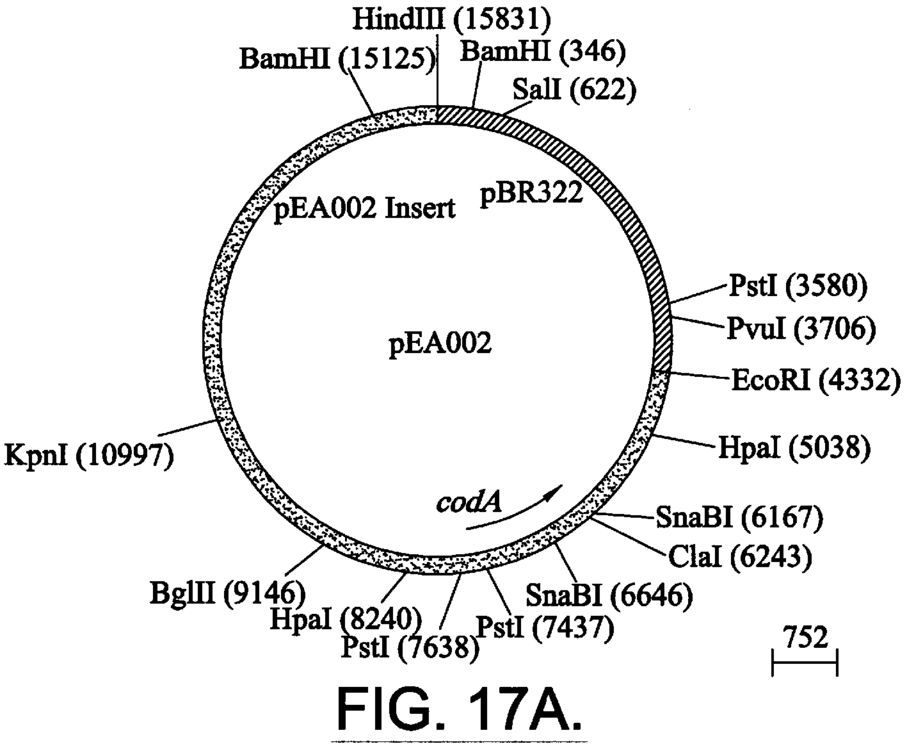
Figure 17B:
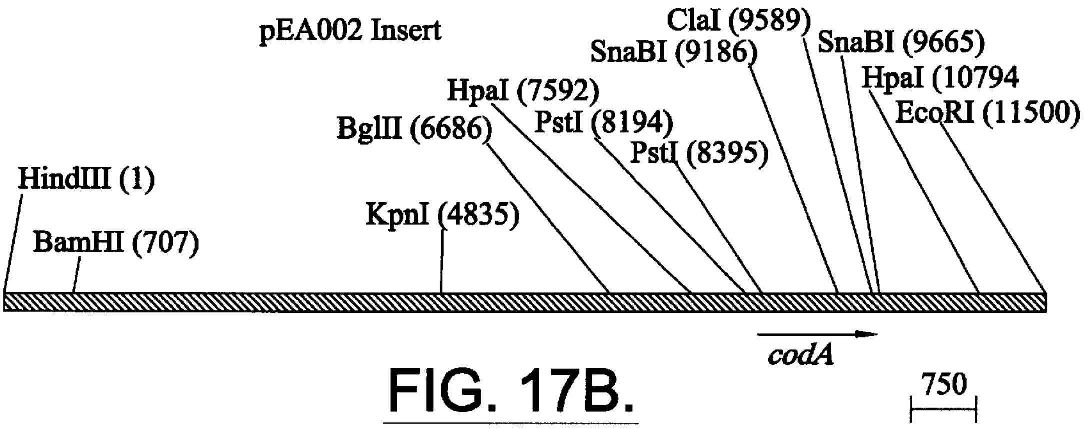

FIG. 17: Restriction map of the plasmid pEA002. The solid line represents sequences of the vector, pBR322, and the stippled line represents the cloned insert containing the codA gene. A linear representation of the EcoRI-HindIII insert is shown below the plasmid map. The codA gene is indicated by a solid line with an arrow showing the direction of transcription. The scale of each figure is located below the figure.

Figure 18:
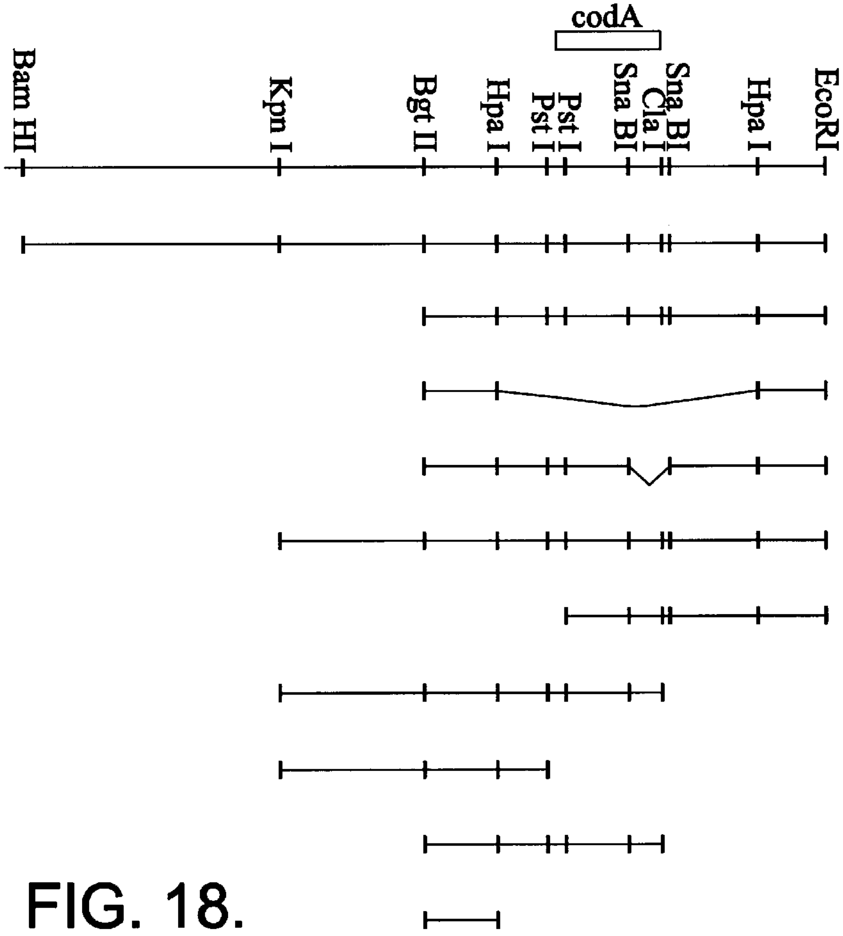

FIG. 18: Restriction maps of plasmid DNA inserts and their phenotypic characteristics and enzymatic activities. The coding region of codA is indicated at the top. a. Plasmids pEA001–005 are cloned into pBR322, while plasmids pEA006–0014 are cloned into pBS+. b. Phenotype refers to the ability of a plasmid to allow BA101 to utilize cytosine as a sole pyrimidine source. c. Specific activity is defined as nmol cytosine or 5-FC deaminated/mg protein/min. Specific activity was measured spectrophotometrically as a decrease in absorbance at 285 nm in a I ml assay mix containing cell extract in 50 mM Tris-HCl, pH 7.3, and 0.5 mM cytosine or 5-FC.

Figure 19A:
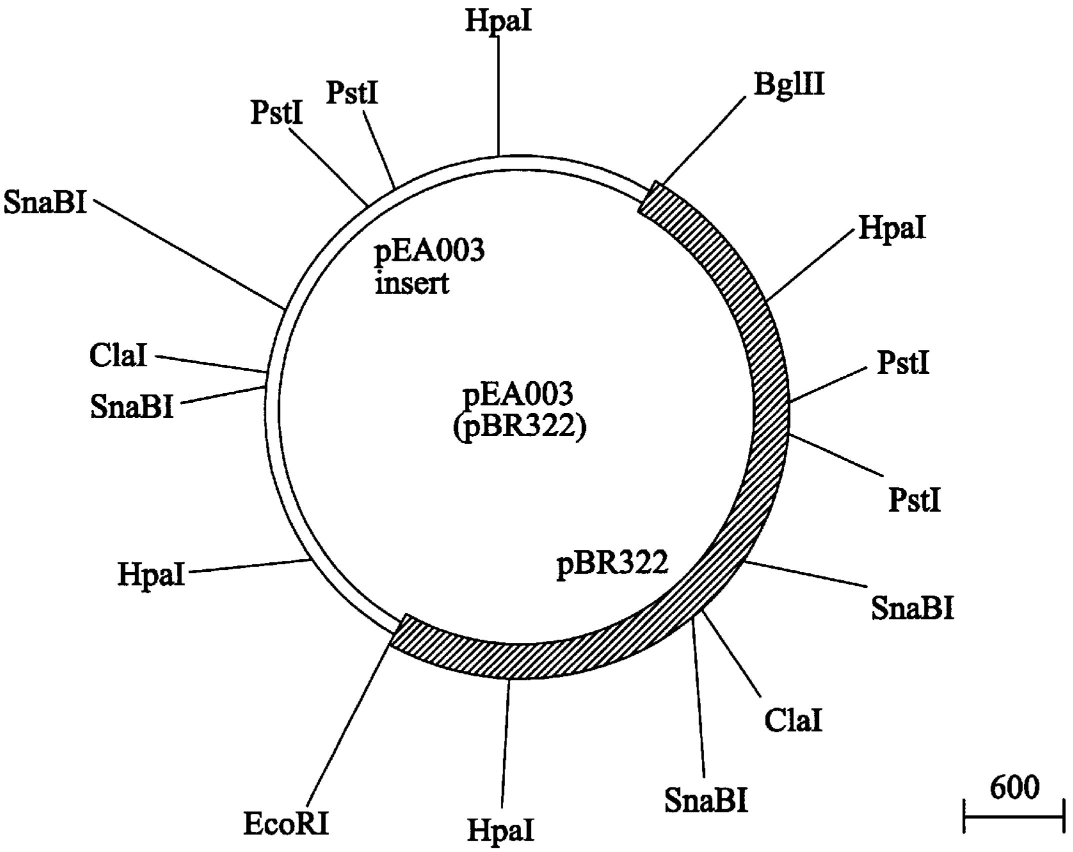
Figure 19B:
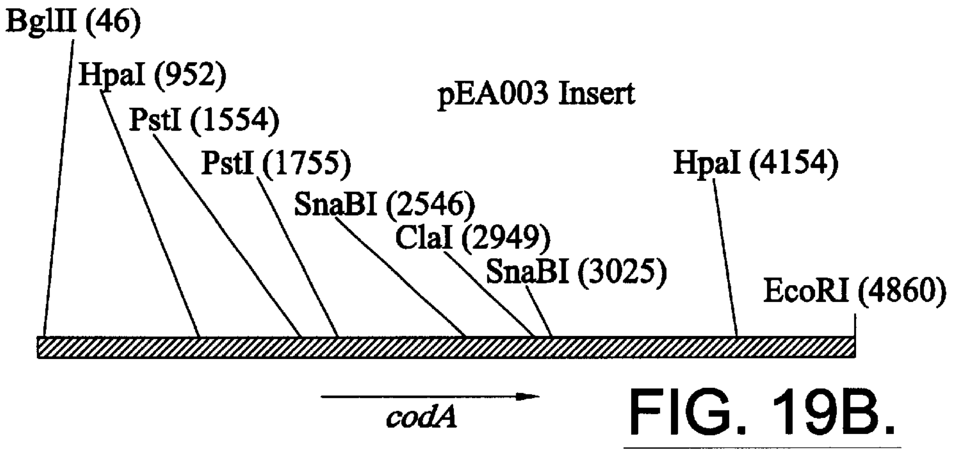

FIG. 19: Restriction map of the plasmid pEA003. The solid line represents sequences of the vector, pBR322, and the stippled line represents the cloned insert containing the codA gene. A linear representation of the EcoRI-Bg/11 insert is shown below the plasmid map. The codA gene is indicated by a solid line with an arrow showing the direction of transcription. The scale of the plasmid is located below the figure.

Figure 20:
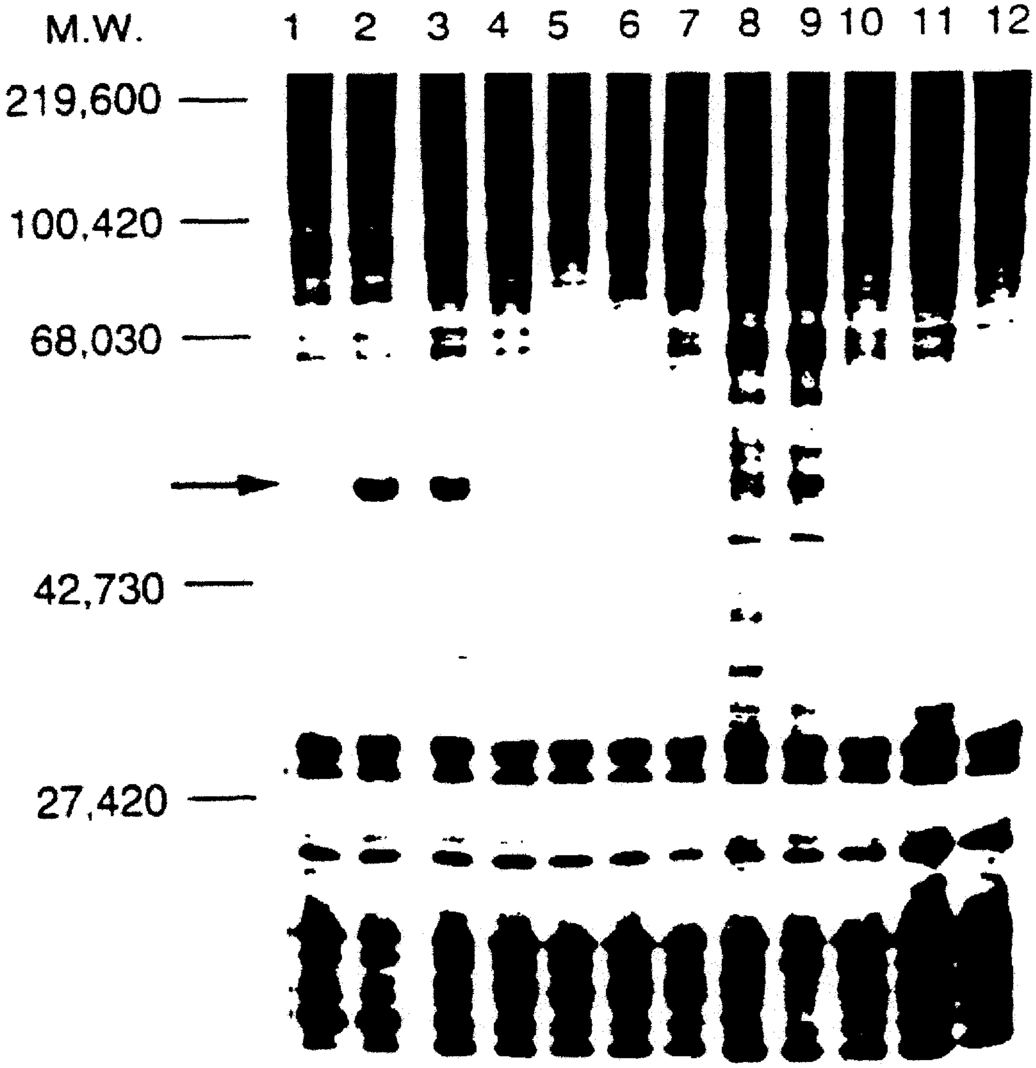

FIG. 20: PAGE analysis of cell extracts prepared from cultures of BA 101 transformed with various plasmids.

Lanes: 1, pBR322; 2, 3, pEA006; 4, pEA005; 5, pEA001; 6, pEA003; 7, pEA004; 8, pEA001; 9, pEA006; 10, pEA009, 11, pEA013; and 12, pEA014. The extracts in lanes 1–7 were prepared from cultures grown in minimal medium, while those in lanes 8–12 were prepared from cultures grown in LB. The arrow points to the CD band, and the molecular weight markers are indicated to the left.

FIG. 21: Sequence of codA extending from the PstI site to the PvuII site(SEQ ID NO:6). The coding region is translated (SEQ ID NO:15) underneath the DNA sequence with the amino acids verified by protein sequencing underlined.

Figure 22:
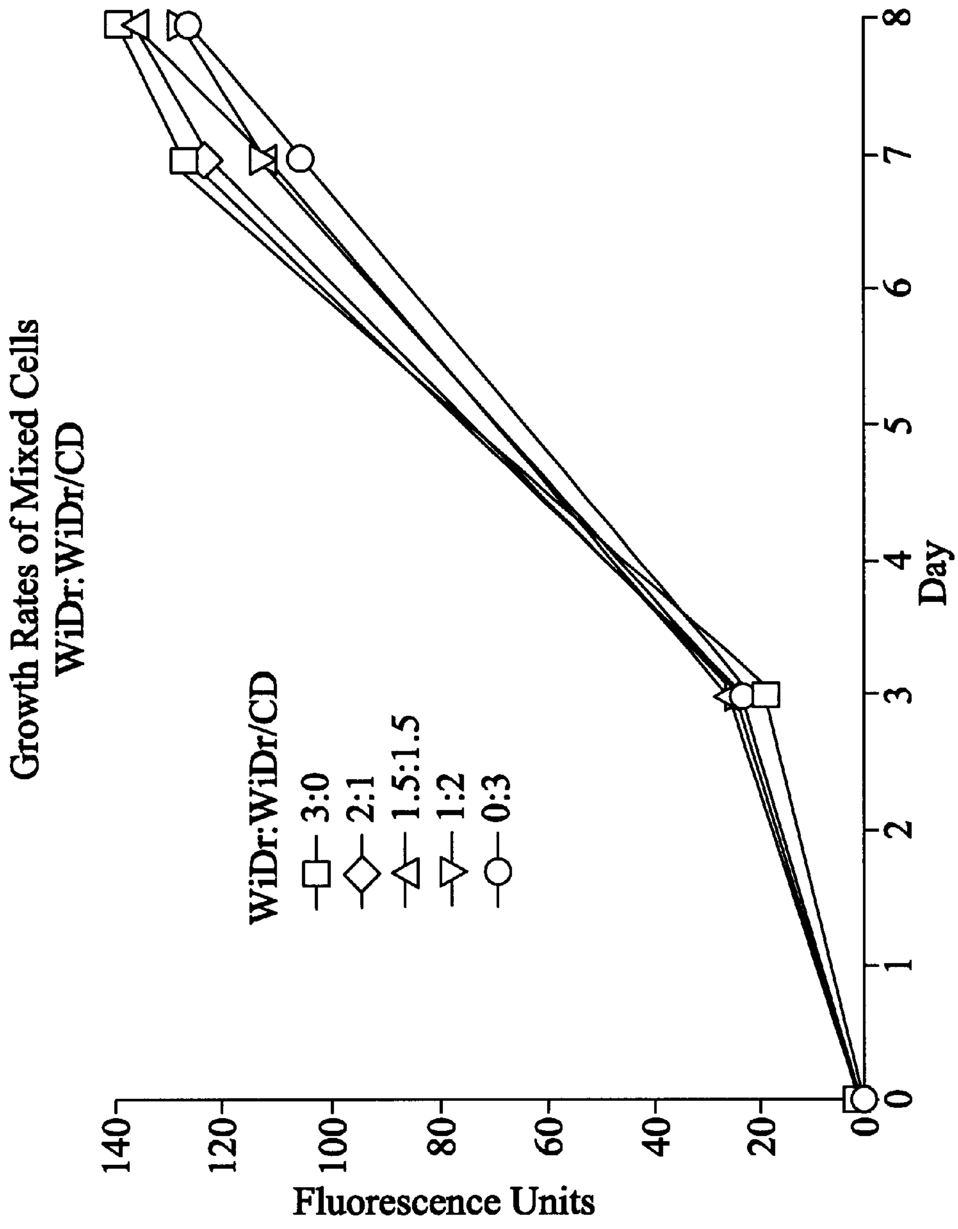

FIG. 22: Growth rates of mixed WiDr and WiDr/CD cells. This graph shows fluorescence units of 96 well microtiter dishes that were plated on Day-1 with 3000 cells/well at the ratios indicated in the legend. The plates were stained and read on Days 0, 3, 7, and 8.

Figure 23:
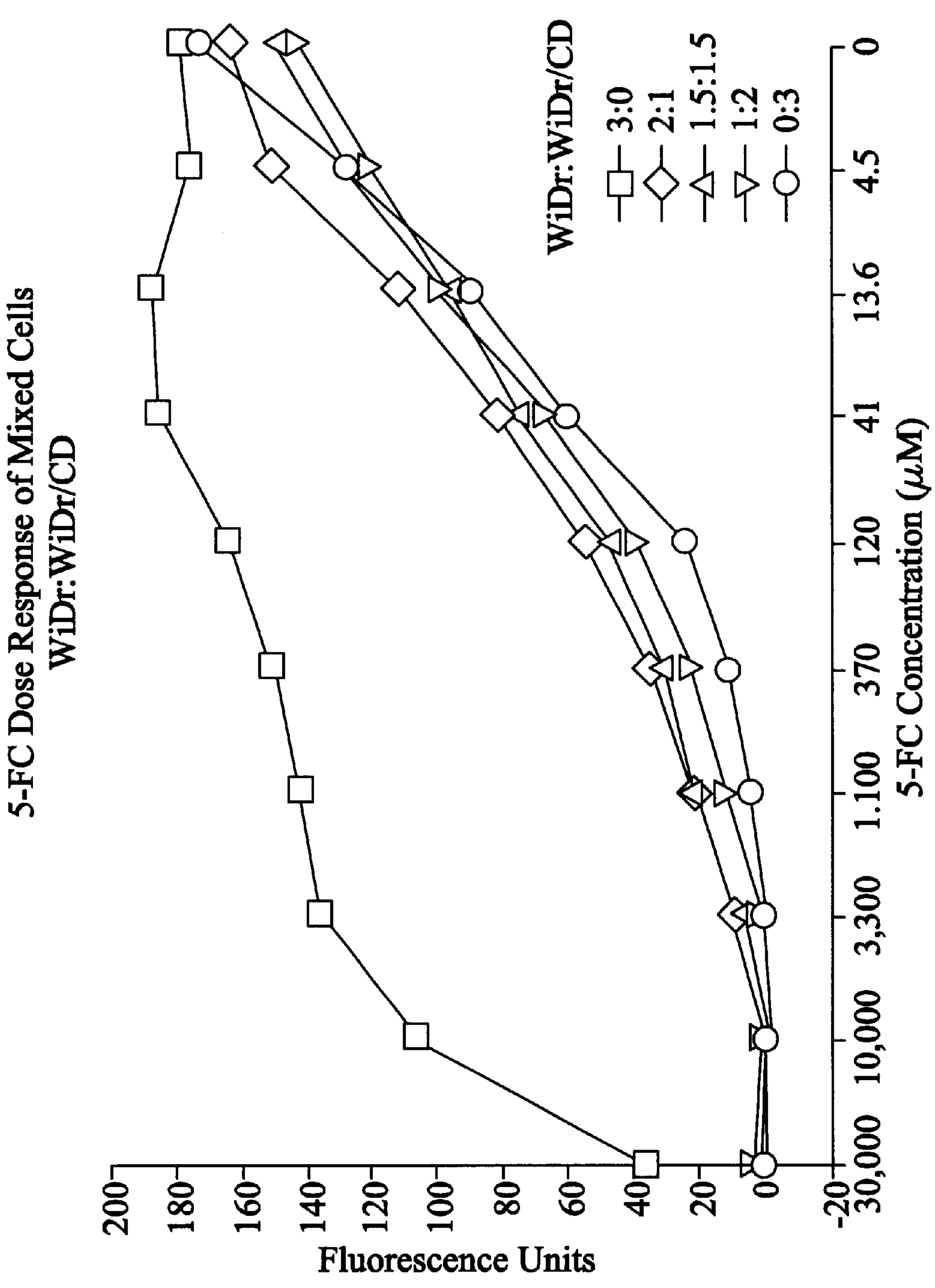

FIG. 23: 5-FC dose response of mixed WiDr and WiDr/CD cells. This graph shows fluorescence units of 96 well microtiter dishes that were plated on Day-1 with 3000 cells/well at the ratios indicated in the legend. Beginning on Day 3, the cells were dosed with serially diluted 5-FC at the concentrations indicated on the x axis. The plates were stained and read on Day 8.

SUMMARY OF THE INVENTION

Gene therapy involves the stable integration of new genes into target cells and the expression of those genes, once they are in place, to alter the phenotype of that particular target cell (for review see Anderson, W. F. Science 226, 401–409 (1984) and McCormick, D. Biotechnology 3, 689–693, (1985)). Gene therapy may be beneficial for the treatment of genetic diseases that involve the replacement of one defective or missing enzyme, such as; hypoxanthine-guanine phosphoribosyl transferase in Lesch-Nyhan disease, purine nucleoside phosphorylase in severe immunodeficiency disease, and adenosine deaminase in severed combined immunodeficiency disease.

It has now been found that it is possible to selectively arrest the growth of, or kill, mammalian carcinoma cells with chemical agents capable of selective conversion to cytotoxic(causing cell death) or cytostatic(suppressing cell multiplication and growth) metabolites. This is achieved by the construction of a molecular chimaera comprising a "target tissue-specific" transcriptional regulatory sequence (TRS) that is selectively activated in target cells, such as cancerous cells, and that controls the expression of a heterologous enzyme. This molecular chimaera may be manipulated via suitable vectors and incorporated into an infective virion. Upon administration of an infective virion containing the molecular chimaera to a host(e.g., mammal or human), the enzyme is selectively expressed in the target cells. Administration of compounds that are selectively metabolised by the enzyme into metabolites that are either further metabolised to or are, in fact, cytotoxic or cytostatic agents can then be achieved in situ.

Molecular chimaeras(recombinant molecules comprised of unnatural combinations of genes or sections of genes), and infective virions(complete viral particles capable of infecting appropriate host cells) are well known in the art of molecular biology and are further described hereinafter.

The invention is generally applicable and is demonstrated with respect to the treatment of hepatocellular and colorectal carcinomas.

As mentioned above the overwhelming percentage of mammals which have hepatocellular carcinoma(HCC) die from the primary tumour. However, approximately 90% of HCC patients have overt metastatic disease at time of death. These metastases exhibit the typical phenotype of the primary tumour and will also selectively express the heterologous enzyme and selectively activate administered compounds, as herein defined, to cytotoxic or cytostatic metabolites.

A number of enzyme prodrug combinations may be used for this purpose, providing the enzyme is capable of selectively activating the administered compound either directly or through an intermediate to a cytostatic or cytotoxic metabolite. The choice of compound will also depend on the enzyme system used, but must be selectively metabolised by the enzyme either directly or indirectly to a cytotoxic or cytostatic metabolite. The term heterologous enzyme, as used herein, refers to an enzyme that is derived from or associated with a species which is different from the host to be treated and which will display the appropriate characteristics of the abovementioned selectivity. In addition, it will also be appreciated that a heterologous enzyme may also refer to an enzyme that is derived from the host to be treated that has been modified to have unique characteristics unnatural to the host.

The varicella zoster virus (VZV) encodes a specific thymidine kinase protein. The gene has been cloned, sequenced, and characterised (Davison A. J., Scott J. E. J. Gen. Virol. 67, 1759–1816 (1986)). The VZV thymidine kinase will, in contrast to the mammalian enzyme, selectively monophosphorylate specific purine arabinosides and substituted pyrimidine compounds. It has now been found that certain purine and pyrimidine analogues of Formulas (I) and (II), particularly those of Formula I as hereinafter defined, are converted to cytotoxic or cytostatic metabolites in specific mammalian cells that have been genetically modified to selectively express VZV thymidine kinase. For example 9-(β-D-arabinofuranosyl)-6-methoxy-9H-purine is converted to (9-β-D-arabinofuranosyl)-adenine triphosphate (Ara ATP) which is cytotoxic.

Other enzyme prodrug combinations include the bacterial (for example, from Pseudomonas) enzyme carboxvpeptidase G2 with the prodrug para-N-bis-(2-chloroethyl)-aminobenzoyl glutamic acid. Cleavage of the glutamic acid moiety from this compound releases a toxic benzoic acid mustard. Alkaline phosphatase from, for example, calf intestine, will convert inactive phosphorylated compounds such as etoposide phosphate, doxorubicin phosphate, and mitomycin phosphate to toxic dephosphorylated metabolites. Penicillin-V amidase will convert phenoxyacetamide derivatives of doxorubicin and melphalan to toxic metabolites, and cytosine deaminase(for example from *E. Coli* will convert 5-fluorocytosine to toxic 5-fluorouracil.

The enzyme cytosine deaminase catalyzes the deamination of cytosine to uracil. Cytosine deaminase is present in microbes and fungi but absent in higher eukaryotes. This enzyme catalyzes the hydrolytic deamination of cytosine and 5-fluorocytosine(5-FC) to uracil and 5-fluorouracil(5-FU), respectively. Since mammalian cells do not express significant amounts of cytosine deaminase, they are incapable of converting 5-FC to the toxic metabolite 5-FU and therefore 5-fluorocytosine is nontoxic to mammalian cells at concentrations which are effective for antimicrobial activity. 5-Fluorouracil is highly toxic to mammalian cells and is widely used as an anticancer agent.

In mammalian cells, some genes are ubiquitously expressed. Most genes, however, are expressed in a temporal and/or tissue-specific manner, or are activated in response to extracellular inducers. For example, certain genes are actively transcribed only at very precise times in ontogeny in specific cell types, or in response to some inducing stimulus. This regulation is mediated in part by the interaction between transcriptional regulatory sequences (for example, promoter and enhancer regulatory DNA sequences), and sequence-specific, DNA-binding transcriptional protein factors.

It has now been found that it is possible to alter certain mammalian cells, e.g. liver cells or transformed liver cells, to selectively express a heterologous enzyme as hereinbefore defined, e.g. VZV TK. Colorectal carcinoma cells, metastatic colorectal carcinoma cells and hepatic colorectal carcinoma cells can also be altered by this approach to selectively express a heterologous enzyme, e.g., cytosine deaminase. This is achieved by the construction of molecular chimaeras in an expression cassette.

Expression cassettes themselves are well known in the art of molecular biology. Such an expression cassette contains all essential DNA sequences required for expression of the heterologous enzyme in a mammalian cell. For example, a preferred expression cassette will contain a molecular chimaera containing the coding sequence for VZV TK or cytosine deaminase(CD), an appropriate polyadenylation signal for a mammalian gene (i.e., a polyadenylation signal that will function in a mammalian cell), and suitable enhancers and promoter sequences in the correct orientation.

Normally, two DNA sequences are required for the complete and efficient transcriptional regulation of genes that encode messenger RNAs in mammalian cells: promoters and enhancers. Promoters are located immediately upstream (5') from the start site of transcription. Promoter sequences are required for accurate and efficient initiation of transcription. Different gene-specific promoters reveal a common pattern of organisation. A typical promoter includes an AT-rich region called a TATA box (which is located approximately 30 base pairs 5' to the transcription initiation start site) and one or more upstream promoter elements (UPEs). The UPEs are a principle target for the interaction with sequence-specific nuclear transcriptional factors. The activity of promoter sequences is modulated by other sequences called enhancers. The enhancer sequence may be a great distance from the promoter in either an upstream (5') or downstream (3') position. Hence, enhancers operate in an orientation- and position-independent manner. However, based on similar structural organisation and function that may be interchanged, the absolute distinction between promoters and enhancers is somewhat arbitrary. Enhancers increase the rate of transcription from the promoter sequence. It is predominantly the interaction between sequence-specific transcriptional factors with the UPE and enhancer sequences that enable mammalian cells to achieve tissue-specific gene expression. The presence of these transcriptional protein factors (tissue-specific, trans-activating factors) bound to the UPE and enhancers (cis-acting, regulatory sequences) enables other components of the transcriptional machinery, including RNA polymerase, to initiate transcription with tissue-specific selectivity and accuracy.

The selection of the transcriptional regulatory sequence, in particular the promoter and enhancer sequence will depend on the targeted cells. Examples include the albumin (ALB) and alpha-fetoprotein (AFP) transcriptional regulatory sequence (for example, the promoter and enhancer) specific for normal hepatocytes and transformed hepatocytes, respectively; the transcriptional regulatory sequence for carcinoembryonic antigen (CEA) for use in colorectal carcinoma, metastatic colorectal carcinoma, and hepatic colorectal metastases, transformed cells of the gastrointestinal tract, lung, breast and other tissues; the transcriptional regulatory sequence for tyrosine hydroxylase, choline acetyl transferase, or neuron specific enolase for use in neuroblastomas; the transcriptional regulatory sequence for glial fibro acidic protein for use in gliomas; and the transcriptional regulatory sequence for insulin for use in tumours of the pancreas.

Further examples include the transcriptional regulatory sequence specific for gama-glutamyltranspeptidase for use in certain liver tumours and dopa decarboxylase for use in treating certain tumours of the lung.

In addition, the transcriptional regulatory sequences from certain oncogenes may be used as these are expressed predominantly in certain tumour types. Good examples of these include the HER-2/neu oncogene regulatory sequence, which is expressed in breast tumours, and the regulatory sequence specific for the N-myc oncogene for neuroblastomas.

The ALB and AFP genes exhibit extensive homology with regard to nucleic acid sequence, gene structure, amino acid sequence, and protein secondary folding (for review see Ingram R. S., Scott R. W., Tilghman S. M. PNAS 78, 4694–4698 (1981)). These genes are independently but reciprocally expressed in ontogeny. In normal development, ALB transcription is initiated shortly before birth and continues throughout adulthood. Transcriptional expression of ALB in the adult is confined to the liver. AFP is normally expressed in fetal liver, the visceral endoderm of the yolk sac, and the fetal gastrointestinal tract, but declines to undetectable levels shortly after birth and is not significantly expressed in nonpathogenic or nonregenerating adult liver or in other normal adult tissue. However, AFP transcription in adult liver often increases dramatically in HCC. In addition, AFP transcription may also be elevated in nonseminomatous and mixed carcinoma of the testis, in endodermal sinus tumours, in certain teratocarcinomas, and in certain gastrointestinal tumours. Liver-specific expression of AFP and ALB is the result of interactions of the regulatory sequences of their genes with trans-activating transcriptional factors found in nuclear extracts from liver. The AFP and ALB transcriptional regulatory sequences are preferred for generating hepatoma-specific or general liver-specific expression respectively, of molecularly combined genes because the AFP and ALB genes are regulated at the transcriptional level and their mRNAs are among the most abundant polymerase II transcripts in the liver.

Several mammalian ALB and AFP promoter and enhancer sequences have been identified (for review see Pinkert C. A., Ornitz D. M., Brinster R. L., Palmiter R. D. Genes Dev. 1, 268–276 (1987); Hammer R. E., Krumlauf R., Camper S. A., Brinster R. L. Science 235, 53–58 (1987); Wantanabe K., Saito A., Tamaoki T. The J. of Biol. Chem. 262, 4812–4818 (1987)). These sequences enable the selective and specific expression of genes in liver hepatocytes (normal and transformed) and hepatomas, respectively.

For example, as shown in FIG. 1, a mammalian ALB promoter is contained within a 300-bp fragment 5' to the transcription initiation start site of the albumin gene. The sequence contained between 300 bp 5' and 8,500 bp 5' to the transcription initiation start site of the murine albumin gene is dispensable for liver-specific expression. However, a liver-specific enhancer sequence is contained in a fragment located from 8,500 bp 5' to 10,400 bp 5' to the transcription initiation start site (FIG. 1A). If the ALB promoter and enhancer elements are present, liver-specific expression of a heterologous structural gene positioned in a proper 3' orientation can be achieved (FIG. 1B). Liver-specific expression of a 3' heterologous structural gene positioned in the proper orientation to the ALB promoter and enhancer sequences is also maintained when the nonessential intervening sequences located between 300 bp 5' and 8,500 bp 5' to the transcription initiation start site are eliminated (FIG. 1C). The truncation of nonessential sequences is accomplished by standard molecular biological methodology well known in the art and results in a molecular chimaera that can be used to direct liver-specific expression of VZV TK or any other heterologous enzyme.

Similar to the regulatory structure of the ALB gene, the regulatory elements of the AFP genes promote tissue-specific expression of AFP in certain liver pathologies such as HCC (Godbout R., Ingram R., Tilghman S. M. Mol.Cell. Biol. 6, 477–487 (1986); Hammer R. E., Krumlauf R., Camper S. A., Brinster R. L. Science 235, 53–58 (1987)). The regulatory elements of a mammalian AFP gene consist of a specific 5' promoter-proximal region (located in some mammalian species between 85 and 52 bp 5' to the gene). This sequence is essential for transcription in hepatomas. In addition, there are upstream (5') regulatory elements well-defined for the murine AFP gene, which behave as classical enhancers (Godbout R., Ingram R., Tilghman S. M. Mol. Cel.Biol. 6, 477–487 (1986); Hammer R. E., Krumlauf R., Camper S. A., Brinster R. L. Science 235, 53–58 (1987)). These upstream regulatory elements are designated elements I, II, and III and are located between 1,000 to 7,600 bp 5' to the transcription initiation start site for the murine AFP gene. These three enhancer domains are not functionally equivalent at generating tissue-specific expression of AFP. Elements I and II have the greatest capacity to direct liver-specific expression of AFP. It is important to note that the regulatory sequences of the alpha-fetoprotein gene advantageously contain the sequences not only for tissue-specific transcriptional activation but also for repression of expression in tissues that should not express AFP. In a similar fashion the regulatory regions of the human alpha-fetoprotein gene have been characterised (Wantanabe K., Saito M., Tamaoki T. J.Biol.Chem. 262, 4812–4818 (1987)). A structural gene placed in the correct orientation 3' to the AFP regulatory sequences will enable that structural gene to be selectively expressed in fetal liver, hepatomas, non-seminomatous carcinomas of the testis, certain teratocarcinomas, certain gastrointestinal tumours and other normal and pathological cells or tissues that specifically express AFP.

Carcinoembryonic antigen(CEA) is a tumor-associated marker that is expressed in a large percentage of primary and metastatic CRC cells and is widely used as an important diagnostic tool for postoperative surveillance, chemotherapy efficacy determinations, immunolocalization and immunotherapy. By placing the expression of the gene encoding CD under the transcriptional control of the CRC-associated marker gene, CEA, the nontoxic compound, 5-FC, can be metabolically activated to 5-FU selectively in CRC cells(for example, hepatic CRC cells).

CEA genomic clones were identified and isolated from the human chromosome 19 genomic library LL19NL01, ATCC number 57766, by standard techniques described hereinafter.

The cloned CEA sequences (FIG. 12) comprise CEA enhancers in addition to the CEA promoter. The CEA enhancers are especially advantagous for high level expression in CEA-positive cells and no expression in CEA-negative cells.

Cytosine deaminase clones were identified and isolated from bacteriophage lambda clones by standard techniques described hereinafter.

It will be appreciated by those skilled in the art that non-dividing normal cells will not have the new genes incorporated by the infective virions. Therefore, cells which contain ALB but are not actively dividing will not express the heterologous enzyme and will therefore be unable to metabolise the non-toxic compounds to cytotoxic or cytostatic agents.

A further advantage of this system is that the generated toxic compound, 5-fluorouracil, can diffuse out of the cell in which it was generated and kill adjacent tumor cells which did not incorporate the artificial gene for cytosine deaminase.

DETAILED DESCRIPTION OF THE THE INVENTION

The present invention provides a molecular chimaera comprising a transcriptional regulatory sequence capable of being selectively activated in target tissue or cells, a DNA sequence operatively linked to the transcriptional regulatory sequence and encoding a heterologous enzyme, the enzyme capable of catalyzing the production of an agent cytotoxic or cytostatic to the target cells.

Preferably, the target tissue or cells are selected from the group consisting of hepatocellular carcinoma, colorectal carcinoma, metastatic colorectal carcinoma, and hepatic colorectal carcinoma metastases.

The present invention further provides a molecular chimaera comprising a DNA sequence containing the coding sequence of the gene that codes for a heterologous enzyme under the control of a transcriptional regulatory sequence (TRS) in an expression cassette; the transcriptional regulatory sequence capable of functioning selectively in a target tissue or cancer cell, for example one which is capable of transforming a cancer cell to selectively express an enzyme, for example, thymidine kinase or cytosine deaminase.

The present invention further provides in a preferred embodiment a molecular chimaera comprising a transcriptional regulatory sequence, in particular a promoter that is selectively activated in mammalian target tissue or cells, which is operatively linked to the coding sequence for the gene encoding varicella zoster virus thymidine kinase (VZV TK) or non-mammalian cytosine deaminase(CD).

The molecular chimaera comprises a promoter and additionally comprises an enhancer.

Figure 2A:
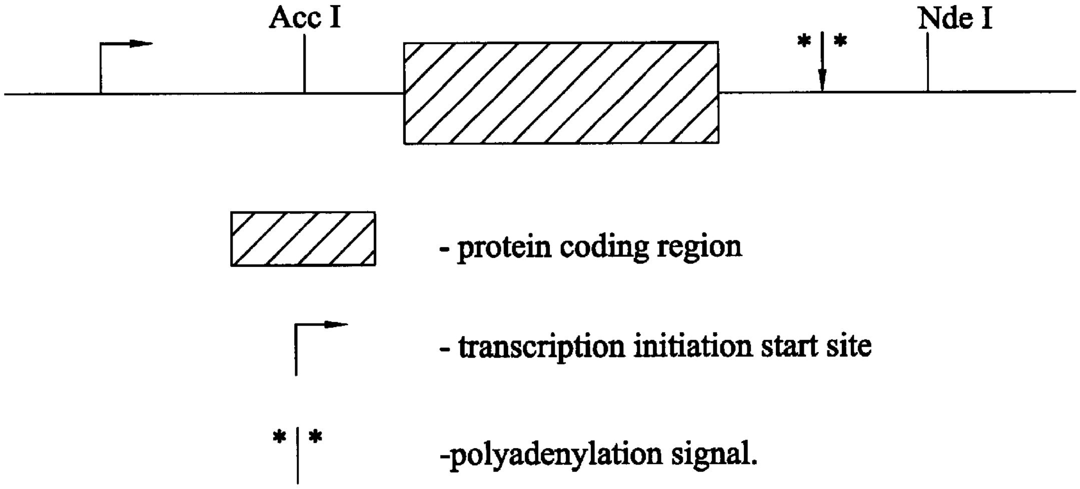
FIG. 2A: Diagram of varicella zoster thymidine kinase gene.

In particular, the present invention provides a molecular chimaera comprising a DNA sequence of the coding sequence of the gene coding for the heterologous enzyme, which is preferably cytosine deaminase, additionally including an appropriate polyadenylation sequence(for example see FIG. 2B), which is linked downstream in a 3' position and in the proper orientation to a mammalian target tissue-specific transcriptional regulatory sequence. Most preferably the expression cassette also contains an enhancer sequence.

The DNA sequence encoding a heterologous enzyme is additionally selected from; carboxypeptidase G2; alkaline phosphatase; penicillin-V amidase; and non-mammalian (e.g., *Escherichia coli*(*E. coli*)) cytosine deaminase(for example see FIG. 12A).

Preferably non-mammalian cytosine deaminase is selected from the group consisting of bacterial, fungal, and yeast cytosine deaminase.

The promoter and enhancer sequences preferably are selected from the transcriptional regulatory sequence for one of albumin (ALB), alpha-fetoprotein (AFP), carcinoembryonic antigen (CEA), cytomegalovirus(CMV), tryrosine hydroxylase, choline acetyl transferase, neuron-specific enolase, glial fibro acidic protein, insulin or gama-glutamyl-transpeptidase, dopa-decarboxylase, HER-2/neu or N-myc oncogene or other suitable genes such as cytomegalovirus (CMV), SV40 or Actin. Most preferably the regulatory sequence for ALB or AFP are used to direct liver-specific or hepatoma-specific expression respectively and the regulatory sequence for CEA is used to direct colorectal carcinoma, metastatic colorectal carcinoma(e.g., hepatic colorectal carcinoma metastases) specific expression.

According to the invention, the regulatory sequence for ALB or AFP are also used to direct colorectal carcinoma or metastatic colorectal carcinoma(e.g., hepatic colorectal carcinoma metastases) specific expression.

Furthermore, according to the invention, the regulatory sequence for CEA is also used to direct liver-specific or hepatoma-specific expression.

Preferably, the DNA sequence encodes the gene for varicella zoster virus thymidine kinase and is operatively linked to the transcriptional regulatory sequence for albumin or alpha-fetoprotein.

Preferably, the DNA sequence encodes the gene for cytosine deaminase and is operatively linked to the transcriptional regulatory sequence for carcino-embryonic antigen.

Another aspect of the invention is the genomic CEA sequence as described by FIG. 12A.

Figure 3A:
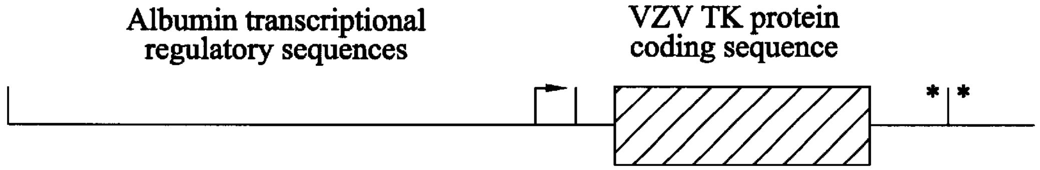
FIG. 3A: Albumin transcriptional regulatory sequence/VZV TK molecular chimaera.
Figure 3B:
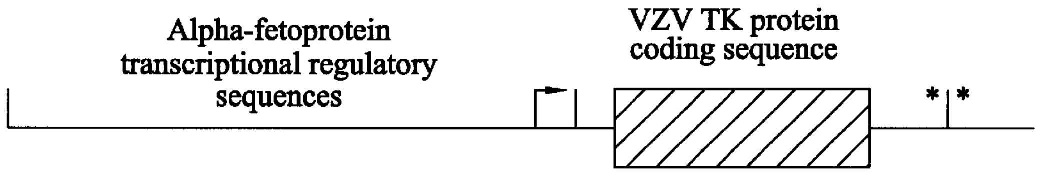
FIG. 3B: Alpha-fetoprotein transcriptional regulatory sequence/VZV TK molecular chimaera.

The molecular chimaera of the present invention may be made utilizing standard recombinant DNA techniques. Thus the coding sequence and polyadenylation signal of, for example, the VZV thymidine kinase (VZV TK) gene(see FIGS. 2A and 2B) is placed in the proper 3' orientation to the essential ALB or AFP transcriptional regulatory elements. These molecular chimaeras enable the selective expression of VZV TK in cells or tissue that normally express ALB or AFP, respectively (FIGS. 3A and 3B). Expression of the VZV TK gene in mammalian liver, hepatomas, certain tumours of the gastrointestinal tract, nonseminomatous carcinomas of the testis, certain teratocarcinomas, and other tumours will enable relatively nontoxic arabinosides and pyrimidines as herein defined to be selectivelv metabolised to cytotoxic and/or cytostatic metabolites thereof.

The coding sequence of cytosine deaminase and a polyadenylation signal(for example see FIGS. 12A and 12B) are placed in the proper 3' orientation to the essential CEA transcriptional regulatory elements. This molecular chimaera enables the selective expression of CD in cells or tissue that normally express CEA. Expression of the CD gene in mammalian CRC and metastatic CRC (hepatic colorectal carcinoma metastases) will enable nontoxic 5-fluorocytosine to be selectively metabolised to cytotoxic 5-fluorouracil.

Accordingly, in a second aspect of the present invention, there is provided a method of constructing a molecular chimaera comprising linking a DNA sequence encoding a heterologous enzyme gene, e.g. VZV TK or CD, to a tissue-specific promoter.

In particular the present invention provides a method of constructing a molecular chimaera as herein defined, the method comprising ligating a DNA sequence encoding the coding sequence and polyadenylation signal of the gene for a heterologous enzyme (e.g., VZV thymidine kinase or non-mammalian CD) to a mammalian tissue-specific transcriptional regulatory sequence (e.g., promoter sequence and enhancer sequence).

The VZV thymidine kinase coding sequence and 3' polyadenylation signal reside in an approximately 1,381 bp Accl/Nde I restriction endonuclease fragment (see FIG. 2B).

Preferably it is the 1,381 bp Accl/Nde I fragment containing the VZV TK coding sequence and polyadenylation signal(FIG. 2B) that is ligated to the mammalian tissue-specific promoter and enhancer sequences, although it will be appreciated that other DNA fragments containing the VZV TK gene could be used. Moreover, the VZV TK polyadenylation signal could be replaced with another suitable polyadenylation signal, such as that from the cytomegalovirus(CMV) or SV40 virus or other mammalian genes.

Preferably the promoter and enhancer sequences are selected from the transcriptional regulatory sequences for one of albumin (ALB), alpha-fetoprotein (AFP), carcinoembryonic antigen (CEA), tryrosine hydroxylase, choline acetyl transferase, neuron-specific enolase, glial fibro acidic protein, insulin, gama-glutamyltranspeptidase, dopa decarboxylase, HER-2/neu or N-myc oncogenes or other suitable genes such as cytomegalovirus(CMV), SV40 or Actin.

These molecular chimaeras can be delivered to the target tissue or cells by a delivery system. For administration to a host(e.g., mammal or human), it is necessary to provide an efficient in vivo delivery system that stably incorporates the molecular chimaera into the cells. Known methods utilize techniques of calcium phosphate transfection, electroporation, microinjection, liposomal transfer, ballistic barrage, DNA viral infection or retroviral infection. For a review of this subject see Biotechniques 6, No.7, (1988).

The technique of retroviral infection of cells to integrate artificial genes employs retroviral shuttle vectors which are known in the art(Miller A. D., Buttimore C. Mol. Cell. Biol. 6, 2895–2902 (1986)). Essentially, retroviral shuttle vectors (retroviruses comprising molecular chimaeras used to deliver and stably integrate the molecular chimaera into the genome of the target cell) are generated using the DNA form of the retrovirus contained in a plasmid. These plasmids also contain sequences necessary for selection and growth in bacteria. Retroviral shuttle vectors are constructed using standard molecular biology techniques well known in the art. Retroviral shuttle vectors have the parental endogenous retroviral genes (e.g., gag, pol and env) removed from the vectors and the DNA sequence of interest is inserted, such as the molecular chimaeras that have been described. The vectors also contain appropriate retroviral regulatory sequences for viral encapsidation, proviral insertion into the target genome, message splicing, termination and polyadenylation. Retroviral shuttle vectors have been derived from the Moloney murine leukemia virus (Mo-MLV) but it will be appreciated that other retroviruses can be used such as the closely related Moloney murine sarcoma virus. Other DNA viruses may also prove to be useful as delivery systems. The bovine papilloma virus (BPV) replicates extrachromosomally, so that delivery systems based on BPV have the advantage that the delivered gene is maintained in a nonintegrated manner.

Thus according to a third aspect of the present invention there is provided a retroviral shuttle vector comprising the molecular chimaeras as hereinbefore defined. Preferably, the chimaera comprises a transcriptional regulatory sequence which is selectively activated in target cells and operatively linked to the coding sequence for the gene encoding a heterologous enzyme. The chimaera further comprises a DNA sequence of the coding and polyadenylation sequence of the gene coding for VZV TK or non-mammalian(e.g., *E. coli*) cytosine deaminase linked in a 3' position and in the proper orientation to a transcriptional regulatory sequence to control expression of the VZV TK gene or CD gene respectively. The DNA sequence encoding VZV TK or CD is operatively linked to a promoter and to a polyadenylation sequence to control expression of the VZV TK or CD genes.

The advantages of a retroviral-mediated gene transfer system are the high efficiency of the gene delivery to the targeted tissue or cells, sequence specific integration regarding the viral genome (at the 5' and 3' long terminal repeat (LTR) sequences) and little rearrangements of delivered DNA compared to other DNA delivery systems.

Accordingly in a preferred embodiment of the present invention there is provided a retroviral shuttle vector comprising a DNA sequence comprising a 5' viral LTR sequence, a cis-acting psi-encapsidation sequence, a molecular chimaera as hereinbefore defined and a 3' viral LTR sequence (FIG. 4A and FIG. 4B).

In a preferred embodiment, and to help eliminate non-tissue-specific expression of the molecular chimaera, the molecular chimaera is placed in opposite transcriptional orientation to the 5' retroviral LTR (FIG. 4A and FIG. 4B). In addition, a dominant selectable marker gene may also be included that is transcriptionally driven from the 5' LTR sequence. Such a dominant selectable marker gene may be the bacterial neomycin-resistance gene NEO (Aminoglycoside 3' phospho- transferase type II), which confers on eukaroytic cells resistance to the neomycin analogue Geneticin(antibiotic G418 sulphate; registered trademark of GIBCO)(FIGS. 4A and 4B). The NEO gene aids in the selection of packaging cells that contain these sequences (see below).

The retroviral vector used in the examples is based on the Moloney murine leukemia virus but it will be appreciated that other vectors may be used. Vectors containing a NEO gene as a selectable marker have been described, for example, the N2 vector (Eglitis M. A., Kantoff P., Gilboa E., Anderson W. F. Science 230, 1395–1398 (1985)).

A theoretical problem associated with retroviral shuttle vectors is the potential of retroviral long terminal repeat (LTR) regulatory sequences transcriptionally activating a cellular oncogene at the site of integration in the host genome. This problem may be diminished by creating SIN vectors (FIG. 4A). SIN vectors are self-inactivating vectors that contain a deletion comprising the promoter and enhancer regions in the retroviral LTR. The LTR sequences of SIN vectors do not transcriptionally activate 5' or 3' genomic sequences. The transcriptional inactivation of the viral LTR sequences diminishes insertional activation of adjacent target cell DNA sequences and also aids in the selected expression of the delivered molecular chimaera. SIN vectors are created by removal of approximately 299 bp in the 3' viral LTR sequence (Gilboa E., Eglitis P. A., Kantoff P. W., Anderson W. F. Biotechniques 4, 504–512 (1986)).

Thus preferably the retroviral shuttle vectors of the present invention are SIN vectors.

Since the parental retroviral gap, pol, and env genes have been removed from these shuttle vectors, a helper virus system may be utilised to provide the gag, pol, and env retroviral gene products in trans to package or encapsidate the retroviral vector into an infective virion. This is accomplished by utilising specialised "packaging" cell lines, which are capable of generating infectious, synthetic virus yet are deficient in the ability to produce any detectable wild-type virus. In this way the artificial synthetic virus contains a chimaera of the present invention packaged into synthetic artificial infectious virions free of wild-type helper virus. This is based on the fact that the helper virus that is stably integrated into the packaging cell contains the viral structural genes, but is lacking the psi-site, a cis-acting regulatory sequence which must be contained in the viral genomic RNA molecule for it to be encapsidated into an infectious viral particle.

Accordingly, in a fourth aspect of the present invention, there is provided an infective virion comprising a retroviral shuttle vector, as hereinbefore described, said vector being encapsidated within viral proteins to create an artificial infective, replication-defective retrovirus.

Preferably, the retroviral shuttle vector comprises a shuttle vector comprising a molecular chimaera having the transcriptional regulatory sequence of AFP, ALB, or CEA. In particular, the shuttle vector contains a AFP/VZV TK chimaera, a ALB/VZV TK chimaera or a CEA/CD chimaera. The shuttle vector can further contain a AFP/CD chimaera, a ALB/CD chimaera, or a CEA/VZV-TK chimaera.

In a fifth aspect of the present invention there is provided a method for producing infective virions of the present invention by delivering the artificial retroviral shuttle vector comprising a molecular chimaera of the invention, as hereinbefore described, into a packaging cell line.

The packaging cell line may have stably integrated within it a helper virus lacking a psi-site and other regulatory sequence, as hereinbefore described, or, alternatively, the packaging cell line may be engineered so as to contain helper virus structural genes within its genome.

In addition to removal of the psi-site, additional alterations can be made to the helper virus LTR regulatory sequences to ensure that the helper virus is not packaged in virions and is blocked at the level of reverse transcription and viral integration.

Alternatively, helper virus structural genes (i.e., gag, pol, and env) may be individually and independently transferred into the packaging cell line. Since these viral structural genes are separated within the packaging cell's genome, there is little chance of covert recombinations generating wild-type virus.

Accordingly, the present invention also provides for a packaging cell line comprising an infective virion, as described hereinbefore, said virion further comprising a retroviral shuttle vector.

Accordingly, the present invention provides for a packaging cell line comprising a retroviral shuttle vector as described hereinbefore.

In addition to retroviral-mediated gene delivery of the chimeric, artificial, therapeutic gene, other gene delivery systems known to those skilled in the art can be used in accordance with the present invention. These other gene delivery systems include other viral gene delivery systems known in the art, such as the adenovirus delivery systems.

Non-viral delivery systems can be utilized in accordance with the present invention as well. For example, liposomal delivery systems can deliver the therapeutic gene to the tumor site via a liposome. Liposomes can be modified to evade metabolism and/or to have distinct targetting mechanisms associated with them. For example, liposomes which have antibodies incorporated into their structure, such as antibodies to CEA, can have targetting ability to CEA-positive cells. This will increase both the selectivity of the present invention as well as it's ability to treat disseminated disease(metastasis).

Another gene delivery system which can be utilized according to the present invention is receptor-mediated delivery, wherein the gene of choice is incorporated into a ligand which recognizes a specific cell receptor. This system can also deliver the gene to a specific cell type. Additional modifications can be made to this receptor-mediated delivery system, such as incorporation of adenovirus components to the gene so that the gene is not degraded by the cellular lysosomal compartment after internalization by the receptor.

The present invention further provides an infective virion as hereinbefore described for use in therapy, particularly for use in the treatment of cancer and more particularly for use in the treatment of HCC, CRC, metastatic CRC, hepatic CRC metastases, nonseminomatous carcinoma of the testis, certain teratocarcinomas and certain gastrointestinal tumours.

The present invention further provides a method of generating cytosine deaminase in a cell which comprises delivering a molecular chimaera into a cell, said chimaera capable of expressing cytosine deaminase inside said cell.

The present invention further provides a method of killing or arresting the growth of cells comprising delivering a molecular chimaera into said cell, said chimaera expressing a heterologous enzyme(e.g., cytosine deaminase) in said cells and exposing said cells to an agent(e.g., 5-fluorocytosine) which is converted by said enzyme to an agent which is cytotoxic or cytostatic to said cells(e.g., 5-fluorouracil).

Selective expression of the heterologous enzyme, in particular the VZV TK gene or CD gene, is accomplished by utilising tissue-specific, transcriptional regulatory (e.g., enhancer and promoter) sequences. Selectivity may be additionally improved by selective infection of target tissue or cells, for example, liver cells or hepatic metastatic colorectal carcinoma cells. The retroviral env gene present in the packaging cell line defines the specificity for host infection. The env gene used in constructing the packaging cell line is modified to encode a ligand for a cell specific binding site to generate artificial, infective virions that selectively infect specific cells, for example, hepatocytes. As an example a retroviral env gene introduced into the packaging cell may be modified in such a way that the artificial, infective virion's envelope glycoprotein will selectively infect hepatocytes via the specific receptor mediated binding pathway utilised by the hepatitis B virus (HBV).

HBV primarily infects hepatocytes via specific receptor mediated binding. The HBV proteins encoded by the pre-S1 and pre-S2 sequences play a major role in the attachment of HBV to hepatocytes (Hepadna Viruses ed. Robinson W., Koike K., Will H. N. Y., A. R. Liss, 189–203, 205–221 (1987)). The env gene of the packaging cell is modified to include the hepatocyte binding site of the large S HBV envelope protein. Such modifications of the env gene introduced into the packaging cell may be performed by standard molecular biology techniques well known in the art.

The infective virion or the packaging cell line according to the invention may be formulated by techniques well known in the art and may be presented as a formulation (composition) with a pharmaceutically acceptable carrier therefor. Pharmaceutically acceptable carriers, in this instance physiologic aqueous solutions, may comprise liquid medium suitable for use as vehicles to introduce the infective virion into a host. An example of such a carrier is saline. The infective virion or packaging cell line may be a solution or suspension in such a vehicle. Stabilizers and antioxidants and/or other excipients may also be present in such pharmaceutical formulations(compositions), which may be administered to a mammal by any conventional method (e.g., oral or parenteral routes). In particular, the infective virion may be administered by intra-venous or intra-arterial infusion. In the case of treating HCC or hepatic metastatic CRC, intra-hepatic arterial infusion may be advantageous. The packaging cell line can be administered directly to the tumor or near the tumor and thereby produce infective virions directly at or near the tumor site.

Accordingly, the invention provides a pharmaceutical formulation(composition) comprising an infective virion or packaging cell line according to the invention in admixture with a pharmaceutically acceptable carrier.

Additionally, the present invention provides methods of making pharmaceutical formulations(compositions), as herein described, comprising mixing an artificial infective virion, containing a molecular chimaera according to the invention as described hereinbefore, with a pharmaceutically acceptable carrier.

The present invention also provides methods of making pharmaceutical formulations(compositions), as herein described, comprising mixing a packaging cell line, containing an infective virion according to the invention as described hereinbefore, with a pharmaceutically acceptable carrier.

Although any suitable compound that can be selectively converted to a cytotoxic or cytostatic metabolite by the enzyme may be utilised, the present invention further provides the use of compounds of Formulas (I) or (II) in the manufacture of a medicament for use in treating cancers capable of expressing VZV TK. In particular for use in treating hepatocellular carcinoma (HCC).

6-Substituted purine arabinoside compounds of Formula (I), their salts, esters, and physiologically functional equivalents thereof are shown hereinbelow:

(I)

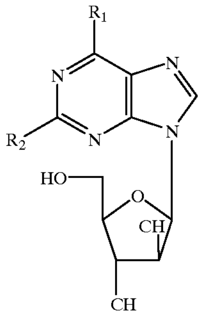

wherein $R_1$ is halo, $C_{1-5}$ alkoxy, halogen-substituted $C_{1-5}$ alkoxy; an amino group which is mono- or di-substituted by $C_{1-5}$ alkyl, $C_{1-5}$ alkyl substituted by one or more fluorine atoms, $C_{3-6}$ cycloalkyl, or a nitrogen-containing heterocycle containing 4–7 carbon atoms and optionally a double bond; and $R_2$ is hydrogen, halo, or amino; are purine-arabino nucleosides which have been reported to have potent activity against human virus infections particularly those caused by varicella zoster virus(VZV) and cytomegalovirus(CMV) (European patent application number 88304813.4 filed May 27, 1988 and published Dec. 7, 1988(Bulletin 88/49) under number 0294114) which is herein incorporated by reference in its entirety.

Certain substituted purine-arabino nucleosides, in particular 9-β-D-arabinofuranosyl-6-methoxy-9-H-purine, 9-β-D- arabinofuranosyl-6-pyrrolidino-9-H-purine, 9-β-D-arabinofuranosyl-6-methylamino-9-H-purine, and 9-β-D-arabinofuranosyl-6-dimethylamino-9-H-purine, have previously been described in J. Org. Chem., 27, 3274–3279 (1962); Cancer Treatment Rep., 60(10), 1567–1584(1976); Tetrahedron, 40(4), 709–713(1984); Canada J. Biochem., 43(1), 1–15(1965); J. Med. Chem., 12, 498–504(1969); J. Biol. Chem., 251(13), 4055–4061(1976); Ann. N. Y. Acad. Sci., 284, 81–90(1977) which are herein incorporated by reference in their entirety.

The following compounds of Formula (I) are preferred compounds to be used in accordance with the present invention;

9-β-D-arabinofuranosyl-6-methylamino-9-H-purine.
9-β-D-arabinofuranosyl-6-dimethylamino-9-H-purine.
9-β-D-arabinofuranosyl-6-methoxy-9-H-purine.
9-β-D-arabinofuranosyl-6-ethoxy-9-H-purine.
9-β-D-arabinofuranosyl-6-iodo-9-H-purine.
9-β-D-arabinofuranosyl-2-amino-6-iodopurine.
9-β-D-arabinofuranosyl-6-pyrrolidino-9-H-purine.
9-β-D-arabinofuranosyl-2-chloro-6-methylamino-9-H-purine.
9-β-D-arabinofuranosyl-6-cyclopropylamino-9-H-purine.
9-β-D-arabinofuranosyl-6-ethylmethylamino-9-H-purine.
9-β-D-arabinofuranosyl-2-amino-6-methoxy-9-H-purine.
9-β-D-arabinofuranosyl-6-n-propoxy-9-H-purine.

Of the above compounds, 9-β-D-arabinofuranosyl-6-methoxy-9-H-purine is especially preferred.

The compounds of Formula (I) to be used in accordance with the present invention may be prepared by methods known in the art for the preparation of the same or similar compounds.

5-Substituted pyrimidine nucleoside compounds of Formula (II), their salts, esters, and physiologically functional equivalents thereof are shown hereinbelow:

(II)

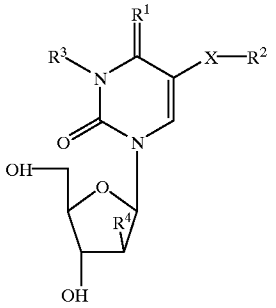

wherein X represents a vinylene or ethynylene group; $R^1$ represents an oxo or imino group; $R^2$ represents a hydrogen atom, $C_{1-2}$ alkyl, $C_{3-4}$ branched or cycloalkyl group (e.g., isopropyl or cyclopropyl); $R^3$ represents a hydrogen atom or an acyl (e.g., $C_{1-4}$ alkanoyl or benzoyl) group optionally substituted, for example, by one or more halogen, alkyl, hydroxy, or alkoxy substituents; and $R^4$ represents a hydrogen atom or a hydroxy group. These pyrimidine nucleosides which are characterized by the presence of an unsaturated grouping in the 5-position, have previously been shown to have anti-VZV activity as well as a relatively low level of toxicity(European patent application number 87310951.6 filed Dec. 14, 1987 and published Jun. 22, 1988(Bulletin 88/25) under number 0272065) which is herein incorporated by reference in its entirety.

Certain 5-substituted nucleosides, in particular 2'-deoxy-5-(1-propynyl)uridine, 2'-deoxy-5-ethynylcytidine, 1-(β-D-arabinofuranosyl)-5-propynyluracil, 1-(β-D-arabinofuranosyl)-5-ethynylcytosine have previously been described in J. Med. Chem., 26(5), 661–666(1983); J. Med. Chem., 26(9), 1252–1257(1983); Antimicrobial Agents Chemother., 17(6), 1030–1031(1980); Nucleic Acids Symp. Ser., 9, 103–106(1981); Biochem. Pharmacol., 32(4), 726–729(1983) which are herein incorporated by reference in their entirety.

It will be appreciated that when $R^3$ is not an acyl group, the compounds of Formula (II) may exist in their tautomeric form.

The following compounds of Formula (II) are preferred compounds to be used in accordance with the present invention;

2'-Deoxy-5-(1 -propynyl)uridine.
2 '-Deoxy-5-ethynylcytidine.
3-N-Benzoyl-2'-deoxy-5-ethynyluridine.
1 -(β-D-Arabinofuranosyl)-5-ethynyluracil.
2'-Deoxy-5-(1-propynyl)cytidine.
1-(β-D-Arabinofuranosyl)-5-propynylcytosine.
3-N-Benzoyl-2'-deoxy-5-propynyluridine.
1-(β-D-Arabinofuranosyl)-5-propynyluracil.
1-(β-D-Arabinofuranosyl)-5-ethynylcytosine.
1-(β-D-Arabinofuranosyl)-3-N-benzoyl-5-propynyluracil.
1-(β-D-Arabinofuranosyl )-3-N-benzoyl-5-ethynyluracil.
3-N-Benzoyl-2'-deoxy-5-vinyluridine.
1-(β-D-Arabinofuranosyl)-3-N-benzoyl-5-vinyluracil.

A particularly preferred compound of Formula (II) is 1-(β-D-arabinofuranosyl)-5-propynyluracil.

The compounds of Formula (II) to be used according to the invention may be prepared by any of the methods known in the art for the preparation of the same or similar compounds(e.g., see Robins M. J., and Barr, P. J., J. Org. Chem., 43, 1854–1862(1983) which is herein incorporated by reference in its entirety).

The abovementioned purine arabinosides and pyrimidine nucleosides also include the pharmaceutically acceptable derivatives of such compounds, i.e., any pharmaceutically acceptable salt, ester, or salt of such ester, or any other compound which, upon administration to a human subject, is capable of providing (directly or indirectly) the active metabolite or residue thereof. Preferably, the compound is orally active.

The pharmaceutically acceptable esters of the above compounds of Formula (I) are particularly preferred since they are capable of providing high levels of the parent compound in the plasma of a subject after oral administration. Particularly preferred derivatives of compounds of Formula (I) include mono-, di-, or tri-esters of the arabino-sugar residue substituted at the 2'-, 3'-, and 5'-positions of said residue.

Such preferred esters include carboxylic acid esters in which the non-carbonyl moiety of the ester grouping is selected from straight or branched chain alkyl(e.g., n-propyl, t-butyl, n-butyl), alkoxyalkyl(e.g., methoxymethyl), aralkyl (e.g., benzyl), aryloxyalkyl(e.g., phenoxymethyl), aryl(e.g., phenyl) optionally substituted by halogen, $C_{1-4}$ alkyl or $C_{1-4}$ alkoxy, nitro or amino; sulfonate esters such as alkylsulfonyl, or arylsulfonyl(e.g., methanesulfonyl or tosylsulfonyl); amino acid esters(e.g., L-valyl); and mono-, di-, or tri-phosphate esters. Pharmaceutically acceptable salts of these esters include sodium, potassium, $NR_4^+$ where R=H or $C_{1-6}$ alkyl, and acid addition salts. In the above ester groups, the alkyl groups(including those in alkoxy groupings) contain 1 to 12 carbon atoms and the aryl groups are preferably phenyl.

The following esters and ethers are preferred compounds to be used in accordance with the present invention:

9-(5-O-Benzoyl-β-D-arabinofuranosyl)-6-methoxy-9-H-purine.

6-Methoxy-9-[5-O-(4-methylphenylsulfonyl)-β-D-arabinofuranosyl]-9-H-purine.

6-Methoxy-9-(5-O-methylsulfonyl-β-D-arabinofuranosyl)-9-H-purine.

9-( 5-O-(4-Methylbenzoyl)-β-D-arabinofuranosyl)-6-methoxy-9-H-purine.

9-(5-O-(4-Chlorobenzoyl)-β-D-arabinofuranosyl)-6-methoxy-9-H-purine.

9-(5-O-(4Methoxybenzoyl)-β-D-arabinofuranosyl)-6-methoxy-9-H-purine.

6-Methoxy-9-(5-O-phenylacetyl-β-D-arabinofuranosyl)-9-H-purine.

6-Methoxy-9-(5-O-phenyloxyacetyl-β-D-arabinofuranosyl)-9-H-purine.

6-Methoxy-9-(5-O-methoxyacetyl-β-D-arabinofuranosyl)-9-H-purine.

9-(5-O-(4-Nitrobenzoyl)-β-D-arabinofuranosyl)-6-methoxy-9-H-purine.

6-Methoxy-9-(5-O-pentanoyl-β-D-arabinofuranosyl)-9-H-purine.

9-[5-O-(4-Aminobenzoyl)-β-D-arabinofuranosyl]-6-methoxy-9-H-purine.

6-Methoxy-9-(5-O-propionyl-β-D-arabinofuranosyl)-9-H-purine.

9-(5-O-Butanoyl-β-D-arabinofuranosyl)-6-methoxy-9-H-purine.

9-[5-O-(2,2-Dimethylpropionyl)-β-D-arabinofuranosyl]-6-methoxy-9-H-purine.

9-(5-O-Acetyl-β-D-arabinofuranosyl)-6-methoxy-9-H-purine.

6-Methoxy-9-[5-O-(2-methypropionyl)-β-D-arabinofuranosyl]-9-H-purine.

6-Methoxy-9-[2-O-(2,2-dimethylpropionyl)-β-D-arabinofuranosyl]-9-H-purine.

6-Methoxy-9-[(2,3,5-tri-O-acetyl)-D-arabinofuranosyl]-9-H-purine.

6-Methoxy-9-(2-O-pentanoy-β-D-arabinofuranosyl)-9-H-purine.

9-(2-O-Butanoyl-β-D-arabinofuranosyl)-6-methoxy-9-H-purine.

6-Methoxy-9-[2-O-(2-methylpropionyl)-β-D-arabino-furanosyl]-9-H-purine.

9-(3-O-Benzoyl-β-D-arabinofuranosyl)-6-methoxy-9-H-purine.

9-(2,3-Anhydro-β-D-Iyxofuranosyl)-6-methoxy-9-H-purine.

6-Methoxy-9-[(2-O-(4-methoxybenzoyl))-β-D-arabinofuranosyl]-9-H-purine.

6-Methoxy-9-[(2-O-(4-methylbenzoyl))-β-D-arabinofuranosyl]-9-H-purine.

9-[2-O-(4-Chlorobenzoyl)-β-D-arabinofuranosyl]-6-methoxy-9-H-purine.

6-Methoxy-9-[3,5-O-(1,1,3,3-tetraisopropyl-1,3-disiloxan-1,3-diyl)-β-D-arabinofuranosyl]-9-H-purine.

6-Methoxy-9-[2-O-(2-aminobenzoyl)-β-D-arabinofuranosyl]-9-H-purine.

6-Methoxy-9-[2-(4-methylbenzoyl)-3,5-O-(1,1,3,3-tetra-isopropyldisiloxan-1,3-diyl)-β-D-arabinofuranosyl]-9-H-purine.

6-Methoxy-9-[2-(4-methoxybenzoyl)-3,5-O-(1,1,3,3-tetra-isopropyldisiloxan-1,3-diyl)-β-D-arabinofuranosyl]-9-H-purine.

9-[2-(4-Chlorobenzoyl)-3,5-O-(1,1,3,3-tetra-isopropyldisiloxan-1,3-diyl)-β-D-arabinofuranosyl]-6-methoxy-9-H-purine.

5'-Monophosphate ester of 9-β-D-arabinofuranosyl-6-dimethylamine-9H-purine.

6-Methoxypurine arabinoside 5'-monophosphate.

6-Methoxypurine arabinoside 5'-triphosphate.

6-Dimethylamino-9-[(2-O-valeryl)-β-D-arabinosyl]-9H-purine.

6-Dimethylamino-9-(2,3,5-triacetyl-β-D-arabinosyl)-9H-purine.

Physiologically acceptable salts and esters of compounds of Formula (I) to be used according to the present invention may be prepared in conventional manner. For example, esters may be prepared by esterification of the parent compound with an appropriate acyl halide or anhydride. Alternatively, the esters may be prepared by displacing the appropriate leaving group(e.g., halide) with an appropriate carboxylic acid or by opening an appropriate anhydro nucleoside of the parent compound with an appropriate carboxylic acid or salt thereof.

Also pharmaceutically acceptable salts and esters of compounds of Formula (II) especially the diacetate of 2'-deoxy-5-ethynylcytidine, namely 2'-deoxy-3',5'-di-O-acetyl-5-ethynylcytidine, may be used in accordance with the present invention.

Although any suitable compound that can be selectively converted to a cytotoxic or cytotostatic metabolite by the enzyme cytosine deaminase may be utilised, the present invention further provides the use of 5-fluorocytosine in the manufacture of a medicament for use in treating cancers capable of expressing cytosine deaminase. In particular for use in treating hepatocellular carcinoma (HCC), colorectal carcinoma(CRC), metastatic colorectal carcinoma, or hepatic CRC metastases.

Any agent that can potentiate the antitumor effects of 5-FU can also potentiate the antitumor effects of 5-fluorocytosine(5-FC) since, when used according to the present invention, 5-FC is selectively converted to 5-FU. According to another aspect of the present invention, agents such as leucovorin and levemisol, which can potentiate the antitumor effects of 5-FU, can also be used in combination with 5-FC when 5-FC is used according to the present invention. Other agents which can potentiate the antitumor effects of 5-FU are agents which block the metabolism 5-FU. Examples of such agents are 5-substituted uracil derivitives, for example, 5-ethynyluracil and 5-bromvinyluracil(PCT/GB91/01650(WO 92/04901); Cancer Research 46, 1094, 1986 which are incorporated herein by reference in their entirety). Therefore, a further aspect of the present invention is the use of an agent which can potentiate the antitumor effects of 5-FU, for example, a 5-substituted uracil dervitive such as 5-ethynyluracil or 5-bromvinyluracil in combination with 5-FC when 5-FC is used according to the present invention. The present invention further includes the use of agents which are metabolised in vivo to the corresponding 5-substituted uracil derivatives described hereinbefore(see Biochemical Pharmacology 38, 2885, 1989 which is incorporated herein by reference in its entirety) in combination with 5-FC when 5-FC is used according to the present invention.

5-Fluorocytosine is readily available(e.g., United States Biochemical, Sigma) and well known in the art. Leucovorin and levemisol are also readily available and well known in the art.

Two significant advantages of the enzyme/prodrug combination of cytosine deaminase/5-fluorocytosine and further aspects of the invention are the following:

1. The metabolic conversion of 5-fluorocytosine (5-FC) by cytosine deaminase produces 5-fluorouracil (5-FU). 5-FU is the drug of choice in the treatment of many different types of cancers, such as colorectal carcinoma.
2. The 5-FU that is selectively produced in one cancer cell can diffuse out of that cell and be taken up by both non-facilitated diffusion and facilitated diffusion into adjacent cells. This produces a neighboring cell killing effect. This neighbor cell killing effect alleviates the necessity for delivery of the therapeutic molecular chimera to every tumor cell. Rather, delivery of the molecular chimera to a certain percentage of tumor cells can produce the complete eradication of all tumor cells.

The amounts and precise regimen in treating a mammal, will of course be the responsibility of the attendant physician, and will depend on a number of factors including the type and severity of the condition to be treated. However, for HCC or hepatic metastatic CRC, an intrahepatic arterial infusion of the artificial infective virion at a titer of between $2\times10^5$ and $2\times10^7$ colony forming units per mL (CFU/mL) infective virions is suitable for a typical tumour. Total amount of virions infused will be dependent on tumour size and are preferably given in divided doses.

Likewise, the packaging cell line is administered directly to a tumor in an amount of between $2\times10^5$ and $2\times10^7$ cells. Total amount of packaging cell line infused will be dependent on tumour size and is preferably given in divided doses.

Prodrug treatment—Subsequent to infection with the infective virion, compounds according to the invention, which are described by Formulas (I) and (II), are administered that specifically require VZV TK activity for the critical phosphorylation step in anabolism to generate cytotoxic or cytostatic metabolites. These prodrug compounds, which are subsequently converted to cytotoxic or cytostatic metabolites in the target cells, are preferably purine arabinosides or pyrimidine nucleosides. Most preferably 9-β-D-arabinofuranosyl-6-methoxy-9H-purine and 1-(β-D-arabinofuranosyl)-5-propynyluracil. Likewise, certain cytosine compounds(prodrugs of 5-FU) are converted by cytosine deaminase to cytoxic or cytostatic metabolites(e.g., 5-fluorocytosine is converted to 5-fluorouracil) in target cells. The abovementioned prodrug compounds are administered to the host(e.g., mammal or human) between six hours and ten days, preferably between one and five days, after administration of the infective virion.

The dose of compound, as described by Formulas (I) and (II), to be given will advantageously be in the range 0.1 to 250 mg per Kgm body weight of recipient per day, preferably 0.1 to 100 mg per Kgm bodyweight of recipient per day, more preferably 1 to 40 mg per Kgm bodyweight of recipient per day, and most preferably 15–40 mg per Kgm body weight of recipient per day.

The dose of 5-fluorocytosine to be given will advantageously be in the range 10 to 500 mg per Kgm body weight of recipient per day, preferably 50 to 500 mg per Kgm bodyweight of recipient per day, more preferably 50 to 250 mg per Kgm bodyweight of recipient per day, and most preferably 50 to 150 mg per Kgm body weight of recipient per day. The mode of administration of 5-FC in humans are well known to those skilled in the art. Oral administration and/or constant intravenous infusion of 5-FC are anticipated by the instant invention to be preferable.

The doses and mode of administration of leucovorin and levemisol to be used in accordance with the present invention are well known or readily determined by those clinicians skilled in the art of oncology.

The dose and mode of administration of the 5-substituted uracil derivitives can be determined by the skilled oncologist. Preferably, these derivatives are given by intravenous injection or orally at a dose of between 0.01 to 50 mg per kilogram body weight of the recipient per day, particularly 0.01 to 10 mg per kilogram body weight per day, and more preferably 0.01 to 0.4 mg per kilogram bodyweight per day depending on the deriviative used. An alternative preferred administration regime is 0.5 to 10 mg per kilogram body weight of recipient once per week.

The invention also provides a method of treating a host (e.g., mammal or human) in need of anticancer treatment which comprises administering to the host, a molecular chimaera capable of being selectively activated in the cells of the host to express an enzyme, and subsequently administering an agent which is converted in the cells by the enzyme to an agent which is cytotoxic or cytostatic to the cells. Preferably the molecular chimaera expresses the enzyme CD and the agent which is converted by the enzyme is 5-FC.

The invention also comprises a method of killing cells in vitro which comprises administering to the cells, a molecular chimaera capable of being selectively activated in the cells to express an enzyme, and subsequently administering an agent which is converted in the cells by the enzyme to an agent which is cytotoxic or cytostatic to the cells. Preferably the molecular chimaera expresses the enzyme CD and the agent which is converted by the enzyme is 5-FC.

The invention further provides a method of treating a host in need of anticancer treatment comprising administering to the host an infective virion or a packaging cell line as described hereinbefore. Namely, the packaging cell line comprises an infective virion encapsidating a retroviral shuttle vector comprising a molecular chimaera, the chimaera comprising a transcriptional regulatory sequence which is selectively activated in cells of the host and operatively linked to a gene encoding a heterologous enzyme; in an amount sufficient to transform the cells so as to express the enzyme, and subsequently administering to the host an amount of a compound which is selectively metabolised in the cells by the enzyme to a cytotoxic or cytostatic metabolite.

The following examples serve to illustrate the present invention but should not be construed as a limitation thereof.

EXAMPLE 1

Construction of Transcriptional Regulatory Sequence of Albumin/VZV Thymidine Kinase Molecular Chimaera An approximately 1,381 bp AccI/Nde 1 DNA fragment (all restriction enzymes obtained from either Bethesda Research Laboratories, Gaithersburg Md., USA; New England Biolabs, Mass., USA; or Promega, Madison, Wis., USA; all enzymatic reactions performed as specified by the supplier) containing the coding sequence and polyadenylation signal of the VZV TK gene was purified by electroelution using an elutrap electrophoresis chamber (by Schleicher and Schuell, Keene, N.H., USA) from a restriction endonuclease digestion of an approximately 4,896 bp plasmid, designated 22TK, containing an approximately 2,200 bp EcoRI/BamHI fragment of the VZV TK genome (Sawyer M. H., Ostrove J. M., Felser J. M. Virology 149 1–9 (1986); supplied by J. Ostrove, NIH, Bethesda, Md.). The purified DNA fragment contains the entire VZV TK coding sequence and polyadenylation signal, but does not include any VZV TK promotional elements (see FIGS. 2A and 2B)(SEQ ID NO:1).

The 5' overhanging ends of the purified 1,381 bp AccI/NdeI VZV TK fragment were made blunt by treatment with the Klenow fragment of *E. coli* DNA polymerase I (Bethesda Research Laboratories, Gaithersburg, Md., USA) and deoxynucleotide triphosphates (dNTPs).

An approximately 5,249 bp plasmid, designated 2335A-1, containing approximately 2,300 bp of a ALB E/P sequence was obtained from Richard Palmiter (University of Washington, Seatle, Wash. USA). This construct contains sequences necessary for liver-specific expression but lacks nonessential intervening sequences. A unique BamH I restriction endonuclease recognition site is present at +23 relative to the start of transcription. 2335A-1 was digested with the restriction endonuclease BamH I and the 5' overhanging ends were made blunt by treatment with Klenow and dNTPs as described above.

Figure 5:
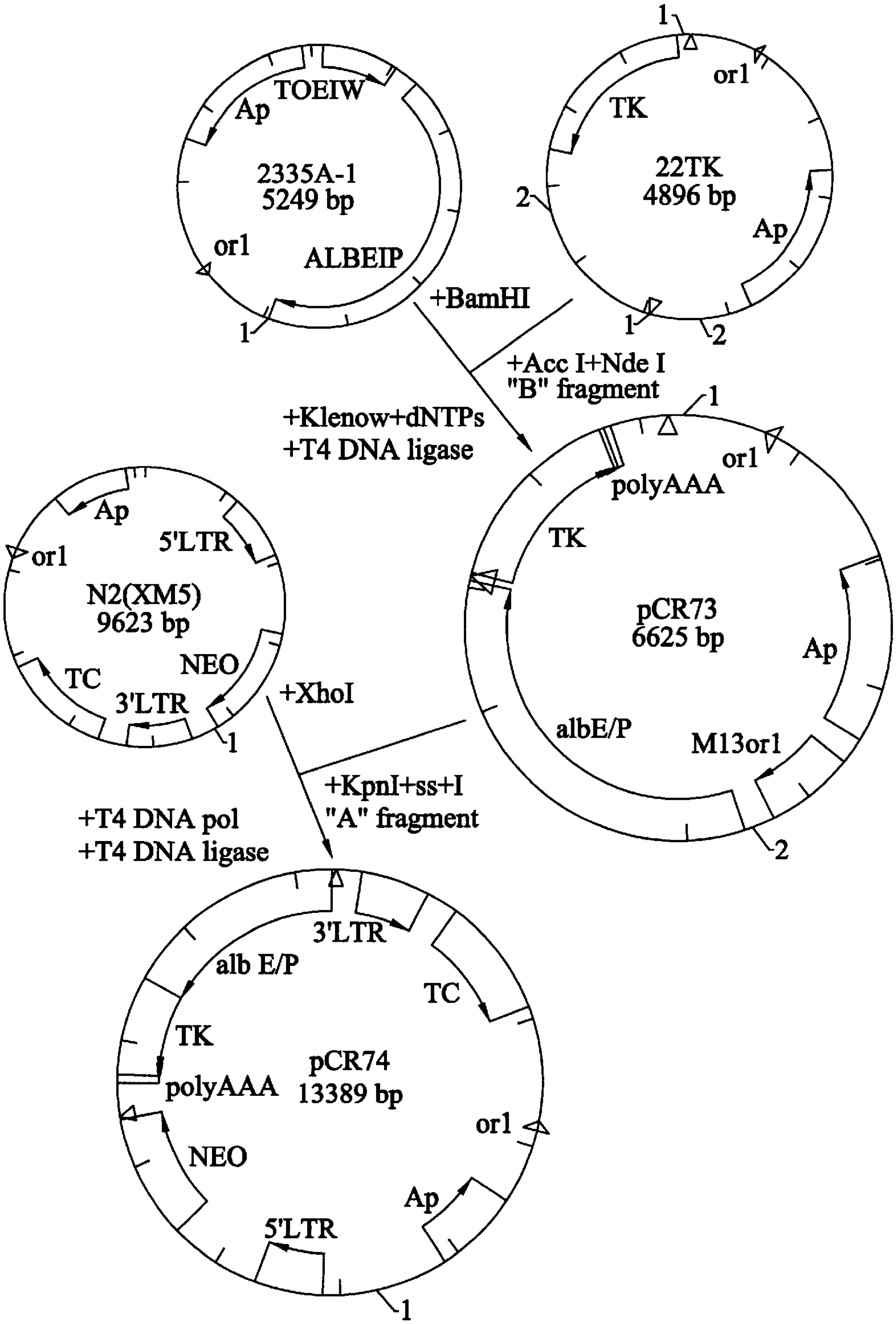
FIG. 5: Flow chart showing the construction of pCR74.

The ALB E/P VZV TK chimaera was constructed by ligating the blunt ended AccI-NdeI fragment containing the VZV TK coding and polyadenylation sequences into the blunt ended BamH I site of 2335A-1 creating pCR73 using T4 DNA ligase (Bethesda Research Laboratories, Gaithersburg, Md.) (FIG. 5). Similar to all ligations described, the orientation of the ligated fragments was determined by restriction endonuclease digestions by methods well known in the art. Similar to all plasmids described in all examples, pCR73 contains essential sequences required for replication in bacteria and suitable for amplification by methods well known in the art. The ALB E/P VZV TK chimaera was purified by electroelution from pCR73 as an approximately 3880 bp SstI/KpnI restriction endonuclease fragment (FIG. 5). The 3' overhanging ends were made blunt by treatment with T4 DNA polymerase and dNTPs. This SstI/KpnI blunt ended restriction fragment was subsequently introduced into a Moloney murine leukemia virus retroviral shuttle vector system (see below, Example 3).

pCR73 was deposited at the American Type Culture Collection, Rockville, Md. USA(ATTC) on Aug. 18, 1989 under the Budapest Treaty with Accession No. ATCC68077.

EXAMPLE 2

Figure 6A:
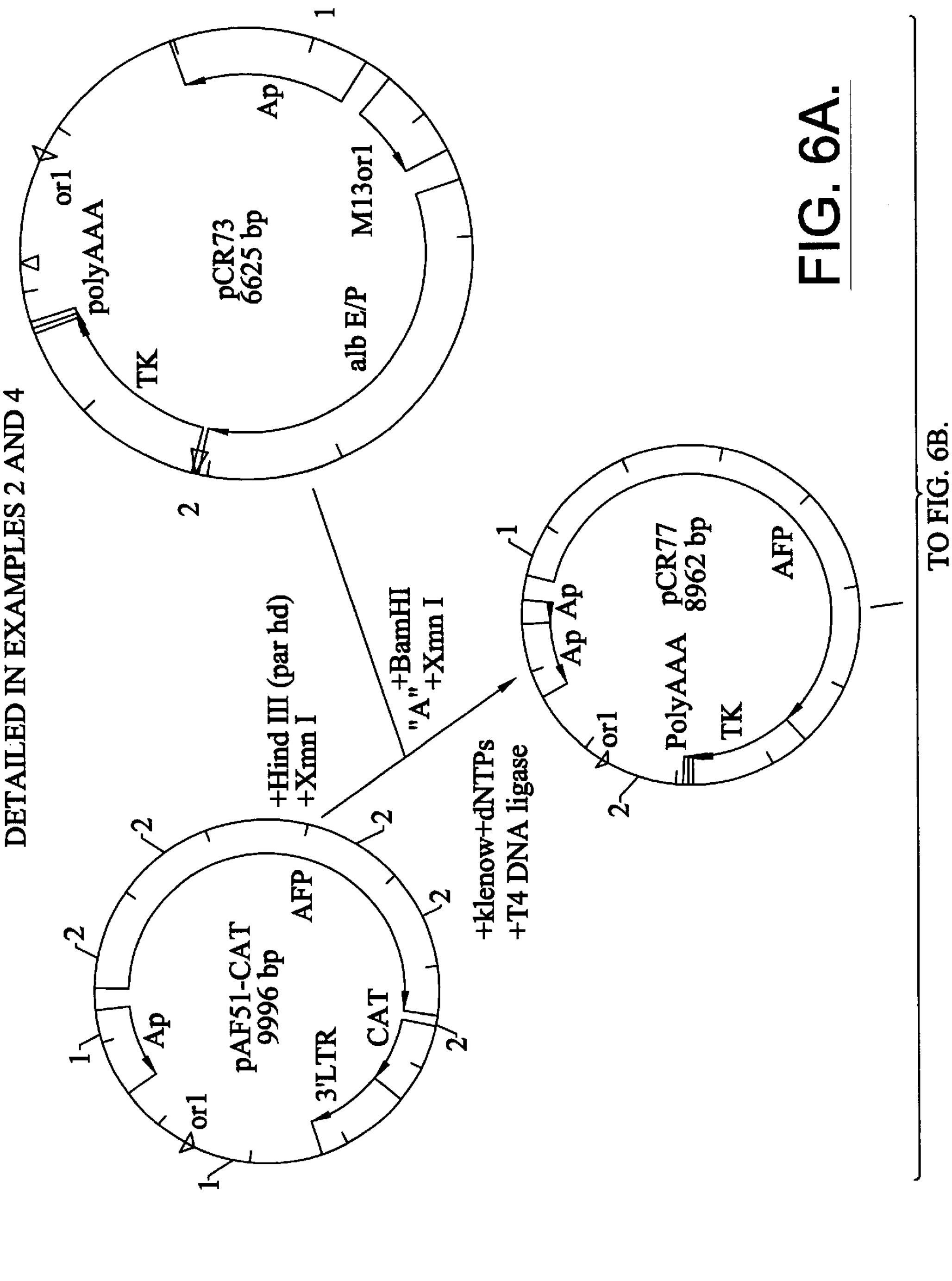
FIG. 6: Flow chart showing the construction of pCR78.
Figure 6B:
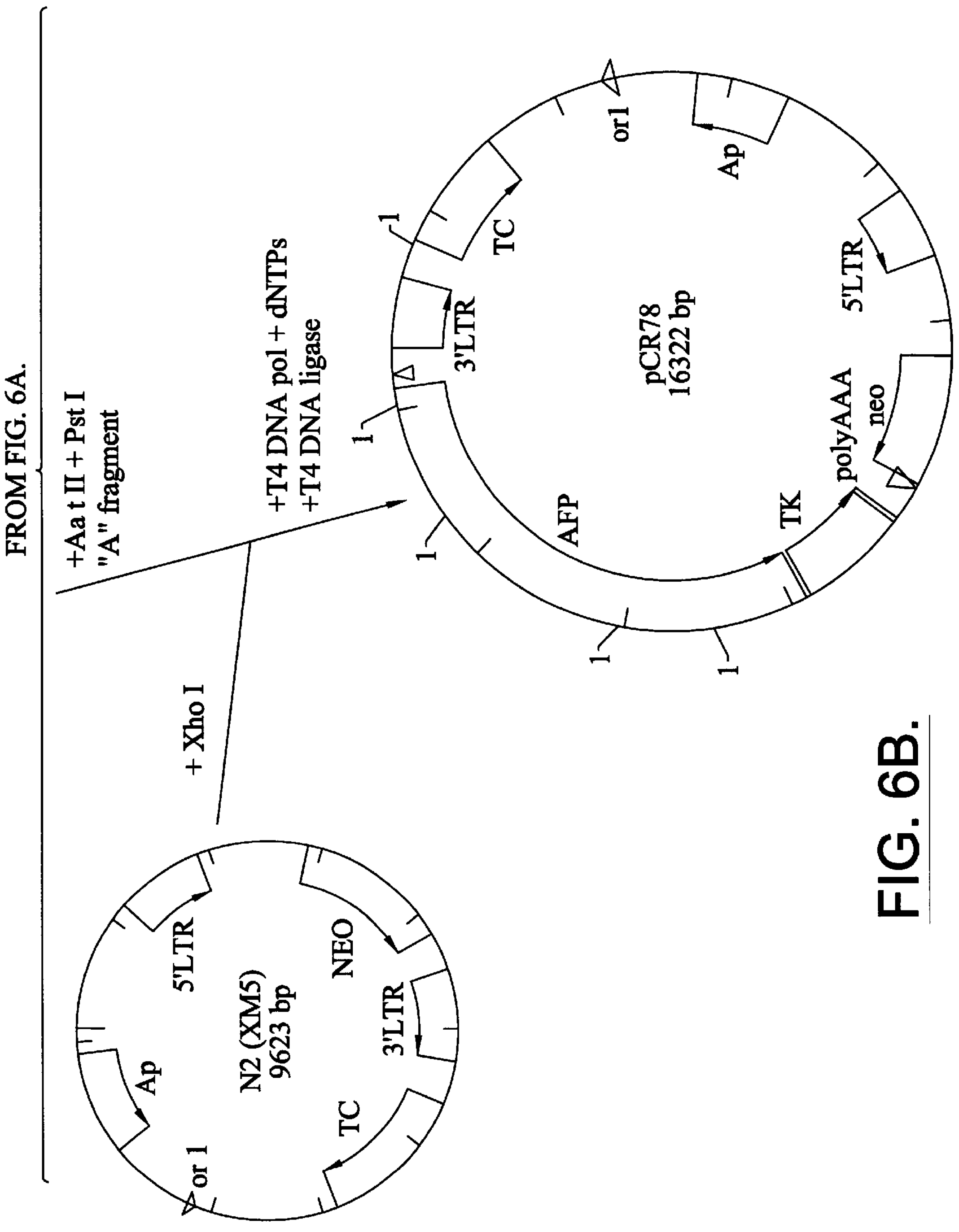

Construction of Transcriptional Regulatory Sequence of Alpha-fetoprotein/VZV Thymidine Kinase Molecular Chimaera The VZV thymidine kinase coding sequence and polyadenylation site was isolated as an approximately 3,300 bp BamHI-XmnI restriction endonuclease fragment of pCR73 (FIG. 6). The 5' overhanging end of the BamHI restriction endonuclease site was made blunt by treatment with Klenow and dNTPs. This DNA fragment contains the complete coding sequence and the polyadenylation site of the VZV TK gene but does not contain any enhancer or promoter sequences. An approximately 9,996 bp plasmid, pAF5.1-CAT, containing an approximately 5,100 bp of human AFP 5' flanking DNA was obtained from T.Tamaoki, Univ. of Calgary, Canada. A DNA fragment spanning from approximately −5.1 kb to +29 of the human AFP gene was isolated from pAF5.1-CAT by digestion with XmnI and partial digestion with HindIII. This XmnI/HindII fragment was ligated to the BamHI/XmnI VZV TK fragment using T4 DNA ligase to form pCR77 (FIG. 6). The AFP E/P VZV TK chimera was purified by electroelution from pCR77 as an approximately 6,699 bp Aat II /PstI restriction endonuclease fragment. This fragment was then treated with T4 DNA polymerase and dNTPs as Example 1 to produce a blunt end restriction fragment.

pCR77 was deposited at the ATCC on Aug. 18, 1989, under the Budapest Treaty with Accession No. ATCC68079.

EXAMPLE 3

Construction of a Retroviral Shuttle Vector Construct Containing the Molecular Chimaera of Example 1

The retroviral shuttle vector, pCR74, containing the ALB E/P VZV TK chimaera was constructed by ligating the purified SstI/KpnI blunt ended fragment of pCR73 into a Moloney murine leukemia retroviral vector designated N2(XM5) (Eglitis M. A., Kantoff P., Gilboa E., Anderson W. F. Science 230, 1395–1398 (1985)) obtained from S. Karrlson, NIH, Bethesda, Md., USA. N2(XM5) was digested with the restriction endonuclease XhoI and the 5' overhanging ends were made blunt by treatment with both Klenow and dNTPs prior to the ligation to the pCR73 SstI/KpnI fragment using T4 DNA ligase (FIG. 5).

The retroviral shuttle vector pCR74 containing the ALB E/P VZV TK chimaera has been characterised by restriction endonuclease mapping and DNA sequencing to confirm the primary sequence. The sequence flanking the junction of the ALB E/P to the VZV TK sequences is shown in FIG. 7(SEQ ID NO:2).

pCR74 was deposited at the ATCC on Aug. 18, 1989 under the Budapest Treaty with Accession No. ATCC68078.

EXAMPLE 4

Construction of a Retroviral Shuttle Vector Construct Containing the Molecular Chimaera of Example 2

The retroviral shuttle vector pCR78 (FIG. 6) was constructed by ligating a purified AatII/PstI fragment of pCR77 containing the AFP E/P VZV TK chimaera into N2(XM5), which was digested with XhoI and made blunt ended with T4 DNA polymerase and dNTPs as described in Example 3. The retroviral shuttle vector pCR78 containing the AFP E/P VZV TK chimaera has been characterised by restriction endonuclease mapping and DNA sequencing to confirm the primary sequence. The sequence flanking the junction of AFP E/P to the VZV TK sequence is shown in FIG. 8(SEQ ID NO:3).

pCR78 was deposited at the ATCC on Aug. 18, 1989 under the Budapest Treaty with Accession No. ATCC68080.

EXAMPLE 5

Virus Production

The packaging cell line called PA317 obtained from ATCC, (ATCC CRL 9078), which has been previously described, has three alterations contained within the 5' LTR, psi regulatory sequence, and 3' LTR (Miller A. D., Buttimore C. Mol. Cell. Biol. 6 2895–2902 (1986)). The artificial retroviral constructs described in Examples 3 and 4 were placed into the packaging cell line by electroporation or infection. For electroporation, 20 ug of linearized plasmid DNA was electroporated into 2 million PA317 cells in phosphate buffered sucrose using 280 volts, 25 microfarads of capacitance in a total volume of 0.8 mLs. There was obtained at least about 150 G418 resistant colonies/20 ug plasmid DNA/2 million PA317 cells. For infection, 20 ug of linearized plasmid DNA was electroporated into 2 million ecotropic packaging cells, such as Psi 2 cells. Two days later, the culture supernatant was used to infect the amphotropic packaging cell line PA317 and G418 resistant colonies isolated. For both electroporation and infection techniques, G418 resistant colonies were single cell cloned by the limiting dilution method, analysed by Southern blots, and titered in NIH 3T3 cells(ATCC) to identify the highest producer of full-length virus. For PA317 cells containing pCR74, 17 single-cell clones were isolated and DNA was extracted from 10 of these clones. Extensive Southern blot analysis using different restriction endonuclease enzymes and NEO and VZV TK sequences as radioactive hybridization probes was performed on these 10 DNA samples. Out of the 10 clones analysed, two showed no evidence of truncation and are considered full length. For PA317 cells containing pCR78, 29 single-cell clones were isolated and DNA was obtained from 25 clones. Extensive Southern blot analysis using different restriction endonuclease enzymes and AFP, NEO, and VZV TK sequences as radioactive hybridisation probes was performed on these 25 samples. Out of the 25 clones analysed, 5 showed no evidence of truncation and are considered full length. Each packaging cell line containing a full length viral sequence was titered in NIH 3T3 cells, which were thymidine kinase minus/minus, using standard techniques.

EXAMPLE 6

Infection of Human Hepatoma Cell Lines (Positive Controls) with Full Length Infective Virions of Example 5 Containing ALB/VZV TK or AFP/VZV TK with Subseauent Measurements of VZV TK Activity, ara-ATP Production and Drug Sensitivity The replication-defective, full-length, artificial retroviruses containing the ALB/VZV TK chimaera or AFP/VZV TK chimaera were used to infect human hepatoma cell lines called HepG2 (ATCC HB 8065) and HuH7(provided by B. Mason, Fox Chase Cancer Center, Philadelphia, Pa.). Following infection and selection on 1 mg Geneticin/mL, the cells were assayed for VZV TK activity(Geneticin(antibiotic G418 sulphate) is a registered trademark of GIBCO). In addition, HepG2 cells were incubated in the presence of ($^3$H)-labeled 9-β-D-arabinofuranosyl-6-methoxy-9H-purine (designated as araM in the following tables and figures) with subsequent measurement of ara-ATP formation. Finally, HepG2 and HuH7 cells were cultured in the presence of the abovementioned compound and the $IC_{50}$ (50% growth inhibition) was determined. Cells infected with no virus or N2 virus act as control samples for these experiments. The N2 viruses contain no VZV TK genetic material.

Table 1 demonstrates that the HepG2 hepatoma cells infected with either pCR74- or pCR78-containing viruses have approximately 700 fold or 33 fold greater VZV TK activity, respectively, compared to control cells. The HuH7 hepatoma cells infected with either pCR74- or pCR78-containing viruses have approximately 218-fold and 15-fold greater VZV TK activity, respectively, compared to control cells.

Figure 9A:
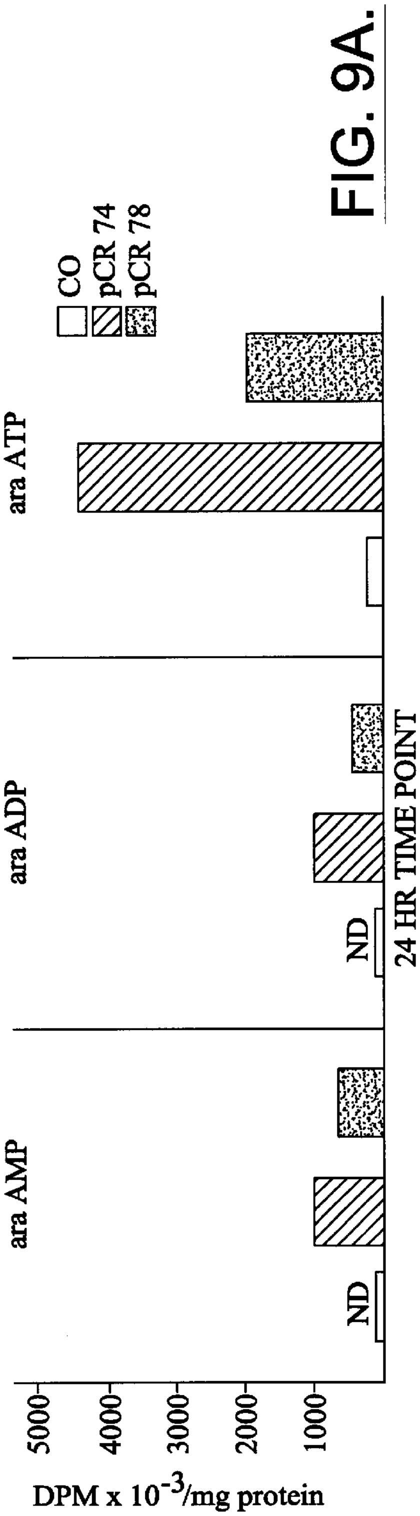
FIG. 9: Production of ara-ATP with cells infected with controls, pCR74, and pCR78.
Figure 9B:
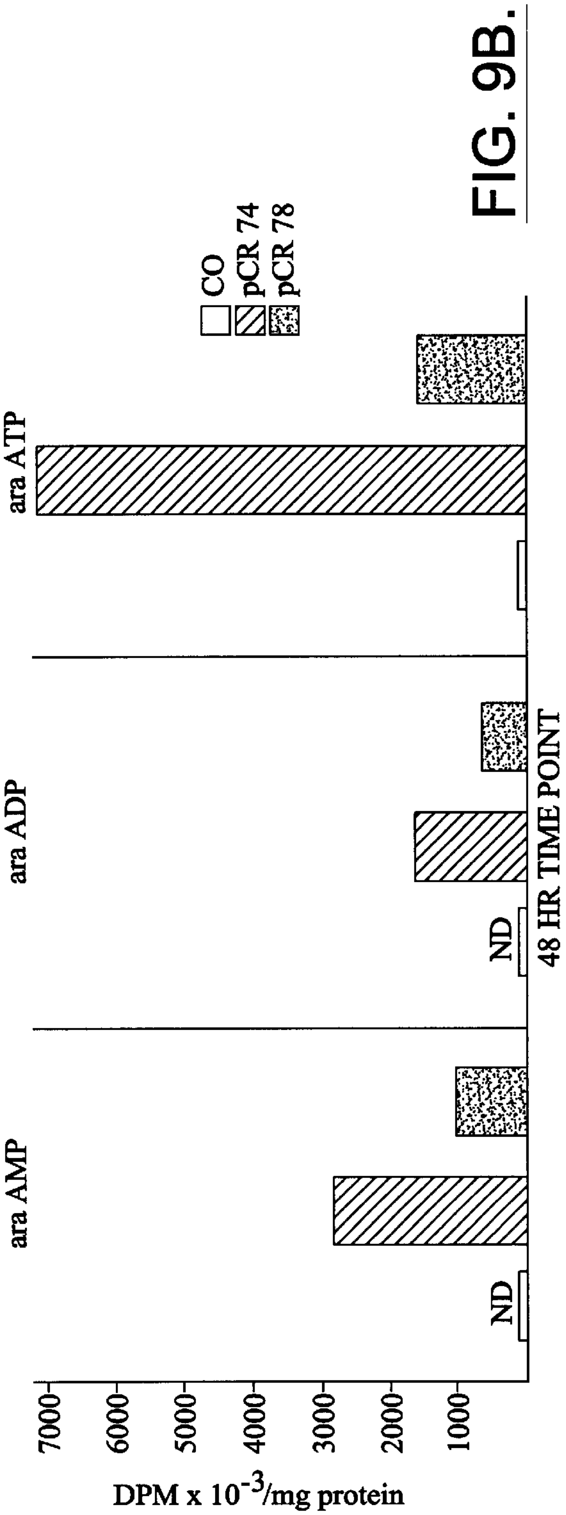

9-β-D-arabinofuranosyl-6-methoxy-9H-purine(designated as araM) can be selectively monophosphorylated by VZV TK with subsequent anabolism to cytotoxic ara-ATP. FIG. 9 demonstrates that HepG2 cells which were infected with either pCR74-or pCR78-containing viruses and incubated in the presence of ($^3$H)-labelled 9-β-D-arabinofuranosyl-6-methoxy-9H-purine had significant amounts of cytotoxic (3H)-ara-ATP formation.

HepG2 and HuH7 cells infected with the replication-defective, full-length, artificial retroviruses containing the ALB/VZV TK chimaera(pCR74) or AFP/VZV TK(pCR78) chimaera were incubated in the presence of varying amounts of 9-β-D-arabinofuranosyl-6-methoxy-9H-purine for 5 days and growth inhibition was determined as measured by cell number and DNA content.

Table 2 demonstrates that the $IC_{50}$ (50% growth inhibition) of 9-β-D-arabinofuranosyl-6-methoxy-9H-purine(araM) is greater than 2,000 uM in control and N2 infected HepG2 cells. The $IC_{50}$ of araM is approximately 1621 uM in control HuH7 cells. In HepG2 cells infected with the replication-defective, full-length, artificial retroviruses containing the ALB/VZV TK chimaera(pCR74) or AFP/VZV TK(pCR78) chimaera, the $IC_{50}$ values were 6.5 uM and 78 uM, respectively. Single cell cloning of HepG2 cells containing the AFP/VZV TK(pCR78) chimaera indicated that the $IC_{50}$ levels of 9-β-D-arabinofuranosyl-6-methoxy-9H-purine can be further decreased to approximately 40 uM. In HuH7 cells infected with the replication-defective, full-length, artificial retroviruses containing the ALB/VZV TK chimaera(pCR74) or AFP/VZV TK(pCR78) chimaera, the $IC_{50}$ values were 11 uM and 76 uM, respectively.

EXAMPLE 7

Selectivity of Expression of VZV TK

Four human, nonhepatoma cell lines were infected with replication-defective, full-length, artifical retroviruses containing the ALB/VZV TK chimaera(pCR74) or AFP/VZV TK chimaera(pCR78). These cell lines were WiDR (ATCC CCL218), MCF7 (ATCC HTB22), Detroit 555 (ATCC CCL110), and SW480 (ATCC CCL228). Subsequent to infection and selection on Geneticin(antibiotic G418 sulphate; registered trademark of GIBCO), these cells were assayed for VZV TK activity and growth inhibition in the presence of 9-β-D-arabinofuranosyl-6-methoxy-9H-purine, as described above. There was no increase in VZV TK activity or drug sensitivity to 9-D-arabino-furanosyl-6-methoxy-9H-purine in these four nonhepatoma cell lines infected with replication-defective, full-length, artificial retroviruses containing the ALB/VZV TK chimaera(pCR74) or AFP/VZV TK chimaera(pCR78) compared to parental cell lines which were not infected. This demonstrates the selectivity of expression for VZV TK in hepatoma versus nonhepatoma cells.

EXAMPLE 8

Figure 10:
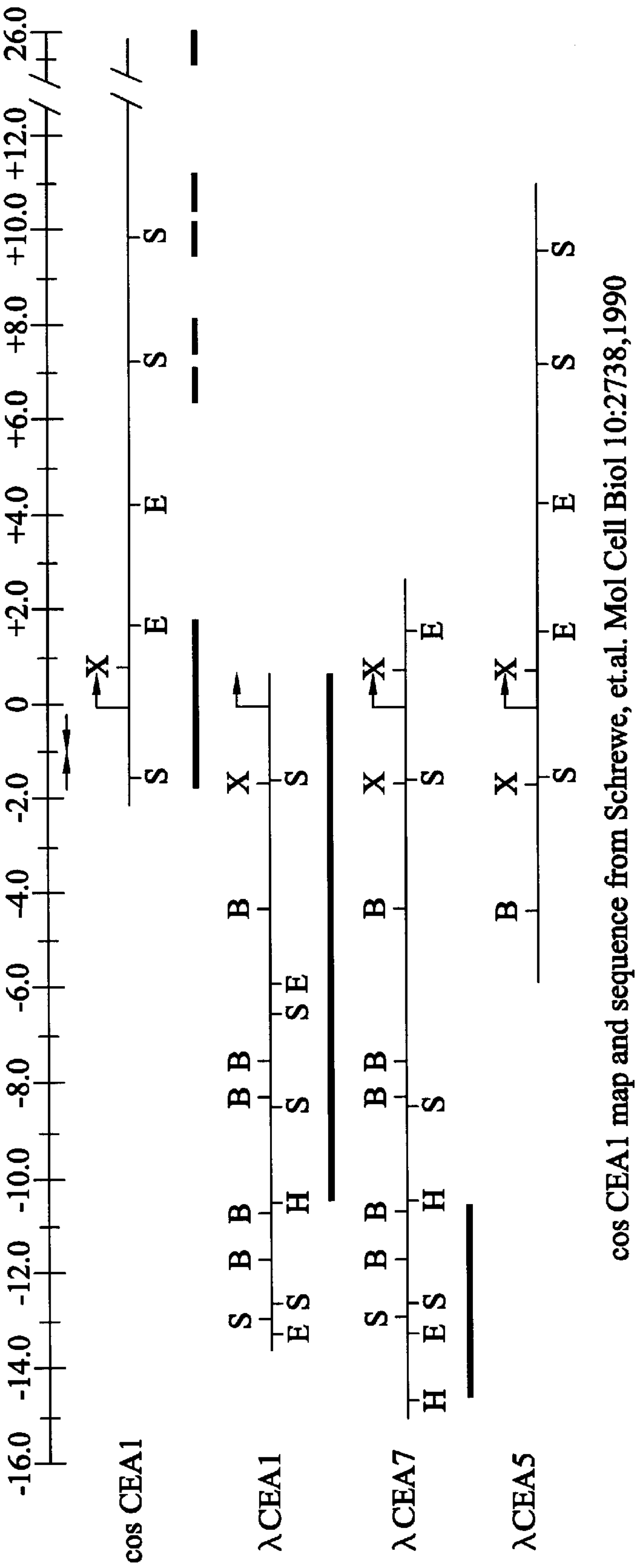
FIG. 10: Diagram of CEA phage clones. The overlapping clones lambdaCEA1, lambdaCEA7, and lambdaCEA5 represent an approximately 26 kb region of CEA genomic sequence. The 11,288 bp HindIII-Sau3A fragment that was sequenced is represented by the heavy line under lambda-CEA1. The 3774 bp Hind III-Hind III fragment that was sequenced is represented by the heavy line under lambda-CEA7. The bent arrows represent the transcription start point for CEA mRNA. The straight arrows represent the oligonucleotides CR15 and CR16. H, HindIII; S, SstI; B, BamHI; E, EcoRI; X, XbaI.

Construction of Transcriptional Reaulatory Sequence of Carcinoembryonic Antigen/Cytosine Deaminase Molecular Chimaera A) Cloning and Isolation of the Transcriptional Regulatory Sequence of the Carcinoembryonic Antigen Gene CEA genomic clones were identified and isolated from the human chromosome 19 genomic library LL19NL01, ATCC #57766, by standard techniques (Richards, C. A. et al. Cancer Research 50:1521–1527, 1990 which is herein incorporated by reference in its entirety). The CEA clones were identified by plaque hybridization to $^{32}$p end-labelled oligonucleotides CR15 and CR16. CR15, 5'-CCCTGTGATCTCCAGGACAGCTCAGTCTC-3'(SEQ ID NO:7), and CR16, 5'-GTTTCCTGAGTGATGTCTGTGTGCAATG-3'(SEQ ID NO:8), hybridize to a 5' non-transcribed region of CEA that has little homology to other members of the CEA gene family. Phage DNA was isolated from three clones that hybridized to both oligonucleotide probes. Polymerase chain reaction, restriction mapping, and DNA sequence analysis confirmed that the three clones contained CEA genomic sequences. The three clones are designated lambdaCEA1, lambdaCEA5, and lambdaCEA7 and have inserts of approximately 13.5, 16.2, and 16.7 kb respectively. A partial restriction map of the three overlapping clones is shown in FIG. 10.

Figure 11:
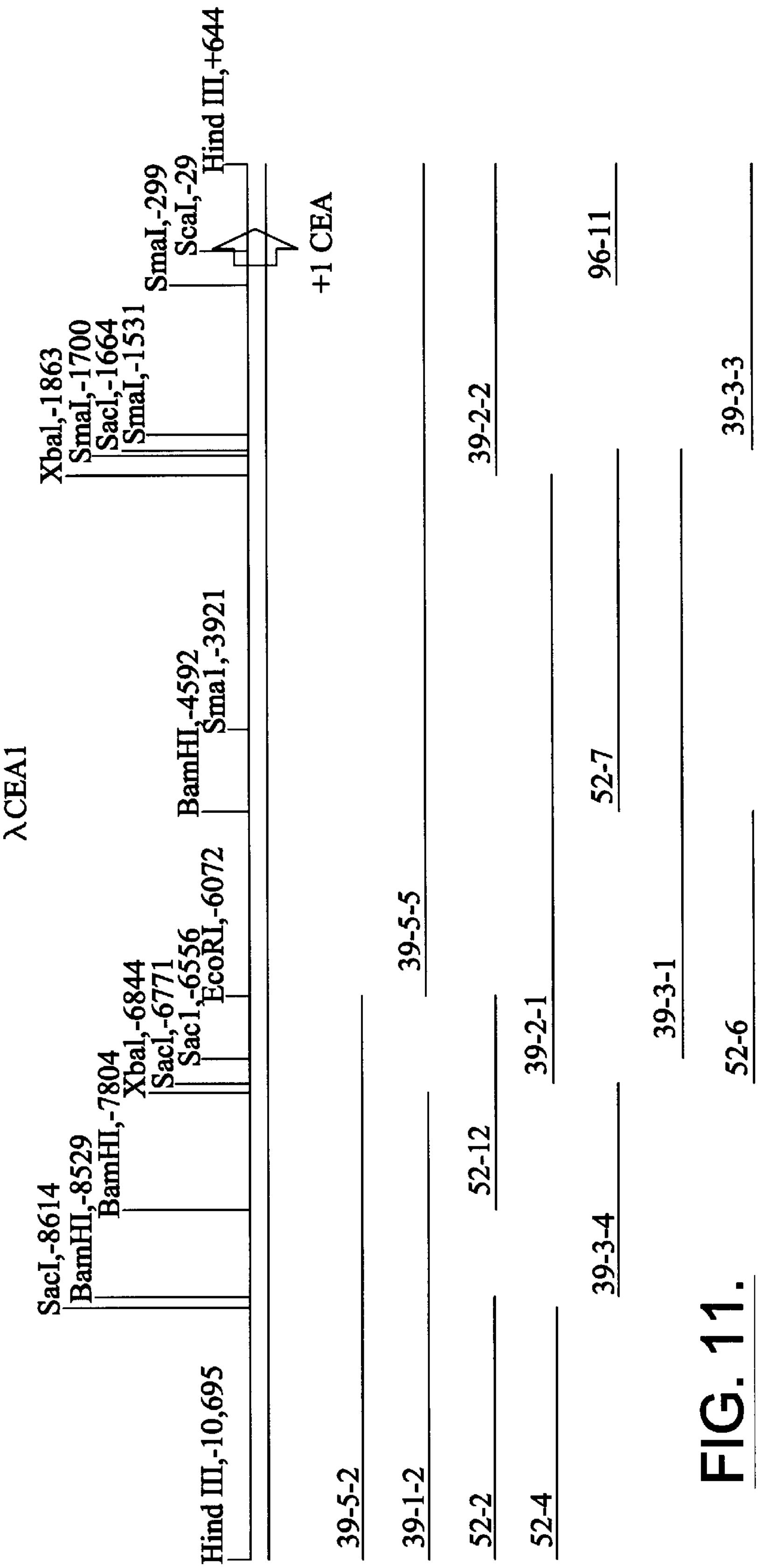
FIG. 11: Restriction map of part of lambda CEA1. The arrow head represents the approximate location of the transcription initation point for CEA mRNA. Lines below the map represent the CEA inserts of pBS+ subclones. These subclones are convenient sources for numerous CEA restriction fragments.

Clone lambdaCEA1 was initally chosen for extensive analysis. Fragments isolated from lambdaCEA1 were subcloned using standard techniques into the plasmid pBS+ (Stratagene Cloning Systems, La Jolla, Calif.) to facilitate sequencing, site-directed mutagenesis, and construction of chimeric genes. The inserts of some clones are represented in FIG. 11. The complete DNA sequence of a 11,288 bp Hind III/Sau3A restriction fragment from lambdaCEA1 (FIG.

12A, SEQ ID NO:4) was determined by the dideoxy sequencing method using the dsDNA Cycle Sequencing System from Life Technologies, Inc. and multiple oligonucleotide primers. This sequence extends from −10.7 kb to +0.6 kb relative to the start site of CEA mRNA. The sequence of 3774 base pair Hind III restriction fragment from lambdaCEA1 was also determined (FIG. 12B SEQ ID NO:5). This sequence extends from −14.5 kb to −10.7 kb relative to the start site of CEA mRNA. This Hind III fragment is present in plasmid pCR145.

To determine important transcriptional regulatory sequences various fragments of CEA genomic DNA are linked to a reporter gene such as luciferase or chloramphenicol acetyltransferase. Various fragments of CEA genomic DNA are tested to determine the optimized, cell-type specific TRS that results in high level reporter gene expression in CEA-positive cells but not in CEA-negative cells. The various reporter constructs, along with appropriate controls, are transfected into tissue culture cell lines that express high, low, or no CEA. The reporter gene analysis identifies both positive and negative transcriptional regulatory sequences. The optimized CEA-specific TRS is identified through the reporter gene analysis and is used to specifically direct the expression of any desired linked coding sequence, such as cytosine deaminase or VZV TK, in cancerous cells that express CEA. The optimized CEA-specfic TRS, as used herein, refers to any DNA construct that directs suitably high levels of expression in CEA positive cells and low or no expression in CEA-negative cells. The optimized CEA-specific TRS consists of one or several different fragments of CEA genomic sequence or multimers of selected sequences that are linked together by standard recombinant DNA techniques. It will be appreciated by those skilled in the art that the optimized CEA-specific TRS may also include some sequences that are not derived from the CEA genomic sequences shown in FIGS. 12A or 12B. These other sequences may include sequences from adjoining regions of the CEA locus, such as sequences from the introns, or sequences further upstream or downstream from the sequenced DNA shown in FIGS. 12A or 12B, or they could include transcriptional control elements from other genes that when linked to selected CEA sequences result in the desired CEA-specific regulation.

The CEA sequence of FIGS. 12A and 12B were computer analyzed for characterized consensus sequences which have been associated with gene regulation. Currently not enough is known about transcriptional regulatory sequences to accurately predict by sequence alone whether a sequence will be functional. However, computer searches for characterized consensus sequences can help identify transcriptional regulatory sequences in uncharacterized sequences since many enhancers and promoters consist of unique combinations and spatial alignments of several characterized consensus sequences as well as other sequences. Since not all transcriptional regulatory sequences have been identified and not all sequences that are identical to characterized consensus sequences are functional, such a computer analysis can only suggest possible regions of DNA that may be functionally important for gene regulation.

Figure 12C:
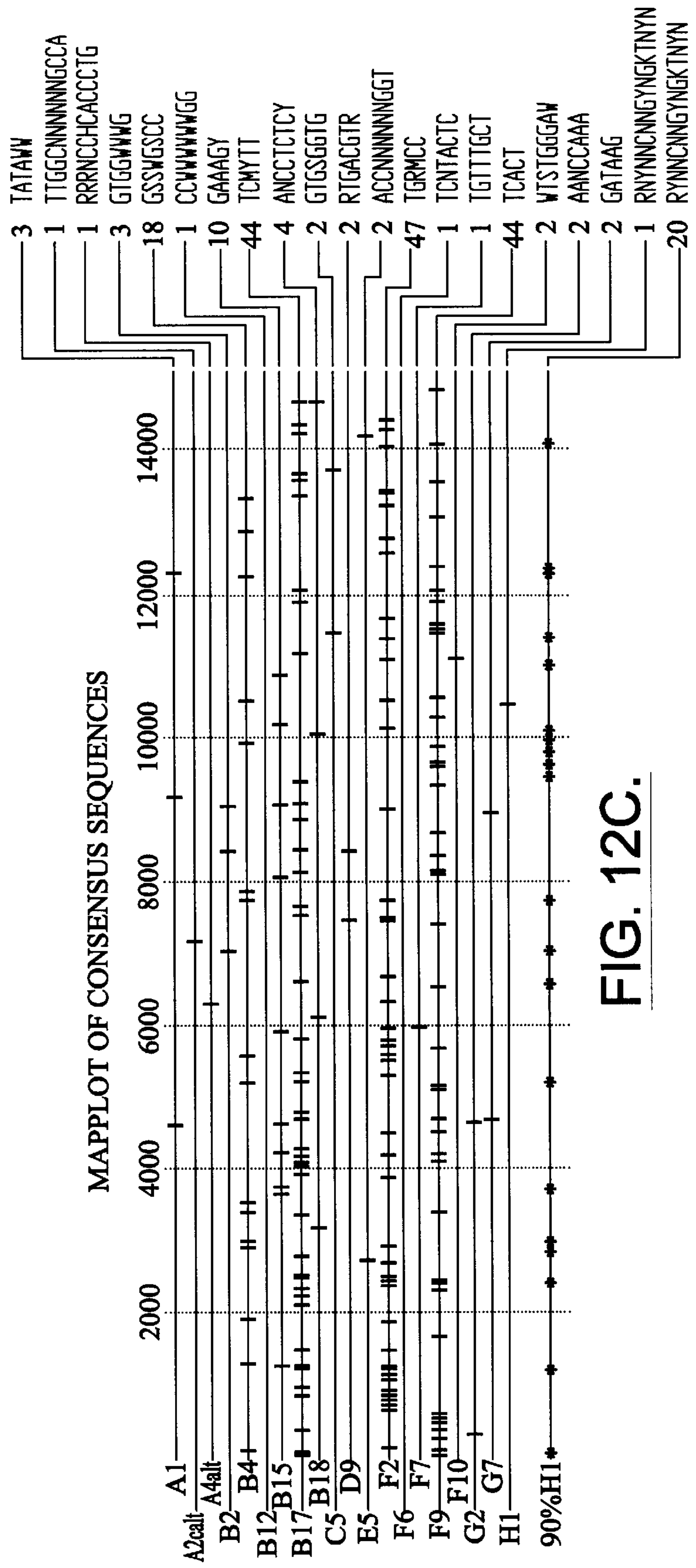
FIG. 12C: Mapplot of 15,056 bp Hind III to Sau 3A fragment from CEA genomic DNA showing consensus sequences. Schematic representation of some of the consensus sequences found in the CEA sequence of FIGS. 12A and 12B. The consensus sequences shown here are from the transcriptional dictionary of Locker and Buzard (DNA Sequence 1, 3–11 (1990)). The lysozymal silencer is coded B18. The last line represents 90% homology to the topoisomerase II cleavage consensus.

Some examples of the consensus sequences that are present in the CEA sequence(FIG. 12A and 12B) are shown in FIG. 12C. Four copies of a lysozymal silencer consensus sequences have been found in the CEA sequence. Inclusion of one or more copies of this consensus sequence in the molecular chimera can help optimize CEA-specific expression. A cluster of topoisomerase II cleavage consensus identified approximately 4–5 kb upstream of the CEA transcriptional start suggest that this region of CEA sequence may contain important transcriptional regulatory signals that may help optimize CEA-specific expression.

The first fragment of CEA genomic sequence analyzed for transcriptional activity extends from −299 to +69, but it is appreciated by those skilled in the art that other fragments are tested in order to isolate a TRS that directs strong expression in CEA-positive cells but little expression in CEA-negative cells. As diagrammed in FIG. 13 the 943 bp SmaI-Hind III fragment of plasmid 39-5-5 was subcloned into the SmaI-HindIII sites of vector pBS+(Statagene Cloning Systems) creating plasmid 96–11. Single-stranded DNA was rescued from cultures of XL1-blue 96-11 using an M13 helper virus by standard techniques. Oligonucleotide CR70, 5'-CCTGGAACTCAAGCTTGAATTCTCCACAGAGGAGG-3'(SEQ ID NO:9), was used as a primer for oligonucleotide-directed mutagenesis to introduce HindIII and EcoRI restriction sites at +65. Clone 109-3 was isolated from the mutagenesis reaction and was verified by restriction and DNA sequence analysis to contain the desired changes in the DNA sequence. CEA genomic sequences −299 to +69, original numbering FIG. 12, were isolated from 109-3 as a 381 bp EcoR I/Hind III fragment. Plasmid pRc/CMV (Invitrogen Corporation, San Diego, Calif.) was restricted with Aat II and Hind III and the 4.5 kb fragment was isolated from low melting point agarose by standard techniques. The 4.5 kb fragment of pRc/CMV was ligated to the 381 bp fragment of 109-3 using T4 DNA ligase. During this ligation the compatible Hind III ends of the two different restriction fragments were ligated. Subsequently the ligation reaction was supplemented with the four deoxynucleotides, dATP, dCTP, dGTP, and dTTP, and T4 DNA polymerase in order to blunt the non-compatible Aat II and EcoR I ends. After incubating, phenol extracting, and ethanol precipitating the reaction, the DNAs were again incubated with T4 DNA ligase. The resulting plasmid, pCR92, allows the insertion of any desired coding sequence into the unique Hind III site downstream of the CEA TRS, upstream from a polyadenylation site and linked to a dominant selectable marker. The coding sequence for cytosine deaminase or other desirable effector or reporter gene, when inserted in the correct orientation into the Hind III site, are transcriptionally regulated by the CEA sequences and are preferably expressed in cells that express CEA but not in cells that do not express CEA.

In order to determine the optimized CEA TRS other reporter gene constructs containing various fragments of CEA genomic sequences are made by standard techniques from DNA isolated from any of the CEA genomic clones (FIGS. 10, 11, 13, and 14). DNA fragments extending from the Hind III site introduced at position +65 (original numbering FIG. 12A) and numerous different upstream sites are isolated and cloned into the unique Hind III site in plasmid pSVOALdelta5' (De Wet, J. R., et al. Molecular and Cellular Biology 7:725–737, 1987 which is herein incorporated by reference in its entirety) or any similar reporter gene plasmid to construct luciferase reporter gene constructs, FIGS. 13 and 14. These and similar constructs are used in transient expression assays performed in several CEA-positive and CEA-negative cell lines to determine a strong, CEA-positive cell-type specific TRS. FIGS. 14B, 14C, and 14D show the results obtained from several CEA/luciferase reporter constructs. The optimized TRS is used to regulate the expression of cytosine deaminase or other desirable gene in a cell-type specific pattern in order to be able to specifically kill cancer cells. The desirable expression cassette is added to a retroviral shuttle vector to aid in delivery of the expression cassette to cancerous tissue.

Strains containing plasmids 39-5-5 and 39-5-2 were deposited at the ATCC under the Budapest Treaty with Accession No. 68904 and 68905, respectively. A strain containing plasmid pCR92 was deposited with the ATCC under the Budapest Treaty with Accession No. 68914. A strain containing plasmid pCR145 was deposited at the ATCC under the Budapest Treaty with Accession No. 69460.

B) Cloning and Isolation of the *E. coli* Gene Encoding Cytosine Deaminase

A positive genetic selection was designed for the cloning of the codA gene from *E. coli*. The selection took advantage of the fact that *E. coli* is only able to metabolize cytosine via cytosine deaminase. Based on this, an *E. coli* strain was constructed that could only utilize cytosine as a pyrimidine source when cytosine deaminase was provided in trans. This strain, BA101, contains a deletion of the codAB operon and a mutation in the pyrF gene. The strain was created by transducing a pyrF mutation (obtained from the *E. coli* strain X82 (*E. coli* Genetic Stock Center, New Haven, Conn.)) into the strain MBM7007 (W. Dallas, Burroughs Wellcome Co., N.C.) which carried a deletion of the chromosome from lac to argF. The pyrF mutation confers a pyrimidine requirement on the strain, BA101. In addition, the strain is unable to metabolize cytosine due to the codAB deletion. Thus, BA101 is able to grow on minimal medium supplemented with uracil but is unable to utilize cytosine as the sole pyrimidine source. This is illustrated in FIG. 15.

The construction of BA101 provided a means for positive selection of DNA fragments encoding cytosine deaminase. The strain, BA101, was transformed with plasmids carrylng inserts from the *E. coli* chromosome and the transformants were selected for growth on minimal medium supplemented with cytosine. Using this approach, the transformants were screened for the ability to metabolize cytosine indicating the presence of a DNA fragment encoding cytosine deaminase. Several sources of DNA could be used for the cloning of the codA gene: 1) a library of the *E. coli* chromosome could be purchased commercially (for example from Clontech, Palo Alto, Calif. or Stratagene, La Jolla, Calif.) and screened; 2) chromosomal DNA could be isolated from *E. coli,* digested with various restriction enzymes and ligated and plasmid DNA with compatible ends before screening; and/or 3) bacteriophage lambda clones containing mapped *E. coli* chromosomal DNA inserts could be screened.

Bacteriophage lambda clones (Y. Kohara, National Institute of Genetics, Japan)containing DNA inserts spanning the 6–8 minute region of the *E. coli* chromosome were screened for the ability to provide transient complementation of the codA defect. Two clones, 137 and 138 were identified in this manner. Large-scale preparations of DNA from these clones were isolated from 500 ml cultures. Restriction enzymes were used to generate DNA fragments ranging in size from 10–12 kilobases. The enzymes used were EcoRI, EcoRI and BamHI, and EcoRI and HindIII. DNA fragments of the desired size were isolated from preparative agarose gels by electroelution. The isolated fragments were ligated to pBR322 (Gibco BRL, Gaithersburg) with compatible ends. The resulting ligation reactions were used to transform the *E. coli* strain, DH5α (Gibco BRL, Gaithersburg, Md.). This step was used to amplify the recombinant plasmids resulting from the ligation reactions. The plasmid DNA preparations isolated from the ampicillin-resistant DH5α transformants were digested with the appropriate restriction enzymes to verify the presence of insert DNA. The isolated plasmid DNA was used to transform BA101. The transformed cells were selected for resistance to ampicillin and for the ability to metabolize cytosine. Two clones were isolated pEA001 (FIG. 16) and pEA002 (FIG. 17). The plasmid pEA001 contains an approximately 10.8 kb EcoRI-BamHI insert while pEA002 contains an approximately 11.5 kb EcoRI-HindIII insert. The isolated plasmids were used to transform BA101 to ensure that the ability to metabolize cytosine was the result of the plasmid and not due to a spontaneous chromosomal mutation.

A physical map of the pEA001 DNA insert was generated using restriction enzymes. Deletion derivatives of pEA001 were constructed based on this restriction map (FIG. 18). The resulting plasmids were screened for the ability to allow BA101 to metabolize cytosine. Using this approach, the codA gene was localized to a 4.8 kb EcoRI-Bg/II fragment (FIG. 19). The presence of codA within these inserts was verified by enzymatic assays for cytosine deaminase activity (FIG. 18). In addition, cell extracts prepared for enzymatic assay were also examined by polyacrylamide gel electrophoresis. Cell extracts that were positive for enzymatic activity also had a protein band migrating with an apparent molecular weight of 52,000 (FIG. 20).

The DNA sequence of both strands was determined for a 1634 basepair fragment(FIG. 21) SEQ ID NO:6. The sequence determination began at the PstI site and extended to PvuII site thus including the codA coding domain(SEQ ID NO:6). An open reading frame of 1283 nucleotides was identified. The thirty amino terminal amino acids were confirmed by protein sequencing. Additional internal amino acid sequences were generated from CNBr-digestion of gel-purified cytosine deaminase SEQ ID NO:15. The amino acids verified by protein sequencing are underlined in FIG. 21.

A 200 basepair PstI fragment was isolated that spanned the translational start codon of codA. This fragment was cloned into $pBS^+$. Single-stranded DNA was isolated from 30 ml culture and mutanized using the custom oligonuclotide BA22 (Sequence: 5'-GACGCATGTGGAAGCTTACAATGTCGAATAACGC-3'(SEQ ID NO:10))purchased from Synthecell Inc., Rockville, Md., and the oligonucleotide-directed mutagenesis kit (Amersham, Arlington Heights, Ill.). The underlined bases in the sequence of the BA22 oligonucleotide represent base changes introduced by the mutagenesis. These changes result in the introduction of an HindIII restriction enzyme site for joining of cytosine deaminase with CEA TRS and in a translational start codon of ATG rather than GTG. The resulting 90 basepair HindIII-PstI fragment is isolated and ligated with the remainder of the cytosine deaminase gene. The chimeric CEA TRS/cytosine deaminase gene is created by ligating the HindIII-PvuII cytosine deaminase-containing DNA fragment with the CEA TRS sequences.

The strain BA101 and the plasmids, pEA001 and pEA003, were deposited with ATCC under the Budapest Treaty with Accession Nos. 55299, 68916, and 68915 respectively.

C) Construction of Transcriptional Regulatory Sequence of Carcinoembryonic Antigen/Cytosine Deaminase Molecular Chimera A 1508 bp HindIII/PvuII fragment containing the coding sequence for cytosine deaminase is isolated from the plasmid containing the full length cytosine deaminase gene of Example 69B that has been altered to contain a Hindill restriction site just 5' of the initation codon. Plasmid pCR92 contains CEA sequences −299 to +69 immediately 5' to a unique HindIII restriction site and a polyadenylation signal 3' to a unique ApaI restriction site (Example 8A, FIG. 13). pCR92 is lineraized with Apa I, the ends are blunted using dNTPs and T4 DNA polymerase, and subsequently digested with HindIII. The pCR92 HindIII/ApaI fragment is ligated to the 1508 bp HindIII/PvuII fragment containing cytosine deaminase. Plasmid pCEA-1/codA, containing cytosine deaminase inserted in the appropriate orientation relative to the CEA TRS and polyadenylation signal is identifed by restriction enzyme and DNA sequence analysis.

The optimized CEA-specific TRS, the coding sequence for cytosine deaminase with an ATG translation start, and a suitable polyadenylation signal are joined together using standard molecular biology techniques. The resulting plasmid, containing cytosine deaminase inserted in the appropriate orientation relative to the optimized CEA specific TRS and a polyadenylation signal is identified by restriction enzyme and DNA sequence analysis.

EXAMPLE 9

Construction of a Retroviral Shuttle Vector Construct Containing the Molecular Chimera of Example 8

The retroviral shuttle vector pL-CEA-1/codA is constructed by ligating a suitable restriction fragment containing the optimized CEA TRS/codA molecular chimera including the polyadenylation signal into an appropriate retroviral shuttle vector, such as N2(XM5) linearized at the Xho I site, using standard molecular biology techniques similar to those detailed in Examples 3 and 4. The retroviral shuttle vector pL-CEA-1/codA is characterized by restriction endonuclease mapping and partial DNA sequencing.

EXAMPLE 10

Virus Production of Retroviral Constructs of Example 9

The retroviral shuttle construct described in Example 9 is placed into an appropriate packaging cell line, such as PA317, by electroporation or infection as described in Example 5. Drug resistant colonies, such as those resistant to G418 when using shuttle vectors containing the NEO gene, are single cell cloned by the limiting dilution method, analyzed by Southern blots, and titred in NIH 3T3 cells to identify the highest producer of full-length virus.

EXAMPLE 11

Demonstration of Neighboring Cell Killing Effect

The following data illustrates and supports this important component of this invention. A human colorectal carcinoma cell line, WiDr, was genetically engineered to express cytosine deaminase (CD) by transfecting into the cell line the cloned gene for cytosine deaminase in an appropriate expression vector system for mammalian cells. WiDr cells expressing cytosine deaminase (WiDR/CD) and control cells not expressing cytosine deaminase (WiDr) were mixed together at different ratios, then plated at a total of 3,000 cells per well in a 96 well microtiter dish. Growth kinetics of these cells over an 8 day period indicated that the different mixtures of cells all grew at approximately equal rates (FIG. 22). This data confirmed that the growth rates of the different mixtures of cells were indistinguishable. Using the same mixtures of WiDr and WiDr/CD cells and again plating 3,000 total cells per well in a 96 well microtiter dish, log dose response curves were generated for the inhibition of cell growth by 5-FC. FIG. 23 indicates that 5-FC was very nontoxic to control WiDr cells ($IC_{50}$ between 10,000 and 30,000 uM) but very toxic to WiDR/CD cells ($IC_{50}$ between 10 uM and 25 uM). Importantly, all the different mixtures of cells showed toxicity patterns similar to the WiDr/CD cells. These data indicate that WiDr/CD cells generated sufficient toxic metabolites of 5-FC to inhibit the cell growth of neighboring cells.

The same mixtures of WiDr and WiDr/CD cells were injected subcutaneously into 10 individual nude mice for 10 individual injections of 10 million cells for each mixture (Table 3). By day 6, all mice had tumors of approximately the same size. On day 6, 5 mice of each group received a daily injection of 5-FC (ip at 500mg/kg body weight) for approximately 20 consecutive days, then injections of 5-FC (ip at 500 mg/kg body weight) three times a week for 19 days. By 22 days post tumor cell injection, all nontreated animals had to be killed due to the large size of the tumors. Likewise, all animals with WiDr derived tumors which also received 5-FC treatment had to be sacrificed on day 22 due to the size of the tumors. This indicates that 5-FC has no effect on WiDr tumors that do not express cytosine deaminase. However, in all tumor groups composed of mixtures of cells which contained WiDr/CD cells, there were significant antitumor effects due to 5-FC treatment. In all groups there were between 3 out of 5, to 4 out of 5 tumor cures (as defined as being tumor free by day 130). This indicates that the indicated percentage of WiDr/CD cells in a mixed tumor generated sufficient toxic metabolites of 5-FC to kill all WiDr and WiDr/CD cells in the tumor.

The following example illustrates pharmaceutical formulations(compositions) which are in accordance with the present invention.

EXAMPLE 12

Injectable Formulation

Infective virion $2\times10^6$ Colony Forming Units(CFU)

Physiologic aqueous solution 1 mL

The infective virion as described herein is asceptically admixed with the a physiologic aqueous solution, which may or may not contain stabilizers, in a suitable sterile glass vial and sealed with a sterile closure and overseal.

Injectable Formulation

Packaging cell line $2\times10^6$ Cells

Physiologic aqueous solution 1 mL

Cells of the packaging cell line as described herein are asceptically admixed with the physiologic aqueous solution, which may or may not contain stabilizers, in a suitable sterile glass vial and sealed with a sterile closure and overseal.

TABLE 1

VZV TK activity in HepG2 and HuH7 cells infected with replication-defective, full-length, artificial retroviruses containing ALB/VZV TK chimaera (pCR74) or AFP/VZV TK chimaera (pCR78). VZV TK activity was quantitated as amount of araM phosphorylated per mg cellular protein per 30 minutes.

| | VZV TK Enzymatic Activity pMoles araM phosphate/mg protein/30 mins | |
|---|---|---|
| Virus | HepG2 | HuH7 |
| None | 9 | 13 |
| N2 | 4 | N.D. |
| pCR74 | 4521 | 2831 |
| pCR78 | 198 | 200 |

N.D.- not determined

TABLE 2

Growth inhibition in HepG2 and HuH7 cells infected with replication-defective, full-length, artificial retroviruses containing ALB/VZV TK chimaera (pCR74) or AFP/VZV TK chimaera (pCR78).

| | IC50 for 9-β-D-arabinofuranosyl-6-methoxy-9H-purine | |
|---|---|---|
| Virus | HepG2 | HuH7 |
| None | >2000 uM | 1621 uM |
| N2 | >2000 uM | N.D. |
| pCR74 | 5 uM | 11 uM |
| pCR78 | 175 uM | 76 uM |

N.D.- not determined

TABLE 3

Number of Cures

| | Treatment | |
|---|---|---|
| Cells Injected | None | 5-FC |
| WiDR | 0/5(22)[1] | 0/5(22) |
| WiDr/CD | 0/5(22) | 3/5(130) |
| WiDr:WiDr/CD(2:1) | 0/5(22) | 4/5(130) |
| WiDr:WiDr/CD(1:1) | 0/5(22) | 4/5(130) |
| WiDr:WiDr/CD(1:2) | 0/5(22) | 4/5(130) |

[1]Day (post-injection) of tumor assessment

We claim:

1. A molecular chimaera comprising a carcinoembryonic antigen (CEA) transcriptional regulatory sequence operatively linked to a nucleic acid sequence encoding an *E. coli* cytosine deaminase.

2. A molecular chimaera comprising a carcinoembryonic antigen (CEA) transcriptional regulatory sequence operatively linked to a nucleic acid sequence encoding an *E. coli* cytosine deaminase, and further comprising a polyadenylation signal downstream of the nucleic acid sequence encoding *E. coli* cytosine deaminase.

3. A molecular chimaera comprising a carcinoembryonic antigen (CEA) transcriptional regulatory sequence operatively linked to a nucleic acid sequence encoding an *E. coli* cytosine deaminase, where said nucleic acid sequence encoding *E. coli* cytosine deaminase has been modified to contain an ATG translational start site.

* * * * *

UNITED STATES PATENT AND TRADEMARK OFFICE

CERTIFICATE OF CORRECTION

PATENT NO. : 6,300,490 B1
DATED : October 9, 2001
INVENTOR(S) : Huber et al.

It is certified that error appears in the above-identified patent and that said Letters Patent is hereby corrected as shown below:

Title page,
Item [63], Related U.S. Application Data, "application No: 07/574,994, filed on Sep. 27, 1990, now abandoned." should read -- application No. 07/574,994, filed on Aug. 29, 1990, now abandoned. --

Signed and Sealed this

Eighth Day of October, 2002

*Attest:*

JAMES E. ROGAN

*Attesting Officer*

*Director of the United States Patent and Trademark Office*

SEQUENCE LISTING

```
<160> NUMBER OF SEQ ID NOS:   36

<210> SEQ ID NO 1
<211> LENGTH: 1980
<212> TYPE: DNA
<213> ORGANISM: Varicella zoster

<400> SEQUENCE: 1

cctgtaacag gttcagaccc cgttgagata caaacacaag gaggggggtc accattattt     60

catcagatcc cgtgggtgtg gtttccttta ttaaagccat ggtatccctc agctggcgca    120

taccctcgca aaactggtga tacttagtag gggtatgtat attagcgcta aaacggcaag    180

attttaattc cactataaaa caaacggtct ttccggcacc actggattcc gtttgtataa    240

tacaaacaca atcggggcgt cggcgtccca aatttacttc aaacgacatt gatatgcgta    300

cagccctttg aacatccacg tgggataacg gcgacaggag ttttgccagc ctcgggttga    360

acgcgtccgc gaaacctcga cgtacgttat caatatcctt tttgagtaca tcgtaaaaac    420

gagtgtggca acgttgtccc aaacgaaaac acttggcccg aattcgacta gcggacatat    480

ttgaagttcc gtcccagaag ataacctaag acgcgtttgt ctacaataaa catgtcaacg    540

gataaaaccg atgtaaaaat gggcgttttg cgtatttatt tggacggggc gtatggaatt    600

ggaaaaacga ccgccgccga agaattttta caccactttg caataacacc aaaccggatc    660

ttactcattg gggagcccct gtcgtattgg cgtaaccttg caggggagga cgccatttgc    720

ggaatttacg gaacacaaac tcgccgtctt aatggagacg tttcgcctga agacgcacaa    780

cgcctcacgg ctcattttca gagcctgttc tgttctccgc atgcaattat gcatgcgaaa    840

atctcggcat tgatggacac aagtacatcg gatctcgtac aagtaaataa ggagccgtat    900

aaaattatgt tatccgaccg acacccaatc gcctcaacta tatgttttcc cttgtccaga    960

tacttagtgg gagatatgtc cccagcggcg cttcctgggt tattgtttac gcttcccgct   1020

gaacccccccg ggaccaactt ggtagtttgt accgtttcac tccccagtca tttatccaga   1080

gtaagcaaac gggccagacc gggagaaacg gttaatctgc cgtttgttat ggttctgaga   1140
```

-continued aatgtatata taatgcttat taatacaatt atatttctta aaactaacaa ctggcacgcg 1200
ggctggaaca cactgtcatt ttgtaatgat gtatttaaac agaaattaca aaaatccgag 1260
tgtataaaac tacgcgaagt acctgggatt gaagacacgt tattcgccgt gcttaaactt 1320
ccggagcttt gcggagagtt tggaaatatt ctgccgttat gggcatgggg aatggagacc 1380
ctttcaaact gcttacgaag catgtctccg ttcgtattat cgttagaaca gacaccccag 1440
catgcggcac aagaactaaa aactctgcta ccccagatga ccccggcaaa catgtcctcc 1500
ggtgcatgga atatattgaa agagcttgtt aatgccgttc aggacaacac ttcctaaata 1560
tacctagtat ttacgtatgt accagtaaaa agatgataca cattgtcata ctcgcgtgta 1620
cgtgtttttc tttttttatat atgcgtcatt tattaccaca tcctttaatc ccgcctttat 1680
ctccctaaaa cggagtggta atattaaaag ccgccaagcc tgttggtggg tgaggagggg 1740
taaaggcacg ctgtgtgcat aacgttgcgg tgatattgta gcgcaagtaa cagcgactat 1800
gtttgcgcta gttttagcgg tggtaattct tcctctgtgg accacggcta ataaatctta 1860
cgtaacacca acccctgcga ctcgctctat cggacatatg tctgctcttc tacgagaata 1920
ttccgaccgt aatatgtctc tgaaattaga agccttttat cctactggtt tcgatgaaga 1980

<210> SEQ ID NO 2
<211> LENGTH: 276
<212> TYPE: DNA
<213> ORGANISM: Artificial sequence
<220> FEATURE:
<221> NAME/KEY: misc_feature
<223> OTHER INFORMATION: Description of artificial sequence: chimera of murine ALB and var icella zoster virus thymidine kinase.

<400> SEQUENCE: 2
atggtatgat tttgtaatgg ggtaggaacc aatgaaatgc gaggtaagta tggttaatga 60
tctacagtta ttggttaaag aagtatatta gagcgagtct ttctgcacac agatcacctt 120
tcctatcaac cccgggatcc tacaataaac atgtcaacgg ataaaaccga tgtaaaaatg 180
ggcgttttgc gtatttattt ggacggggcg tatggaattg gaaaaacgac cgccgccgaa 240
gaatttttac accactttgc aataacacca aaccgg 276

<210> SEQ ID NO 3
<211> LENGTH: 228
<212> TYPE: DNA
<213> ORGANISM: Artificial sequence
<220> FEATURE:
<221> NAME/KEY: misc_feature
<223> OTHER INFORMATION: Description of artificial sequence: chimera of human AFP and vari cella zoster virus thymidine kinase

<400> SEQUENCE: 3
gcattgcctg aaaagagtat aaaagaattt cagcatgatt ttccatattg tgcttccacc 60
actgccaata acaccggatc gcaagctgat cctacaataa acatgtcaac ggataaaacc 120
gatgtaaaaa tgggcgtttt gcgtatttat ttggacgggg cgtatggaat tggaaaaacg 180
accgccgccg aagaattttt acaccacttt gcaataacac caaaccgg 228

<210> SEQ ID NO 4
<211> LENGTH: 11288
<212> TYPE: DNA
<213> ORGANISM: Homo sapiens

<400> SEQUENCE: 4
aagcttaaaa cccaatggat tgacaacatc aagagttgga acaagtggac atggagatgt 60

-continued

```
tacttgtgga aatttagatg tgttcagcta tcgggcagga gaatctgtgt caaattccag    120
catggttcag aagaatcaaa aagtgtcaca gtccaaatgt cgaacagtgc aggggataaa    180
actgtggtgc attcaaactg agggatattt tggaacatga gaaaggaagg gattgctgct    240
gcacagaaca tggatgatct cacacataga gttgaaagaa aggagtcaat cgcagaatag    300
aaaatgatca ctaattccac ctctataaag tttccaagag gaaaacccaa ttctgctgct    360
agagatcaga atggaggtga cctgtgcctt gcaatggctg tgagggtcac gggagtgtca    420
cttagtgcag gcaatgtgcc gtatcttaat ctgggcaggg ctttcatgag cacataggaa    480
tgcagacatt actgctgtgt tcattttact tcaccggaaa agaagaataa aatcagccgg    540
gcgcggtggc tcacgcctgt aatcccagca ctttagaagg ctgaggtggg cagattactt    600
gaggtcagga gttcaagacc accctggcca atatggtgaa accccggctc tactaaaaat    660
acaaaaatta gctgggcatg gtggtgcgcg cctgtaatcc cagctactcg ggaggctgag    720
gctggacaat tgcttggacc caggaagcag aggttgcagt gagccaagat tgtgccactg    780
cactccagct tgggcaacag agccagactc tgtaaaaaaa aaaaaaaaaa aaaaaaaaag    840
aaagaaagaa aaagaaaaga aagtataaaa tctctttggg ttaacaaaaa aagatccaca    900
aaacaaacac cagctcttat caaacttaca caactctgcc agagaacagg aaacacaaat    960
actcattaac tcacttttgt ggcaataaaa ccttcatgtc aaaaggagac caggacacaa   1020
tgaggaagta aaactgcagg ccctacttgg gtgcagagag ggaaaatcca caaataaaac   1080
attaccagaa ggagctaaga tttactgcat tgagttcatt ccccaggtat gcaaggtgat   1140
tttaacacct gaaaatcaat cattgccttt actacataga cagattagct agaaaaaaat   1200
tacaactagc agaacagaag caatttggcc ttcctaaaat tccacatcat atcatcatga   1260
tggagacagt gcagacgcca atgacaataa aaagagggac ctccgtcacc cggtaaacat   1320
gtccacacag ctccagcaag cacccgtctt cccagtgaat cactgtaacc tcccctttaa   1380
tcagccccag gcaaggctgc ctgcgatggc cacacaggct ccaacccgtg ggcctcaacc   1440
tcccgcagag gctctccttt ggccacccca tggggagagc atgaggacag ggcagagccc   1500
tctgatgccc acacatggca ggagctgacg ccagagccat gggggctgga gagcagagct   1560
gctggggtca gagcttcctg aggacaccca ggcctaaggg aaggcagctc cctggatggg   1620
ggcaaccagg ctccgggctc caacctcaga gcccgcatgg gaggagccag cactctaggc   1680
ctttcctagg gtgactctga ggggaccctg acacgacagg atcgctgaat gcacccgaga   1740
tgaaggggcc accacgggac cctgctctcg tggcagatca ggagagagtg ggacaccatg   1800
ccaggccccc atggcatggc tgcgactgac ccaggccact cccctgcatg catcagcctc   1860
ggtaagtcac atgaccaagc ccaggaccaa tgtggaagga aggaaacagc atcccctttta   1920
gtgatggaac ccaaggtcag tgcaaagaga ggccatgagc agttaggaag ggtggtccaa   1980
cctacagcac aaaccatcat ctatcataag tagaagccct gctccatgac ccctgcattt   2040
aaataaacgt ttgttaaatg agtcaaattc cctcaccatg agagctcacc tgtgtgtagg   2100
cccatcacac acacaaacac acacacacac acacacacac acacacacac acacagggaa   2160
agtgcaggat cctggacagc accaggcagg cttcacaggc agagcaaaca gcgtgaatga   2220
cccatgcagt gccctgggcc ccatcagctc agagaccctg tgagggctga gatggggcta   2280
ggcaggggag agacttagag agggtggggc ctccagggag ggggctgcag ggagctgggt   2340
actgccctcc agggaggggg ctgcagggag ctgggtactg ccctccaggg agggggctgc   2400
```

-continued

```
agggagctgg gtactgccct ccagggaggg ggctgcaggg agctgggtac tgccctccag   2460
ggagggggct gcagggagct gggtactgcc ctccagggag gcaggagcac tgttcccaac   2520
agagagcaca tcttcctgca gcagctgcac agacacagga gcccccatga ctgccctggg   2580
ccagggtgtg gattccaaat ttcgtgcccc attgggtggg acggaggttg accgtgacat   2640
ccaaggggca tctgtgattc caaacttaaa ctactgtgcc tacaaaatag gaaataaccc   2700
tactttttct actatctcaa attccctaag cacaagctag caccctttaa atcaggaagt   2760
tcagtcactc ctggggtcct cccatgcccc cagtctgact tgcaggtgca cagggtggct   2820
gacatctgtc cttgctcctc ctcttggctc aactgccgcc cctcctgggg gtgactgatg   2880
gtcaggacaa gggatcctag agctggcccc atgattgaca ggaaggcagg acttggcctc   2940
cattctgaag actaggggtg tcaagagagc tgggcatccc acagagctgc acaagatgac   3000
gcggacagag ggtgacacag ggctcagggc ttcagacggg tcgggaggct cagctgagag   3060
ttcagggaca gacctgagga gcctcagtgg gaaaagaagc actgaagtgg gaagttctgg   3120
aatgttctgg acaagcctga gtgctctaag gaaatgctcc caccccgatg tagcctgcag   3180
cactggacgg tctgtgtacc tccccgctgc ccatcctctc acagccccg cctctaggga   3240
cacaactcct gccctaacat gcatctttcc tgtctcattc cacacaaaag ggcctctggg   3300
gtccctgttc tgcattgcaa ggagtggagg tcacgttccc acagaccacc cagcaacagg   3360
gtcctatgga ggtgcggtca ggaggatcac acgtcccccc atgcccaggg gactgactct   3420
gggggtgatg gattggcctg gaggccactg gtcccctctg tccctgaggg gaatctgcac   3480
cctggaggct gccacatccc tcctgattct ttcagctgag ggcccttctt gaaatcccag   3540
ggaggactca acccccactg ggaaaggccc agtgtggacg gttccacagc agcccagcta   3600
aggcccttgg acacagatcc tgagtgagag aacctttagg gacacaggtg cacggccatg   3660
tccccagtgc ccacacagag caggggcatc tggaccctga gtgtgtagct cccgcgactg   3720
aacccagccc ttccccaatg acgtgacccc tggggtggct ccaggtctcc agtccatgcc   3780
accaaaatct ccagattgag ggtcctccct tgagtccctg atgcctgtcc aggagctgcc   3840
ccctgagcaa atctagagtg cagagggctg ggattgtggc agtaaaagca gccacatttg   3900
tctcaggaag gaaagggagg acatgagctc caggaagggc gatggcgtcc tctagtgggc   3960
gcctcctgtt aatgagcaaa aaggggccag gagagttgag agatcagggc tggccttgga   4020
ctaaggctca gatggagagg actgaggtgc aaagaggggg ctgaagtagg ggagtggtcg   4080
ggagagatgg gaggagcagg taaggggaag ccccagggag gccgggggag ggtacagcag   4140
agctctccac tcctcagcat tgacatttgg ggtggtcgtg ctagtggggt tctgtaagtt   4200
gtagggtgtt cagcaccatc tggggactct acccactaaa tgccagcagg actccctccc   4260
caagctctaa caaccaacaa tgtctccaga ctttccaaat gtcccctgga gagcaaaatt   4320
gcttctggca gaatcactga tctacgtcag tctctaaaag tgactcatca gcgaaatcct   4380
tcacctcttg ggagaagaat cacaagtgtg agaggggtag aaactgcaga cttcaaaatc   4440
tttccaaaag agttttactt aatcagcagt ttgatgtccc aggagaagat acatttagag   4500
tgtttagagt tgatgccaca tggctgcctg tacctcacag caggagcaga gtgggttttc   4560
caagggcctg taaccacaac tggaatgaca ctcactgggt tacattacaa agtggaatgt   4620
ggggaattct gtagactttg ggaagggaaa tgtatgacgt gagcccacag cctaaggcag   4680
tggacagtcc actttgaggc tctcaccatc taggagacat ctcagccatg aacatagcca   4740
catctgtcat tagaaaacat gttttattaa gaggaaaaat ctaggctaga agtgctttat   4800
```

-continued

```
gctctttttt ctctttatgt tcaaattcat atacttttag atcattcctt aaagaagaat   4860
ctatccccct aagtaaatgt tatcactgac tggatagtgt tggtgtctca ctcccaaccc   4920
ctgtgtggtg acagtgccct gcttccccag ccctgggccc tctctgattc ctgagagctt   4980
tgggtgctcc ttcattagga ggaagagagg aagggtgttt ttaatattct caccattcac   5040
ccatccacct cttagacact gggaagaatc agttgcccac tcttggattt gatcctcgaa   5100
ttaatgacct ctatttctgt cccttgtcca tttcaacaat gtgacaggcc taagaggtgc   5160
cttctccatg tgatttttga ggagaaggtt ctcaagataa gttttctcac acctctttga   5220
attacctcca cctgtgtccc catcaccatt accagcagca tttggaccct ttttctgtta   5280
gtcagatgct ttccacctct tgagggtgta tactgtatgc tctctacaca ggaatatgca   5340
gaggaaatag aaaaagggaa atcgcattac tattcagaga gaagaagacc tttatgtgaa   5400
tgaatgagag tctaaaatcc taagagagcc catataaaat tattaccagt gctaaaacta   5460
caaaagttac actaacagta aactagaata ataaaacatg catcacagtt gctggtaaag   5520
ctaaatcaga tattttttttc ttagaaaaag cattccatgt gtgttgcagt gatgacagga   5580
gtgcccttca gtcaatatgc tgcctgtaat ttttgttccc tggcagaatg tattgtcttt   5640
tctcccttta aatcttaaat gcaaaactaa aggcagctcc tgggccccct ccccaaagtc   5700
agctgcctgc aaccagcccc acgaagagca gaggcctgag cttccctggt caaaataggg   5760
ggctagggag cttaaccttg ctcgataaag ctgtgttccc agaatgtcgc tcctgttccc   5820
aggggcacca gcctggaggg tggtgagcct cactggtggc ctgatgctta ccttgtgccc   5880
tcacaccagt ggtcactgga accttgaaca cttggctgtc gcccggatct gcagatgtca   5940
agaacttctg gaagtcaaat tactgcccac ttctccaggg cagatacctg tgaacatcca   6000
aaaccatgcc acagaaccct gcctggggtc tacaacacat atggactgtg agcaccaagt   6060
ccagccctga atctgtgacc acctgccaag atgcccctaa ctgggatcca ccaatcactg   6120
cacatggcag gcagcgaggc ttggaggtgc ttcgccacaa ggcagcccca atttgctggg   6180
agtttcttgg cacctggtag tggtgaggag ccttgggacc ctcaggatta ctccccttaa   6240
gcatagtggg gacccttctg catccccagc aggtgccccg ctcttcagag cctctctctc   6300
tgaggtttac ccagacccct gcaccaatga gaccatgctg aagcctcaga gagagagatg   6360
gagctttgac caggagccgc tcttccttga gggccagggc agggaaagca ggaggcagca   6420
ccaggagtgg gaacaccagt gtctaagccc ctgatgagaa cagggtggtc tctcccatat   6480
gcccatacca ggcctgtgaa cagaatcctc cttctgcagt gacaatgtct gagaggacga   6540
catgtttccc agcctaacgt gcagccatgc ccatctaccc actgcctact gcaggacagc   6600
accaacccag gagctgggaa gctgggagaa gacatggaat acccatggct tctcaccttc   6660
ctccagtcca gtgggcacca tttatgccta ggacacccac ctgccggccc caggctctta   6720
agagttaggt cacctaggtg cctctgggag gccgaggcag gagaattgct tgaacccggg   6780
aggcagaggt tgcagtgagc cgagatcaca ccactgcact ccagcctggg tgacagaatg   6840
agactctgtc tcaaaaaaaa agagaaagat agcatcagtg gctaccaagg gctaggggca   6900
ggggaaggtg gagagttaat gattaatagt atgaagtttc tatgtgagat gatgaaaatg   6960
ttctggaaaa aaaaatatag tggtgaggat gtagaatatt gtgaatataa ttaacggcat   7020
ttaattgtac acttaacatg attaatgtgg catattttat cttatgtatt tgactacatc   7080
caagaaacac tgggagaggg aaagcccacc atgtaaaata cacccaccct aatcagatag   7140
```

-continued

```
tcctcattgt acccaggtac aggcccctca tgacctgcac aggaataact aaggatttaa   7200
ggacatgagg cttcccagcc aactgcaggt gcacaacata aatgtatctg caaacagact   7260
gagagtaaag ctgggggcac aaacctcagc actgccagga cacacaccct tctcgtggat   7320
tctgacttta tctgacccgg cccactgtcc agatcttgtt gtgggattgg gacaagggag   7380
gtcataaagc ctgtccccag ggcactctgt gtgagcacac gagacctccc cacccccca   7440
ccgttaggtc tccacacata gatctgacca ttaggcattg tgaggaggac tctagcgcgg   7500
gctcagggat cacaccagag aatcaggtac agagaggaag acggggctcg aggagctgat   7560
ggatgacaca gagcagggtt cctgcagtcc acaggtccag ctcaccctgg tgtaggtgcc   7620
ccatcccct gatccaggca tccctgacac agctccctcc cggagcctcc tcccaggtga   7680
cacatcaggg tccctcactc aagctgtcca gagagggcag caccttggac agcgcccacc   7740
ccacttcact cttcctccct cacagggctc agggctcagg gctcaagtct cagaacaaat   7800
ggcagaggcc agtgagccca gagatggtga cagggcaatg atccaggggc agctgcctga   7860
aacgggagca ggtgaagcca cagatgggag aagatggttc aggaagaaaa atccaggaat   7920
gggcaggaga ggagaggagg acacaggctc tgtggggctg cagcccagga tgggactaag   7980
tgtgaagaca tctcagcagg tgaggccagg tcccatgaac agagaagcag ctcccacctc   8040
ccctgatgca cggacacaca gagtgtgtgg tgctgtgccc ccagagtcgg gctctcctgt   8100
tctggtcccc agggagtgag aagtgaggtt gacttgtccc tgctcctctc tgctacccca   8160
acattcacct tctcctcatg cccctctctc tcaaatatga tttggatcta tgtccccgcc   8220
caaatctcat gtcaaattgt aaaccccaat gttggaggtg gggccttgtg agaagtgatt   8280
ggataatgcg ggtggatttt ctgctttgat gctgtttctg tgatagagat ctcacatgat   8340
ctggttgttt aaaagtgtgt agcacctctc ccctctctct ctctctctct tactcatgct   8400
ctgccatgta agacgttcct gtttcccctt caccgtccag aatgattgta agttttctga   8460
ggcctcccca ggagcagaag ccactatgct tcctgtacaa ctgcagaatg atgagcgaat   8520
taaacctctt ttctttataa attacccagt ctcaggtatt tctttatagc aatgcgagga   8580
cagactaata caatcttcta ctcccagatc cccgcacacg cttagcccca gacatcactg   8640
cccctgggag catgcacagc gcagcctcct gccgacaaaa gcaaagtcac aaaaggtgac   8700
aaaaatctgc atttggggac atctgattgt gaaagaggga ggacagtaca cttgtagcca   8760
cagagactgg ggctcaccga gctgaaacct ggtagcactt tggcataaca tgtgcatgac   8820
ccgtgttcaa tgtctagaga tcagtgttga gtaaaacagc ctggtctggg gccgctgctg   8880
tccccacttc cctcctgtcc accagagggc ggcagagttc ctcccaccct ggagcctccc   8940
caggggctgc tgacctccct cagccgggcc cacagcccag cagggtccac cctcacccgg   9000
gtcacctcgg cccacgtcct cctcgccctc cgagctcctc acacggactc tgtcagctcc   9060
tccctgcagc ctatcggccg cccacctgag gcttgtcggc cgcccacttg aggcctgtcg   9120
gctgccctct gcaggcagct cctgtcccct acacccctc cttccccggg ctcagctgaa   9180
agggcgtctc ccagggcagc tccctgtgat ctccaggaca gctcagtctc tcacaggctc   9240
cgacgccccc tatgctgtca cctcacagcc ctgtcattac cattaactcc tcagtcccat   9300
gaagttcact gagcgcctgt ctcccggtta caggaaaact ctgtgacagg gaccacgtct   9360
gtcctgctct ctgtggaatc ccagggccca gcccagtgcc tgacacggaa cagatgctcc   9420
ataaatactg gttaaatgtg tgggagatct ctaaaaagaa gcatatcacc tccgtgtggc   9480
ccccagcagt cagagtctgt tccatgtgga cacaggggca ctggcaccag catgggagga   9540
```

-continued

```
ggccagcaag tgcccgcggc tgccccagga atgaggcctc aacccccaga gcttcagaag   9600
ggaggacaga ggcctgcagg gaatagatcc tccggcctga ccctgcagcc taatccagag   9660
ttcagggtca gctcacacca cgtcgaccct ggtcagcatc cctagggcag ttccagacaa   9720
ggccggaggt ctcctcttgc cctccagggg gtgacattgc acacagacat cactcaggaa   9780
acggattccc ctggacagga acctggcttt gctaaggaag tggaggtgga gcctggtttc   9840
catcccttgc tccaacagac ccttctgatc tctcccacat acctgctctg ttcctttctg   9900
ggtcctatga ggaccctgtt ctgccagggg tccctgtgca actccagact ccctcctggt   9960
accaccatgg ggaaggtggg gtgatcacag gacagtcagc ctcgcagaga cagagaccac  10020
ccaggactgt cagggagaac atggacaggc cctgagccgc agctcagcca acagacacgg  10080
agagggaggg tccccctgga gccttcccca aggacagcag agcccagagt cacccacctc  10140
cctccaccac agtcctctct ttccaggaca cacaagacac ctccccctcc acatgcagga  10200
tctggggact cctgagacct ctgggcctgg gtctccatcc ctgggtcagt ggcggggttg  10260
gtggtactgg agacagaggg ctggtccctc cccagccacc acccagtgag cctttttcta  10320
gcccccagag ccacctctgt caccttcctg ttgggcatca tcccaccttc ccagagccct  10380
ggagagcatg gggagacccg ggaccctgct gggtttctct gtcacaaagg aaaataatcc  10440
ccctggtgtg acagacccaa ggacagaaca cagcagaggt cagcactggg gaagacaggt  10500
tgtcctccca ggggatgggg gtccatccac cttgccgaaa agatttgtct gaggaactga  10560
aaatagaagg gaaaaaagag gagggacaaa agaggcagaa atgagagggg aggggacaga  10620
ggacacctga ataaagacca cacccatgac ccacgtgatg ctgagaagta ctcctgccct  10680
aggaagagac tcagggcaga gggaggaagg acagcagacc agacagtcac agcagccttg  10740
acaaaacgtt cctggaactc aagctcttct ccacagagga ggacagagca gacagcagag  10800
accatggagt ctccctcggc ccctccccac agatggtgca tcccctggca gaggctcctg  10860
ctcacaggtg aagggaggac aacctgggag agggtgggag gagggagctg gggtctcctg  10920
ggtaggacag ggctgtgaga cggacagagg gctcctgttg gagcctgaat agggaagagg  10980
acatcagaga gggacaggag tcacaccaga aaaatcaaat tgaactggaa ttggaaaggg  11040
gcaggaaaac ctcaagagtt ctattttcct agttaattgt cactggccac tacgttttta  11100
aaaatcataa taactgcatc agatgacact ttaaataaaa acataaccag ggcatgaaac  11160
actgtcctca tccgcctacc gcggacattg gaaaataagc cccaggctgt ggagggccct  11220
gggaaccctc atgaactcat ccacaggaat ctgcagcctg tcccaggcac tggggtgcaa  11280
ccaagatc                                                           11288
```

<210> SEQ ID NO 5
<211> LENGTH: 3774
<212> TYPE: DNA
<213> ORGANISM: Homo sapiens

<400> SEQUENCE: 5

```
aagcttttta gtgctttaga cagtgagctg gtctgtctaa cccaagtgac ctgggctcca     60
tactcagccc cagaagtgaa gggtgaagct gggtggagcc aaaccaggca agcctaccct    120
cagggctccc agtggcctga gaaccattgg acccaggacc cattacttct agggtaagga    180
aggtacaaac accagatcca accatggtct ggggggacag ctgtcaaatg cctaaaaata    240
tacctgggag aggagcaggc aaactatcac tgccccaggt tctctgaaca gaaacagagg    300
```

-continued

```
ggcaacccaa agtccaaatc caggtgagca ggtgcaccaa atgcccagag atatgacgag    360
gcaagaagtg aaggaaccac ccctgcatca aatgttttgc atgggaagga gaagggggtt    420
gctcatgttc ccaatccagg agaatgcatt tgggatctgc cttcttctca ctccttggtt    480
agcaagacta agcaaccagg actctggatt tggggaaaga cgtttatttg tggaggccag    540
tgatgacaat cccacgaggg cctaggtgaa gagggcagga aggctcgaga cactggggac    600
tgagtgaaaa ccacacccat gatctgcacc acccatggat gctccttcat tgctcacctt    660
tctgttgata tcagatggcc ccattttctg taccttcaca gaaggacaca ggctagggtc    720
tgtgcatggc cttcatcccc ggggccatgt gaggacagca ggtgggaaag atcatgggtc    780
ctcctgggtc ctgcagggcc agaacattca tcacccatac tgacctccta gatgggaatg    840
gcttccctgg ggctgggcca acggggcctg ggcaggggag aaaggacgtc aggggacagg    900
gaggaagggt catcgagacc cagcctggaa ggttcttgtc tctgaccatc caggatttac    960
ttccctgcat ctacctttgg tcattttccc tcagcaatga ccagctctgc ttcctgatct   1020
cagcctccca ccctggacac agcaccccag tccctggccc ggctgcatcc acccaatacc   1080
ctgataaccc aggacccatt acttctaggg taaggagggt ccaggagaca gaagctgagg   1140
aaaggtctga agaagtcaca tctgtcctgg ccagagggga aaaaccatca gatgctgaac   1200
caggagaatg ttgacccagg aaagggaccg aggacccaag aaaggagtca gaccaccagg   1260
gtttgcctga gaggaaggat caaggccccg agggaaagca gggctggctg catgtgcagg   1320
acactggtgg ggcatatgtg tcttagattc tccctgaatt cagtgtccct gccatggcca   1380
gactctctac tcaggcctgg acatgctgaa ataggacaat ggccttgtcc tctctcccca   1440
ccatttggca agagacataa aggacattcc aggacatgcc ttcctgggag gtccaggttc   1500
tctgtctcac acctcaggga ctgtagttac tgcatcagcc atggtaggtg ctgatctcac   1560
ccagcctgtc caggcccttc cactctccac tttgtgacca tgtccaggac cacccctcag   1620
atcctgagcc tgcaaatacc cccttgctgg gtgggtggat tcagtaaaca gtgagctcct   1680
atccagcccc cagagccacc tctgtcacct tcctgctggg catcatccca ccttcacaag   1740
cactaaagag catggggaga cctggctagc tgggtttctg catcacaaag aaaataatcc   1800
cccaggttcg gattcccagg gctctgtatg tggagctgac agacctgagg ccaggagata   1860
gcagaggtca gccctaggga gggtgggtca tccacccagg ggacaggggt gcaccagcct   1920
tgctactgaa agggcctccc caggacagcg ccatcagccc tgcctgagag ctttgctaaa   1980
cagcagtcag aggaggccat ggcagtggct gagctcctgc tccaggcccc aacagaccag   2040
accaacagca caatgcagtc cttccccaac gtcacaggtc accaaaggga aactgaggtg   2100
ctacctaacc ttagagccat caggggagat aacagcccaa tttcccaaac aggccagttt   2160
caatcccatg acaatgacct ctctgctctc attcttccca aaataggacg ctgattctcc   2220
cccaccatgg atttctccct tgtcccggga gccttttctg ccccctatga tctgggcact   2280
cctgacacac acctcctctc tggtgacata tcagggtccc tcactgtcaa gcagtccaga   2340
aaggacagaa ccttggacag cgcccatctc agcttcaccc ttcctccttc acagggttca   2400
gggcaaagaa taaatggcag aggccagtga gcccagagat ggtgacaggc agtgacccag   2460
gggcagatgc ctggagcagg agctggcggg gccacaggga gaaggtgatg caggaaggga   2520
aacccagaaa tgggcaggaa aggaggacac aggctctgtg gggctgcagc ccagggttgg   2580
actatgagtg tgaagccatc tcagcaagta aggccaggtc ccatgaacaa gagtgggagc   2640
acgtggcttc ctgctctgta tatggggtgg gggattccat gccccataga accagatggc   2700
```

-continued

```
cggggttcag atggagaagg agcaggacag gggatcccca ggataggagg accccagtgt   2760

ccccacccag gcaggtgact gatgaatggg catgcagggt cctcctgggc tgggctctcc   2820

ctttgtccct caggattcct tgaaggaaca tccggaagcc gaccacatct acctggtggg   2880

ttctggggag tccatgtaaa gccaggagct tgtgttgcta ggaggggtca tggcatgtgc   2940

tgggggcacc aaagagagaa acctgagggc aggcaggacc tggtctgagg aggcatggga   3000

gcccagatgg ggagatggat gtcaggaaag gctgccccat cagggagggt gatagcaatg   3060

gggggtctgt gggagtgggc acgtgggatt ccctgggctc tgccaagttc cctcccatag   3120

tcacaacctg gggacactgc ccatgaaggg gcgcctttgc ccagccagat gctgctggtt   3180

ctgcccatcc actaccctct ctgctccagc cactctgggt ctttctccag atgccctgga   3240

cagccctggc ctgggcctgt cccctgagag gtgttgggag aagctgagtc tctggggaca   3300

ctctcatcag agtctgaaag gcacatcagg aaacatccct ggtctccagg actaggcaat   3360

gaggaaaggg ccccagctcc tccctttgcc actgagaggg tcgaccctgg gtggccacag   3420

tgacttctgc gtctgtccca tgcaccctga aaccacaaca aaaccccagc cccagaccct   3480

gcaggtacaa tacatgtggg gacagtctgt acccagggga agccagttct ctcttcctag   3540

gagaccgggc ctcagggctg tgcccggggc aggcgggggc agcacgtgcc tgtccttgag   3600

aactcgggac cttaagggtc tctgctctgt gaggcacagc aaggatcctt ctgtccagag   3660

atgaaagcag ctcctgcccc tcctctgacc tcttcctcct tcccaaatct caaccaacaa   3720

ataggtgttt caaatctcat catcaaatct tcatccatcc acatgagaaa gctt         3774
```

<210> SEQ ID NO 6
<211> LENGTH: 1634
<212> TYPE: DNA
<213> ORGANISM: Escherichia coli

<400> SEQUENCE: 6

```
ctgcaggcca ctggttaccg ggaattgttc cggtcaacgc ggtattaggt ggcgcgctga     60

gctatctgat ccttaacccg attttgaatc gtaaaacgac agcagcaatg acgcatgtgg    120

aggctaacag tgtcgaataa cgctttacaa acaattatta acgcccggtt accaggcgaa    180

gaggggctgt ggcagattca tctgcaggac ggaaaaatca gcgccattga tgcgcaatcc    240

ggcgtgatgc ccataactga aaacagcctg gatgccgaac aaggtttagt tataccgccg    300

tttgtggagc cacatattca cctggacacc acgcaaaccg ccggacaacc gaactggaat    360

cagtccggca cgctgtttga aggcattgaa cgctgggccg agcgcaaagc gttattaacc    420

catgacgatg tgaaacaacg cgcatggcaa acgctgaaat ggcagattgc caacggcatt    480

cagcatgtgc gtacccatgt cgatgtttcg gatgcaacgc taactgcgct gaaagcaatg    540

ctggaagtga agcaggaagt cgcgccgtgg attgatctgc aaatcgtcgc cttccctcag    600

gaagggattt tgtcgtatcc caacggtgaa gcgttgctgg aagaggcgtt acgcttaggg    660

gcagatgtag tgggggcgat tccgcatttt gaatttaccc gtgaatacgg cgtggagtcg    720

ctgcataaaa ccttcgccct ggcgcaaaaa tacgaccgtc tcatcgacgt tcactgtgat    780

gagatcgatg acgagcagtc gcgctttgtc gaaaccgttg ctgccctggc gcaccatgaa    840

ggcatgggcg cgcgagtcac cgccagccac accacggcaa tgcactccta taacggggcg    900

tatacctcac gcctgttccg cttgctgaaa atgtccggta ttaactttgt cgccaacccg    960

ctggtcaata ttcatctgca aggacgtttc gatacgtatc caaaacgtcg cggcatcacg   1020
```

-continued

```
cgcgttaaag agatgctgga gtccggcatt aacgtctgct ttggtcacga tgatgtcttc   1080

gatccgtggt atccgctggg aacggcgaat atgctgcaag tgctgcatat ggggctgcat   1140

gtttgccagt tgatgggcta cgggcagatt aacgatggcc tgaatttaat cacccaccac   1200

agcgcaagga cgttgaattt gcaggattac ggcattgccg ccggaaacag cgccaacctg   1260

attatcctgc cggctgaaaa tgggtttgat gcgctgcgcc gtcaggttcc ggtacgttat   1320

tcggtacgtg gcggcaaggt gattgccagc acacaaccgg cacaaaccac cgtatatctg   1380

gagcagccag aagccatcga ttacaaacgt tgaacgactg ggttacagcg agcttagttt   1440

atgccggatg cggcgtgaac gccttatccg gcctacgtag agcactgaac tcgtaggcct   1500

gataagcgta gcgcatcagg caattccagc cgctgatctg tgtcagcggc taccgtgatt   1560

cattcccgcc aacaaccgcg cattcctcca acgccatgtg caaaaatgcc ttcgcagcgg   1620

ctgtctgcca gctg                                                     1634


<210> SEQ ID NO 7
<211> LENGTH: 40
<212> TYPE: DNA
<213> ORGANISM: Artificial sequence
<220> FEATURE:
<221> NAME/KEY: misc_feature
<223> OTHER INFORMATION: Description of artificial sequence:
      oligonucleotide to hybridize with human CE

<400> SEQUENCE: 7

ccctgtgatc tccaggacag ctcagtctcc gtccaatctc                           40


<210> SEQ ID NO 8
<211> LENGTH: 28
<212> TYPE: DNA
<213> ORGANISM: Artificial sequence
<220> FEATURE:
<221> NAME/KEY: misc_feature
<223> OTHER INFORMATION: Description of artificial sequence:
      oligonucleotide to hybridize with human CE

<400> SEQUENCE: 8

gtttcctgag tgatgtctgt gtgcaatg                                        28


<210> SEQ ID NO 9
<211> LENGTH: 35
<212> TYPE: DNA
<213> ORGANISM: Artificial sequence
<220> FEATURE:
<221> NAME/KEY: misc_feature
<223> OTHER INFORMATION: Description of artificial sequence:
      oligonucleotide to introduce restriction site

<400> SEQUENCE: 9

cctggaactc aagcttgaat tctccacaga ggagg                                35


<210> SEQ ID NO 10
<211> LENGTH: 34
<212> TYPE: DNA
<213> ORGANISM: Artificial sequence
<220> FEATURE:
<221> NAME/KEY: misc_feature
<223> OTHER INFORMATION: Description of artificial sequence:
      oligonucleotide to isolate cytosine deaminas

<400> SEQUENCE: 10

gacgcatgtg gaagcttaca atgtcgaata acgc                                 34
```

-continued

```
<210> SEQ ID NO 11
<211> LENGTH: 341
<212> TYPE: PRT
<213> ORGANISM: Varicella zoster

<400> SEQUENCE: 11

Met Ser Thr Asp Lys Thr Asp Val Lys Met Gly Val Leu Arg Ile Tyr
1               5                   10                  15

Leu Asp Gly Ala Tyr Gly Ile Gly Lys Thr Thr Ala Ala Glu Glu Phe
            20                  25                  30

Leu His His Phe Ala Ile Thr Pro Asn Arg Ile Leu Leu Ile Gly Glu
        35                  40                  45

Pro Leu Ser Tyr Trp Arg Asn Leu Ala Gly Glu Asp Ala Ile Cys Gly
    50                  55                  60

Ile Tyr Gly Thr Gln Thr Arg Arg Leu Asn Gly Asp Val Ser Pro Glu
65                  70                  75                  80

Asp Ala Gln Arg Leu Thr Ala His Phe Gln Ser Leu Phe Cys Ser Pro
                85                  90                  95

His Ala Ile Met His Ala Lys Ile Ser Ala Leu Met Asp Thr Ser Thr
            100                 105                 110

Ser Asp Leu Val Gln Val Asn Lys Glu Pro Tyr Lys Ile Met Leu Ser
        115                 120                 125

Asp Arg His Pro Ile Ala Ser Thr Ile Cys Phe Pro Leu Ser Arg Tyr
    130                 135                 140

Leu Val Gly Asp Met Ser Pro Ala Ala Leu Pro Gly Leu Leu Phe Thr
145                 150                 155                 160

Leu Pro Ala Glu Pro Pro Gly Thr Asn Leu Val Val Cys Thr Val Ser
                165                 170                 175

Leu Pro Ser His Leu Ser Arg Val Ser Lys Arg Ala Arg Pro Gly Glu
            180                 185                 190

Thr Val Asn Leu Pro Phe Val Met Val Leu Arg Asn Val Tyr Ile Met
        195                 200                 205

Leu Ile Asn Thr Ile Ile Phe Leu Lys Thr Asn Asn Trp His Ala Gly
    210                 215                 220

Trp Asn Thr Leu Ser Phe Cys Asn Asp Val Phe Lys Gln Lys Leu Gln
225                 230                 235                 240

Lys Ser Glu Cys Ile Lys Leu Arg Glu Val Pro Gly Ile Glu Asp Thr
                245                 250                 255

Leu Phe Ala Val Leu Lys Leu Pro Glu Leu Cys Gly Glu Phe Gly Asn
            260                 265                 270

Ile Leu Pro Leu Trp Ala Trp Gly Met Glu Thr Leu Ser Asn Cys Leu
        275                 280                 285

Arg Ser Met Ser Pro Phe Val Leu Ser Leu Glu Gln Thr Pro Gln His
    290                 295                 300

Ala Ala Gln Glu Leu Lys Thr Leu Leu Pro Gln Met Thr Pro Ala Asn
305                 310                 315                 320

Met Ser Ser Gly Ala Trp Asn Ile Leu Lys Glu Leu Val Asn Ala Val
                325                 330                 335

Gln Asp Asn Thr Ser
            340


<210> SEQ ID NO 12
<211> LENGTH: 42
<212> TYPE: PRT
<213> ORGANISM: Varicella zoster
```

-continued

<400> SEQUENCE: 12

Met Ser Thr Asp Lys Thr Asp Val Lys Met Gly Val Leu Arg Ile Tyr
1               5                   10                  15

Leu Asp Gly Ala Tyr Gly Ile Gly Lys Thr Thr Ala Ala Glu Glu Phe
            20                  25                  30

Leu His His Phe Ala Ile Thr Pro Asn Arg
        35                  40

<210> SEQ ID NO 13
<211> LENGTH: 42
<212> TYPE: PRT
<213> ORGANISM: Varicella zoster

<400> SEQUENCE: 13

Met Ser Thr Asp Lys Thr Asp Val Lys Met Gly Val Leu Arg Ile Tyr
1               5                   10                  15

Leu Asp Gly Ala Tyr Gly Ile Gly Lys Thr Thr Ala Ala Glu Glu Phe
            20                  25                  30

Leu His His Phe Ala Ile Thr Pro Asn Arg
        35                  40

<210> SEQ ID NO 14
<211> LENGTH: 21
<212> TYPE: PRT
<213> ORGANISM: Homo sapiens

<400> SEQUENCE: 14

Met Glu Ser Pro Ser Ala Pro Pro His Arg Trp Cys Ile Pro Trp Gln
1               5                   10                  15

Arg Leu Leu Leu Thr
            20

<210> SEQ ID NO 15
<211> LENGTH: 427
<212> TYPE: PRT
<213> ORGANISM: Escherichia coli

<400> SEQUENCE: 15

Val Ser Asn Asn Ala Leu Gln Thr Ile Ile Asn Ala Arg Leu Pro Gly
1               5                   10                  15

Glu Glu Gly Leu Trp Gln Ile His Leu Gln Asp Gly Lys Ile Ser Ala
            20                  25                  30

Ile Asp Ala Gln Ser Gly Val Met Pro Ile Thr Glu Asn Ser Leu Asp
        35                  40                  45

Ala Glu Gln Gly Leu Val Ile Pro Pro Phe Val Glu Pro His Ile His
    50                  55                  60

Leu Asp Thr Thr Gln Thr Ala Gly Gln Pro Asn Trp Asn Gln Ser Gly
65                  70                  75                  80

Thr Leu Phe Glu Gly Ile Glu Arg Trp Ala Glu Arg Lys Ala Leu Leu
                85                  90                  95

Thr His Asp Asp Val Lys Gln Arg Ala Trp Gln Thr Leu Lys Trp Gln
            100                 105                 110

Ile Ala Asn Gly Ile Gln His Val Arg Thr His Val Asp Val Ser Asp
        115                 120                 125

Ala Thr Leu Thr Ala Leu Lys Ala Met Leu Glu Val Lys Gln Glu Val
    130                 135                 140

Ala Pro Trp Ile Asp Leu Gln Ile Val Ala Phe Pro Gln Glu Gly Ile
145                 150                 155                 160

-continued

```
Leu Ser Tyr Pro Asn Gly Glu Ala Leu Leu Glu Glu Ala Leu Arg Leu
                165                 170                 175

Gly Ala Asp Val Val Gly Ala Ile Pro His Phe Glu Phe Thr Arg Glu
            180                 185                 190

Tyr Gly Val Glu Ser Leu His Lys Thr Phe Ala Leu Ala Gln Lys Tyr
        195                 200                 205

Asp Arg Leu Ile Asp Val His Cys Asp Glu Ile Asp Asp Glu Gln Ser
    210                 215                 220

Arg Phe Val Glu Thr Val Ala Ala Leu Ala His His Glu Gly Met Gly
225                 230                 235                 240

Ala Arg Val Thr Ala Ser His Thr Thr Ala Met His Ser Tyr Asn Gly
                245                 250                 255

Ala Tyr Thr Ser Arg Leu Phe Arg Leu Leu Lys Met Ser Gly Ile Asn
            260                 265                 270

Phe Val Ala Asn Pro Leu Val Asn Ile His Leu Gln Gly Arg Phe Asp
        275                 280                 285

Thr Tyr Pro Lys Arg Arg Gly Ile Thr Arg Val Lys Glu Met Leu Glu
    290                 295                 300

Ser Gly Ile Asn Val Cys Phe Gly His Asp Asp Val Phe Asp Pro Trp
305                 310                 315                 320

Tyr Pro Leu Gly Thr Ala Asn Met Leu Gln Val Leu His Met Gly Leu
                325                 330                 335

His Val Cys Gln Leu Met Gly Tyr Gly Gln Ile Asn Asp Gly Leu Asn
            340                 345                 350

Leu Ile Thr His His Ser Ala Arg Thr Leu Asn Leu Gln Asp Tyr Gly
        355                 360                 365

Ile Ala Ala Gly Asn Ser Ala Asn Leu Ile Ile Leu Pro Ala Glu Asn
    370                 375                 380

Gly Phe Asp Ala Leu Arg Arg Gln Val Pro Val Arg Tyr Ser Val Arg
385                 390                 395                 400

Gly Gly Lys Val Ile Ala Ser Thr Gln Pro Ala Gln Thr Thr Val Tyr
                405                 410                 415

Leu Glu Gln Pro Glu Ala Ile Asp Tyr Lys Arg
            420                 425
```

<210> SEQ ID NO 16
<211> LENGTH: 6
<212> TYPE: PRT
<213> ORGANISM: Consensus sequence
<220> FEATURE:
<221> NAME/KEY: misc_feature
<223> OTHER INFORMATION: Consensus sequence A1 from transcriptional dictionary of Locker and Buzard (1990).

<400> SEQUENCE: 16

```
Thr Ala Thr Ala Trp Trp
1               5
```

<210> SEQ ID NO 17
<211> LENGTH: 15
<212> TYPE: PRT
<213> ORGANISM: Consensus sequence
<220> FEATURE:
<221> NAME/KEY: misc_feature
<223> OTHER INFORMATION: Consensus sequence A2calt from transcriptional dictionary of Locker and Buzard (1990).

<400> SEQUENCE: 17

-continued

```
Thr Thr Gly Gly Cys Asn Asn Asn Asn Asn Asn Gly Cys Cys Ala
1               5                   10                  15


<210> SEQ ID NO 18
<211> LENGTH: 14
<212> TYPE: PRT
<213> ORGANISM: Consensus sequence
<220> FEATURE:
<221> NAME/KEY: misc_feature
<223> OTHER INFORMATION: Consensus sequence A4alt  from transcriptional
      dictionary of Locker and Buzard (1990).

<400> SEQUENCE: 18

Arg Arg Arg Asn Cys Cys His Cys Ala Cys Cys Cys Thr Gly
1               5                   10


<210> SEQ ID NO 19
<211> LENGTH: 8
<212> TYPE: PRT
<213> ORGANISM: Consensus sequence
<220> FEATURE:
<221> NAME/KEY: misc_feature
<223> OTHER INFORMATION: Consensus sequence B2 from transcriptional
      dictionary of Locker and Buzard (1990).

<400> SEQUENCE: 19

Gly Thr Gly Gly Trp Trp Trp Gly
1               5


<210> SEQ ID NO 20
<211> LENGTH: 8
<212> TYPE: PRT
<213> ORGANISM: Consensus sequence
<220> FEATURE:
<221> NAME/KEY: misc_feature
<223> OTHER INFORMATION: Consensus sequence B4 from transcriptional
      dictionary of Locker and Buzard (1990).

<400> SEQUENCE: 20

Gly Ser Ser Trp Gly Ser Cys Cys
1               5


<210> SEQ ID NO 21
<211> LENGTH: 10
<212> TYPE: PRT
<213> ORGANISM: Consensus sequence
<220> FEATURE:
<221> NAME/KEY: misc_feature
<223> OTHER INFORMATION: Consensus sequence B12 from transcriptional
      dictionary of Locker and Buzard (1990).

<400> SEQUENCE: 21

Cys Cys Trp Trp Trp Trp Trp Trp Gly Gly
1               5                   10


<210> SEQ ID NO 22
<211> LENGTH: 6
<212> TYPE: PRT
<213> ORGANISM: Consensus sequence
<220> FEATURE:
<221> NAME/KEY: misc_feature
<223> OTHER INFORMATION: Consensus sequence B15 from transcriptional
      dictionary of Locker and Buzard (1990).

<400> SEQUENCE: 22

Gly Ala Ala Ala Gly Tyr
1               5
```

-continued

<210> SEQ ID NO 23
<211> LENGTH: 6
<212> TYPE: PRT
<213> ORGANISM: Consensus sequence
<220> FEATURE:
<221> NAME/KEY: misc_feature
<223> OTHER INFORMATION: Consensus sequence B17 from transcriptional dictionary of Locker and Buzard (1990).

<400> SEQUENCE: 23

Thr Cys Met Tyr Thr Thr
1 5

<210> SEQ ID NO 24
<211> LENGTH: 9
<212> TYPE: PRT
<213> ORGANISM: Consensus sequence
<220> FEATURE:
<221> NAME/KEY: misc_feature
<223> OTHER INFORMATION: Consensus sequence B18 from transcriptional dictionary of Locker and Buzard (1990).

<400> SEQUENCE: 24

Ala Asn Cys Cys Thr Cys Thr Cys Tyr
1 5

<210> SEQ ID NO 25
<211> LENGTH: 8
<212> TYPE: PRT
<213> ORGANISM: Consensus sequence
<220> FEATURE:
<221> NAME/KEY: misc_feature
<223> OTHER INFORMATION: Consensus sequence C5 from transcriptional dictionary of Locker and Buzard (1990).

<400> SEQUENCE: 25

Gly Thr Gly Ser Gly Gly Thr Gly
1 5

<210> SEQ ID NO 26
<211> LENGTH: 8
<212> TYPE: PRT
<213> ORGANISM: Consensus sequence
<220> FEATURE:
<221> NAME/KEY: misc_feature
<223> OTHER INFORMATION: Consensus sequence D9 from transcriptional dictionary of Locker and Buzard (1990).

<400> SEQUENCE: 26

Arg Thr Gly Ala Cys Gly Thr Arg
1 5

<210> SEQ ID NO 27
<211> LENGTH: 12
<212> TYPE: PRT
<213> ORGANISM: Consensus sequence
<220> FEATURE:
<221> NAME/KEY: misc_feature
<223> OTHER INFORMATION: Consensus sequence E5 from transcriptional dictionary of Locker and Buzard (1990).

<400> SEQUENCE: 27

Ala Cys Cys Asn Asn Asn Asn Asn Asn Gly Gly Thr
1 5 10

<210> SEQ ID NO 28
<211> LENGTH: 6
<212> TYPE: PRT
<213> ORGANISM: Consensus Sequence -continued
<220> FEATURE:
<221> NAME/KEY: misc_feature
<223> OTHER INFORMATION: Consensus sequence F2 from transcriptional
dictionary of Locker and Buzard (1990).

<400> SEQUENCE: 28

Thr Gly Arg Met Cys Cys
1 5

<210> SEQ ID NO 29
<211> LENGTH: 8
<212> TYPE: PRT
<213> ORGANISM: Consensus sequence
<220> FEATURE:
<221> NAME/KEY: misc_feature
<223> OTHER INFORMATION: Consensus sequence F6 from transcriptional
dictionary of Locker and Buzard (1990).

<400> SEQUENCE: 29

Thr Cys Asn Thr Ala Cys Thr Cys
1 5

<210> SEQ ID NO 30
<211> LENGTH: 8
<212> TYPE: PRT
<213> ORGANISM: Consensus Sequence
<220> FEATURE:
<221> NAME/KEY: misc_feature
<223> OTHER INFORMATION: Consensus sequence F7 from transcriptional
dictionary of Locker and Buzard (1990).

<400> SEQUENCE: 30

Thr Gly Thr Thr Thr Gly Cys Thr
1 5

<210> SEQ ID NO 31
<211> LENGTH: 5
<212> TYPE: PRT
<213> ORGANISM: Consensus sequence
<220> FEATURE:
<221> NAME/KEY: misc_feature
<223> OTHER INFORMATION: Consensus sequence F9 from transcriptional
dictionary of Locker and Buzard (1990).

<400> SEQUENCE: 31

Thr Cys Ala Cys Thr
1 5

<210> SEQ ID NO 32
<211> LENGTH: 9
<212> TYPE: PRT
<213> ORGANISM: Consensus Sequence
<220> FEATURE:
<221> NAME/KEY: misc_feature
<223> OTHER INFORMATION: Consensus sequence F10 from transcriptional
dictionary of Locker and Buzard (1990).

<400> SEQUENCE: 32

Trp Thr Ser Thr Gly Gly Gly Ala Trp
1 5

<210> SEQ ID NO 33
<211> LENGTH: 8
<212> TYPE: PRT
<213> ORGANISM: Consensus sequence
<220> FEATURE:
<221> NAME/KEY: misc_feature
<223> OTHER INFORMATION: Consensus sequence G2 from transcriptional
dictionary of Locker and Buzard (1990).

-continued

```
<400> SEQUENCE: 33

Ala Ala Asn Cys Cys Ala Ala Ala
1               5


<210> SEQ ID NO 34
<211> LENGTH: 6
<212> TYPE: PRT
<213> ORGANISM: Consensus sequence
<220> FEATURE:
<221> NAME/KEY: misc_feature
<223> OTHER INFORMATION: Consensus sequence G7 from transcriptional
      dictionary of Locker and Buzard (1990).

<400> SEQUENCE: 34

Gly Ala Thr Ala Ala Gly
1               5


<210> SEQ ID NO 35
<211> LENGTH: 17
<212> TYPE: PRT
<213> ORGANISM: Consensus sequence
<220> FEATURE:
<221> NAME/KEY: misc_feature
<223> OTHER INFORMATION: Consensus sequence H1 from transcriptional
      dictionary of Locker and Buzard (1990).

<400> SEQUENCE: 35

Arg Asn Tyr Asn Asn Cys Asn Asn Gly Tyr Asn Gly Lys Thr Asn Tyr
1               5                   10                  15

Asn


<210> SEQ ID NO 36
<211> LENGTH: 16
<212> TYPE: PRT
<213> ORGANISM: Consensus sequence
<220> FEATURE:
<221> NAME/KEY: misc_feature
<223> OTHER INFORMATION: Consensus sequence 90% H1 from transcriptional
      dictionary of Locker and Buzard (1990).

<400> SEQUENCE: 36

Arg Tyr Asn Asn Cys Asn Asn Gly Tyr Asn Gly Lys Thr Asn Tyr Asn
1               5                   10                  15
```